US011918775B2

(12) United States Patent
Spohn et al.

(10) Patent No.: US 11,918,775 B2
(45) Date of Patent: Mar. 5, 2024

(54) PRESSURE JACKETS AND SYRINGE RETENTION FEATURES FOR ANGIOGRAPHY FLUID INJECTORS

(71) Applicant: BAYER HEALTHCARE LLC, Whippany, NJ (US)

(72) Inventors: Michael Spohn, Fenelton, PA (US); Kevin Cowan, Allison Park, PA (US); Arthur Uber, III, Pittsburgh, PA (US); Patrick Campbell, Pittsburgh, PA (US); Andrew Osan, Pittsburgh, PA (US); John Haury, Sewickley, PA (US); James Dedig, Pittsburgh, PA (US); Andrew Naples, Mars, PA (US); Christopher Scutt, Murrysville, PA (US); Michael Swantner, Saxonburg, PA (US); Nathaniel Payor, Tarentum, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 10 days.

(21) Appl. No.: 17/640,956

(22) PCT Filed: Sep. 9, 2020

(86) PCT No.: PCT/US2020/049885
§ 371 (c)(1),
(2) Date: Mar. 7, 2022

(87) PCT Pub. No.: WO2021/050507
PCT Pub. Date: Mar. 18, 2021

(65) Prior Publication Data
US 2022/0313897 A1    Oct. 6, 2022

Related U.S. Application Data

(60) Provisional application No. 62/979,048, filed on Feb. 20, 2020, provisional application No. 62/898,289, filed on Sep. 10, 2019.

(51) Int. Cl.
*A61B 5/00* (2006.01)
*A61M 5/00* (2006.01)

(52) U.S. Cl.
CPC ....... *A61M 5/007* (2013.01); *A61M 2205/586* (2013.01); *A61M 2209/082* (2013.01)

(58) Field of Classification Search
CPC ............ A61M 5/007; A61M 2205/586; A61M 2209/082
See application file for complete search history.

(56) References Cited

U.S. PATENT DOCUMENTS 352,715 A    11/1886    Sandmark
798,093 A    8/1905    Edward
(Continued)

FOREIGN PATENT DOCUMENTS

CN    103917269 A    7/2014
EP    1086661 A2    3/2001
(Continued)

OTHER PUBLICATIONS

"International Preliminary Report on Patentability from PCT Application No. PCT/US2020/049885", dated Mar. 24, 2022.

*Primary Examiner* — Joel F Brutus
(74) *Attorney, Agent, or Firm* — Joseph L. Kent; James R. Stevenson; David Schramm

(57) ABSTRACT

An assembly for retaining a pressure jacket (134) and a syringe (132) on a fluid injector, the assembly including a base plate (1902) comprising a body (1904); at least a first retaining arm (1910*a*) and a second retaining arm (1910*b*) operatively mounted on the body of the base plate, the first retaining arm having a first retaining surface at a distal end thereof and the second retaining arm having a second retaining surface at a distal end thereof, wherein the first retaining surface and the second retaining surface are configured for abutting a distal surface of at least one of the (Continued)

pressure jacket and the syringe; a linkage assembly operatively connected to at least one of the first retaining arm and the second retaining arm, wherein the linkage assembly is configured to move at least one of the first retaining arm and the second retaining arm between at least a first open position and a closed position.

22 Claims, 33 Drawing Sheets

(56) References Cited

U.S. PATENT DOCUMENTS

| | | |
|---|---|---|
| 937,029 A | 10/1909 | Blessing et al. |
| 2,514,575 A | 7/1950 | Hein et al. |
| 2,667,163 A | 1/1954 | Smith |
| 2,667,164 A | 1/1954 | Smith |
| 2,667,165 A | 1/1954 | Smith |
| 2,667,872 A | 2/1954 | Smith |
| 2,672,866 A | 3/1954 | Kater |
| 2,673,561 A | 3/1954 | Peterson, Jr. |
| 2,688,963 A | 9/1954 | Smith |
| 2,688,964 A | 9/1954 | Smith |
| 2,690,179 A | 9/1954 | Fox |
| 2,717,598 A | 9/1955 | Krasno |
| 2,805,662 A | 9/1957 | Lawshe et al. |
| 2,911,972 A | 11/1959 | Elinger |
| 2,935,067 A | 5/1960 | Bouet |
| 2,950,717 A | 8/1960 | Bonet |
| 3,155,281 A | 11/1964 | Stracey |
| 3,161,194 A | 12/1964 | Chapman |
| 3,161,195 A | 12/1964 | Taylor et al. |
| 3,172,577 A | 3/1965 | Hartung |
| 3,190,619 A | 6/1965 | Penney et al. |
| 3,231,139 A | 1/1966 | Bouet |
| 3,301,293 A | 1/1967 | Santelli |
| 3,340,869 A | 9/1967 | Bane |
| 3,390,821 A | 7/1968 | Mullan |
| 3,411,503 A | 11/1968 | Santomieri |
| 3,442,424 A | 5/1969 | Sam et al. |
| 3,471,058 A | 10/1969 | Peter et al. |
| 3,473,524 A | 10/1969 | John |
| 3,474,844 A | 10/1969 | Rudolph et al. |
| 3,506,163 A | 4/1970 | James et al. |
| 3,557,788 A | 1/1971 | Swartz |
| 3,613,963 A | 10/1971 | Berkmuller |
| 3,618,846 A | 11/1971 | Poli |
| 3,826,409 A | 7/1974 | Chilcoate |
| 3,873,003 A | 3/1975 | Seiferth et al. |
| 3,938,514 A | 2/1976 | Boucher |
| 4,035,461 A | 7/1977 | Korth |
| 4,044,836 A | 8/1977 | Martin et al. |
| 4,064,879 A | 12/1977 | Leibinsohn |
| 4,066,080 A | 1/1978 | Sneider |
| 4,131,217 A | 12/1978 | Sandegren |
| 4,136,802 A | 1/1979 | Mascia et al. |
| 4,171,698 A | 10/1979 | Genese |
| 4,349,129 A | 9/1982 | Amneus |
| 4,392,491 A | 7/1983 | Takasugi et al. |
| 4,411,656 A | 10/1983 | Cornett, III |
| 4,526,296 A | 7/1985 | Berger et al. |
| 4,753,638 A | 6/1988 | Peters |
| 4,773,458 A | 9/1988 | Touzani |
| 4,850,807 A | 7/1989 | Frantz |
| 4,969,879 A | 11/1990 | Lichte |
| 5,000,739 A | 3/1991 | Kulisz et al. |
| 5,201,438 A | 4/1993 | Norwood |
| 5,209,372 A | 5/1993 | Norwood |
| 5,236,204 A | 8/1993 | Hempel |
| 5,238,150 A | 8/1993 | Williams |
| 5,240,130 A | 8/1993 | Osbakk |
| 5,242,422 A | 9/1993 | Schneberger et al. |
| 5,269,428 A | 12/1993 | Gilbert |
| 5,333,761 A | 8/1994 | Davis et al. |
| 5,353,961 A | 10/1994 | Debush |
| 5,370,250 A | 12/1994 | Gilbert |
| 5,383,858 A | 1/1995 | Reilly et al. |
| 5,397,157 A | 3/1995 | Hempel et al. |
| 5,507,535 A | 4/1996 | McKamey et al. |
| 5,573,129 A | 11/1996 | Nagata et al. |
| 5,584,413 A | 12/1996 | Jung |
| 5,592,948 A | 1/1997 | Gatten |
| 5,609,580 A | 3/1997 | Kwiatkowski et al. |
| 5,615,791 A | 4/1997 | Vatelot et al. |
| 5,638,995 A | 6/1997 | Mazda |
| 5,683,369 A | 11/1997 | Tsukada |
| 5,758,789 A | 6/1998 | Shin et al. |
| 5,794,107 A | 8/1998 | Russell |
| 5,827,233 A | 10/1998 | Futagawa et al. |
| 5,836,922 A | 11/1998 | Hansen et al. |
| 5,873,861 A | 2/1999 | Hitchins et al. |
| 5,899,889 A | 5/1999 | Futagawa et al. |
| RE36,377 E | 11/1999 | Gilbert |
| 5,979,326 A | 11/1999 | Ohinata |
| 5,984,378 A | 11/1999 | Ostrander et al. |
| 6,054,194 A | 4/2000 | Kane |
| 6,062,437 A | 5/2000 | Mascitelli |
| 6,077,252 A | 6/2000 | Siegel |
| 6,105,815 A | 8/2000 | Mazda |
| 6,142,976 A | 11/2000 | Kubo |
| 6,216,915 B1 | 4/2001 | Harman et al. |
| 6,224,577 B1 | 5/2001 | Dedola et al. |
| 6,250,505 B1 | 6/2001 | Petit |
| 6,315,761 B1 | 11/2001 | Shcherbina et al. |
| 6,319,235 B1 | 11/2001 | Yoshino |
| 6,322,535 B1 | 11/2001 | Hitchins et al. |
| 6,332,876 B1 | 12/2001 | Poynter et al. |
| 6,485,471 B1 | 11/2002 | Zivitz et al. |
| 6,558,358 B2 | 5/2003 | Rosoff et al. |
| 6,578,738 B1 | 6/2003 | Keller |
| 6,616,000 B1 | 9/2003 | Renz |
| 6,620,134 B1 | 9/2003 | Trombley, III et al. |
| 6,634,524 B1 | 10/2003 | Helmenstein |
| 6,652,489 B2 | 11/2003 | Trocki et al. |
| 6,702,143 B2 | 3/2004 | Wang |
| 6,716,195 B2 | 4/2004 | Nolan, Jr. et al. |
| 6,773,417 B2 | 8/2004 | Fitzgibbons et al. |
| 6,840,164 B2 | 1/2005 | Eastman |
| 6,866,039 B1 | 3/2005 | Wright et al. |
| 6,869,419 B2 | 3/2005 | Dragan et al. |
| 6,921,384 B2 | 7/2005 | Reilly et al. |
| RE38,770 E | 8/2005 | Gilbert |
| 6,974,443 B2 | 12/2005 | Reilly et al. |
| 7,004,213 B2 | 2/2006 | Hansen |
| 7,011,650 B2 | 3/2006 | Rosoff et al. |
| 7,101,352 B2 | 9/2006 | Dochon et al. |
| 7,192,416 B1 | 3/2007 | Lazzaro et al. |
| 7,192,549 B2 | 3/2007 | Hansen |
| 7,250,039 B2 | 7/2007 | Fitzgerald |
| 7,309,463 B2 | 12/2007 | Hansen |
| 7,513,378 B2 | 4/2009 | Mori et al. |
| 7,553,294 B2 | 6/2009 | Lazzaro et al. |
| 7,563,249 B2 | 7/2009 | Schriver et al. |
| 7,604,623 B2 | 10/2009 | Brunner et al. |
| 7,666,169 B2 | 2/2010 | Cowan et al. |
| 7,802,691 B2 | 9/2010 | Musalek et al. |
| 8,388,580 B2 | 3/2013 | Schriver et al. |
| 8,740,877 B2 | 6/2014 | Borlaug et al. |
| 8,872,708 B2 | 10/2014 | Hill et al. |
| 8,882,708 B2 | 11/2014 | Hieb et al. |
| 8,945,051 B2 | 2/2015 | Schriver et al. |
| 9,173,995 B1 | 11/2015 | Tucker et al. |
| 9,180,252 B2 | 11/2015 | Gelblum et al. |
| 9,199,033 B1 | 12/2015 | Cowan et al. |
| 9,474,857 B2 | 10/2016 | Riley et al. |
| 9,566,381 B2 | 2/2017 | Barron et al. |
| 10,022,493 B2 | 7/2018 | Shearer, Jr. et al. |
| 10,046,106 B2 | 8/2018 | Cowan et al. |
| 10,105,491 B2 | 10/2018 | Gelblum et al. |
| 10,124,110 B2 | 11/2018 | Dedig et al. |
| 10,507,319 B2 | 12/2019 | Haury et al. |
| 10,857,345 B2 | 12/2020 | Uber, III et al. |
| 10,933,190 B2 | 3/2021 | Berry et al. |
| 2002/0010596 A1 | 1/2002 | Matory |

(56) References Cited

U.S. PATENT DOCUMENTS

| | | |
|---|---|---|
| 2004/0249344 A1 | 12/2004 | Nemoto et al. |
| 2009/0112087 A1 | 4/2009 | Fago |
| 2010/0091361 A1 | 4/2010 | Yuuki |
| 2011/0218434 A1 | 9/2011 | Ziemba et al. |
| 2012/0020911 A1 | 1/2012 | Seliktar et al. |
| 2012/0209111 A1 | 8/2012 | Cowan et al. |
| 2012/0253291 A1 | 10/2012 | Ivosevic et al. |
| 2013/0023048 A1 | 1/2013 | Kim et al. |
| 2013/0030291 A1 | 1/2013 | Lewis |
| 2013/0067416 A1 | 3/2013 | Barron et al. |
| 2013/0211248 A1 | 8/2013 | Cowan et al. |
| 2013/0281940 A1 | 10/2013 | Gelblum et al. |
| 2016/0250409 A1* | 9/2016 | Dedig .................. A61M 5/007 600/432 |
| 2017/0035974 A1 | 2/2017 | Berry et al. |
| 2018/0015274 A1 | 1/2018 | Haury et al. |
| 2018/0161496 A1 | 6/2018 | Berry et al. |
| 2019/0192770 A1 | 6/2019 | Spohn et al. |
| 2021/0193289 A1 | 6/2021 | Cowan et al. |
| 2021/0220561 A1 | 7/2021 | Spohn et al. |
| 2021/0316065 A1 | 10/2021 | Berry et al. |
| 2021/0353870 A1 | 11/2021 | Volkar et al. |

FOREIGN PATENT DOCUMENTS

| | | |
|---|---|---|
| EP | 1572266 A2 | 9/2005 |
| EP | 1572266 B1 | 4/2008 |
| EP | 2098258 A1 | 9/2009 |
| EP | 3057648 A1 | 8/2016 |
| FR | 1288915 A | 3/1962 |
| GB | 2214819 A | 9/1989 |
| GB | 2374143 A | 10/2002 |
| WO | 9221391 A1 | 12/1992 |
| WO | 9707841 A2 | 3/1997 |
| WO | 0204049 A1 | 1/2002 |
| WO | 2009038955 A1 | 3/2009 |
| WO | 2010004206 A2 | 1/2010 |
| WO | 2010014654 A1 | 2/2010 |
| WO | 2011129175 A1 | 10/2011 |
| WO | 2012061140 A1 | 5/2012 |
| WO | 2012155035 A1 | 11/2012 |
| WO | 2014027009 A1 | 2/2014 |
| WO | 2015058088 A1 | 4/2015 |
| WO | 2015066506 A2 | 5/2015 |
| WO | 2015164783 A1 | 10/2015 |
| WO | 2016058946 A1 | 4/2016 |
| WO | 2016069711 A1 | 5/2016 |
| WO | 2016069714 A1 | 5/2016 |
| WO | 2016112163 A1 | 7/2016 |
| WO | 2016172467 A1 | 10/2016 |
| WO | 2016191485 A1 | 12/2016 |
| WO | 2017040154 A1 | 3/2017 |
| WO | 2018053074 A1 | 3/2018 |
| WO | 2018057386 A1 | 3/2018 |
| WO | 2019152978 A1 | 8/2019 |
| WO | 2020055785 A1 | 3/2020 |
| WO | 2020055818 A1 | 3/2020 |
| WO | 2022035791 A1 | 2/2022 |

* cited by examiner

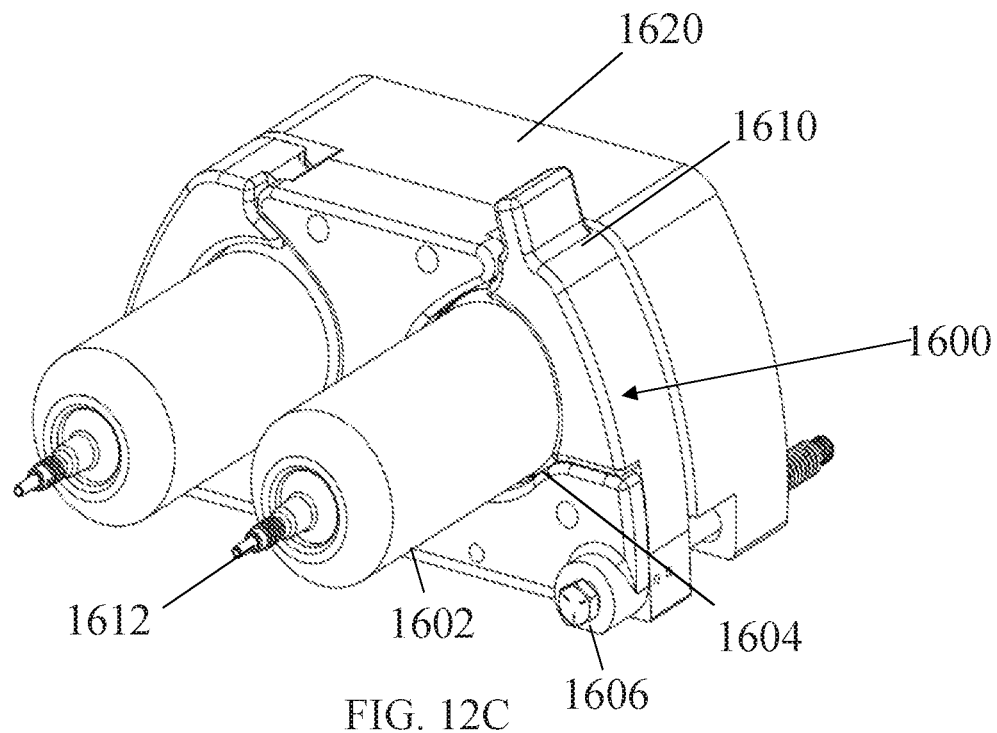
FIG. 12C
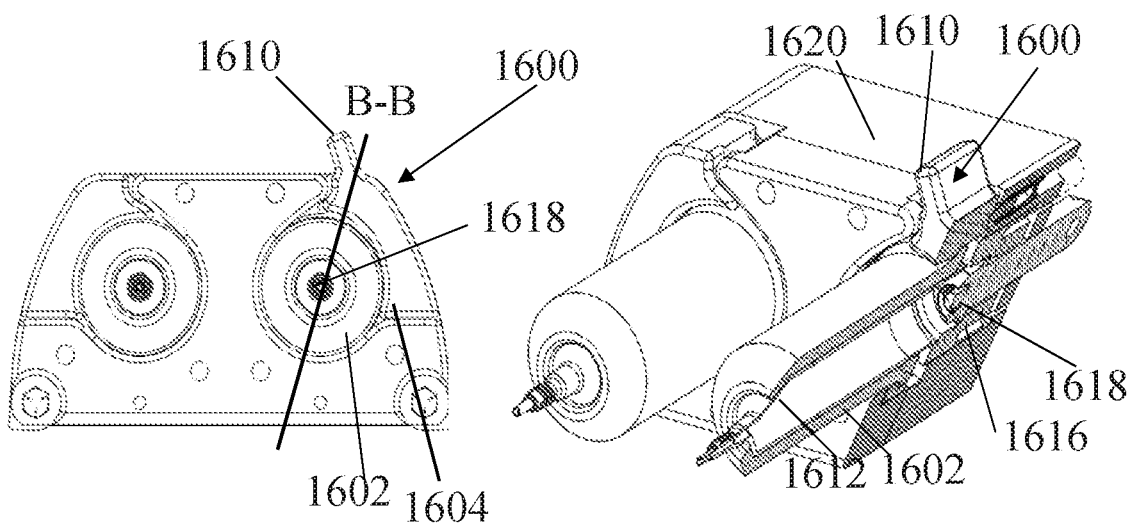
FIG. 12D
FIG. 12E

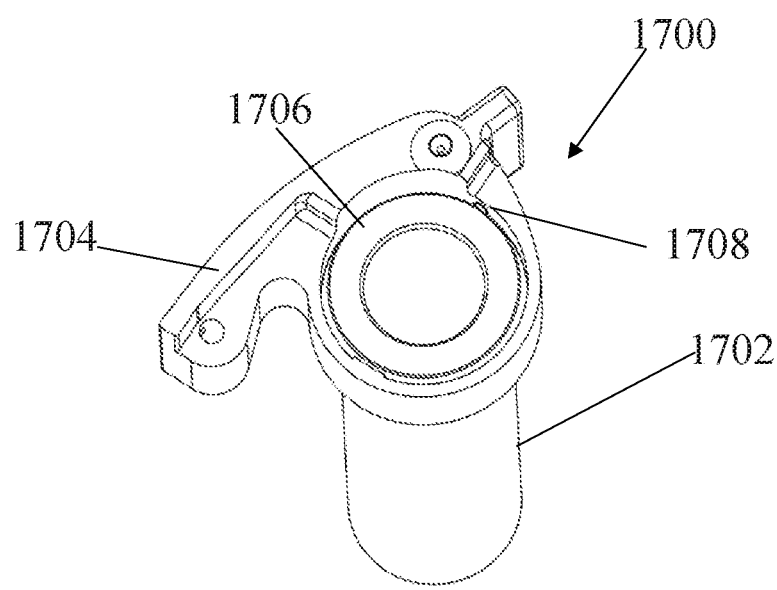
FIG. 13A
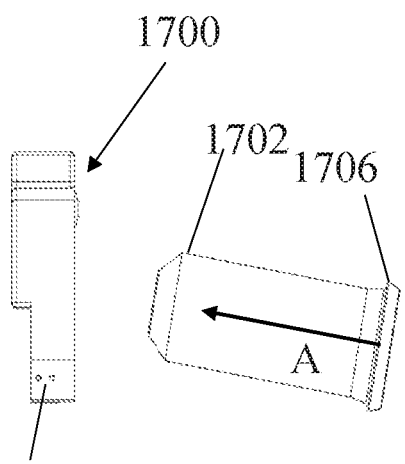 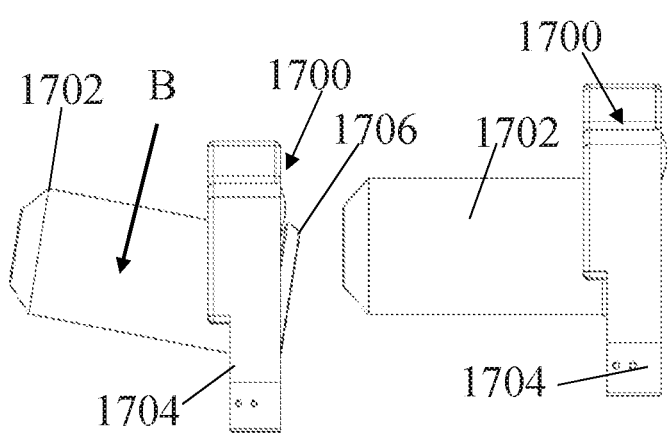 
FIG. 13B  FIG. 13C  FIG. 13D
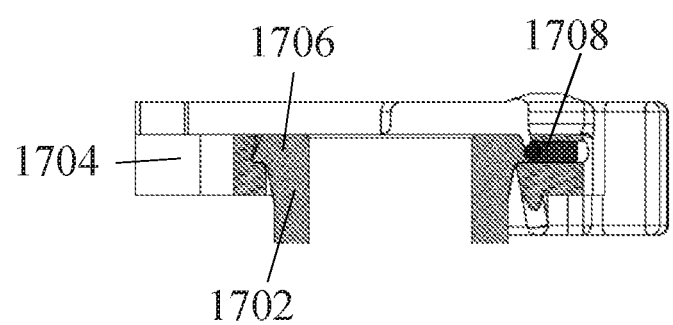
FIG. 13E

PRESSURE JACKETS AND SYRINGE RETENTION FEATURES FOR ANGIOGRAPHY FLUID INJECTORS

CROSS REFERENCE TO RELATED APPLICATION

This present application is a U.S. national phase application under 35 U.S.C. § 371 of PCT International Application No. PCT/US2020/049885, filed 9 Sep. 2020, and claims the benefit of U.S. Provisional Patent Application No. 62/898,289, filed on 10 Sep. 2019, and U.S. Provisional Patent Application No. 62/979,048, filed 20 Feb. 2020, the disclosures of which are incorporated in their entireties by this reference.

BACKGROUND OF THE DISCLOSURE

Field of the Disclosure

The present disclosure relates generally to angiography fluid injectors having the one or more syringe retention features configured for retaining a syringe and a pressure jacket, wherein the syringe retention features engage a distal end of the syringe and the pressure jacket to limit movement of the syringe in a distal direction during a fluid injection procedure and support the distal end of the syringe under pressure.

Description of Related Art

In many medical diagnostic and therapeutic procedures, a medical practitioner injects a patient with one or more medical fluids. In recent years, a number of injector-actuated syringes and powered fluid injectors for pressurized injection of medical fluids, such as a contrast medium (often referred to simply as "contrast"), a flushing agent, such as saline, and other medical fluids, have been developed for use in contrast enhanced imaging procedures such as cardiovascular angiography (CV), computed tomography (CT), ultrasound, magnetic resonance imaging (MRI), positron emission tomography (PET), and other imaging procedures. In general, these fluid injectors are designed to deliver a preset amount of one or more fluid at a preset pressure and/or flow rate.

Typically, fluid injectors have at least one drive member, such as a piston, that connects to the syringe, for example via connection with a plunger or an engagement feature on a proximal end wall of the syringe. The syringe may include a rigid barrel with the syringe plunger being slidably disposed within the barrel. In some examples, the syringe may include a rolling diaphragm barrel configuration having a flexible sidewall configured to roll upon itself, where the proximal end wall of the syringe body releasably engages with the at least one drive member. The drive members drive the plungers or the rolling diaphragm/proximal end wall in a proximal and/or distal direction relative to a longitudinal axis of the barrel to draw fluid into or deliver the fluid from the syringe barrel.

Syringes for use with fluid injectors may be made of various medical-grade plastic materials with a certain minimum wall thickness. Syringe thickness is an important design factor, as fluid pressures of up to 1200 psi may be used during an injection procedure. During certain injection procedures, the syringe itself may not be capable of withstanding the high pressure without excessive radial expansion of the syringe wall under such pressure. This may result in undesired changes in fluid delivery volumes and flow rates or potentially even structural failure. Fluid injectors having at least one pressure jacket have been developed for enclosing at least a portion of the syringe and preventing radial expansion of the syringe due to buildup of fluid pressure within the syringe. Conventional pressure jacket designs include a rigid cylindrical pressure jacket that engages a rigid cap at the distal end to maintain the syringe within the pressure jacket.

There is a current need in the art for a syringe retaining interface that assists in limiting movement and/or expansion of a syringe within a pressure jacket during a filling procedure or a pressurized injection fluid delivery procedure. In one example, there is a need for a syringe retaining interface that assists in limiting movement of the syringe in a distal direction relative to the pressure jacket and/or injector housing during an injection procedure while still allowing ready insertion and removal of the syringe and/or the pressure jacket.

SUMMARY OF THE DISCLOSURE

In view of the above-identified needs, provided is a system and method for retaining at least one syringe in a medical injector during injection of a medical fluid. In some examples of the present disclosure, an assembly for retaining a pressure jacket and a syringe on a fluid injector is described. The assembly comprises a base plate comprising a body; at least a first retaining arm and a second retaining arm operatively mounted on the body of the base plate, the first retaining arm having a first retaining surface at a distal end thereof and the second retaining arm having a second retaining surface at a distal end thereof. The first retaining surface and the second retaining surface are configured for abutting a distal surface of at least one of the pressure jacket and the syringe. The assembly includes a linkage assembly operatively connected to at least one of the first retaining arm and the second retaining arm. The linkage assembly is configured to move at least one of the first retaining arm and the second retaining arm between at least a first open position and a closed position.

In further examples of the present disclosure, the linkage assembly is operatively connected to a proximal end of the first retaining arm and a proximal end of the second retaining arm. The linkage assembly operatively connects the first retaining arm to the second retaining arm such that the first retaining arm and the second retaining arm are configured to move in unison between at least the first open position and the closed position. The linkage assembly comprises at least one biasing member configured for biasing the first retaining arm and the second retaining arm to move in unison between at least the first open position and the closed position. The first retaining arm and the second retaining arm are connected to the body of the base plate at a first pivot point and a second pivot point, respectively, so that the first retaining arm and the second retaining arm pivot between at least the first open position and the closed position about the first pivot point and the second pivot point. The first retaining arm and the second retaining arm are further configured to move to a second open position between the first open position and the closed position. In the first open position, the first retaining surface of the first retaining arm and the second retaining surface of the second retaining arm are separated from one another at a first distance configured to permit insertion and engagement of at least one of the pressure jacket and the syringe with the fluid injector and/or removal of at least one of the pressure jacket and the syringe from the fluid injector. In the closed position, the first retaining surface of the first retaining arm and the second retaining surface of the second retaining arm are separated from one another at a second distance to retain the pressure jacket and the syringe between the first retaining arm and the second retaining arm. In the second open position, the first retaining surface of the first retaining arm and the second retaining surface of the second retaining arm are separated from one another at a third distance to retain the pressure jacket in the fluid injector and allow insertion and removal of the syringe from the fluid injector. The first distance is greater than the second distance. The third distance is less than the first distance and greater than the second distance. Each of the first retaining arm and the second retaining arm comprises at least one base member operatively connected to the body of the base plate and at least one retaining portion provided on a distal end of the at least one base member. The first retaining surface of the first retaining arm comprises a first syringe retaining surface and a first pressure jacket retaining surface. The second retaining surface of the second retaining arm comprises a second syringe retaining surface and a second pressure jacket retaining surface. The at least one biasing member is configured to bias the first retaining arm and the second retaining arm in at least one of the first open position, the closed position, or the second open position, such that the arms will be held in either the first open position, the closed position, and the second open position. In specific embodiments, the at least one biasing member is configured to bias the first retaining arm and the second retaining arm in the first open position and the closed position, such that the arms will be held in the first open position and the closed position.

In other examples of the present disclosure, an assembly for retaining a pressure jacket and a syringe in a fluid injector is described. The assembly comprises a base plate comprising a body; and at least a first retaining arm and a second retaining arm operatively mounted on the body of the base plate. The first retaining arm has a first retaining surface at a distal end thereof and the second retaining arm has a second retaining surface at a distal end thereof, where the first retaining surface and the second retaining surface are configured for abutting a distal surface of at least one of the pressure jacket and the syringe. Each of the first retaining arm and the second retaining arm comprises at least one base member operatively connected to the body of the base plate and at least one retaining portion provided on a distal end of the at least one base member configured to engage at least one of the pressure jacket and the syringe.

In other examples of the present disclosure, the first retaining surface of the first retaining arm and the second retaining surface of the second retaining arm each include at least one inner protrusion to engage a distal end of at least one of the pressure jacket and the syringe. At least one of the inner protrusions is a syringe retaining protrusion extending at an angle relative to a longitudinal axis of the syringe and configured to interact with a corresponding angled distal surface of a circumferential wall on a distal end of the syringe to urge the distal ends of the first retaining arm and the second retaining arm with an inward retaining force. In certain aspects, at least one of the first retaining arm and the second retaining arm includes at least one finger tab configured to assist in moving the first retaining arm and the second retaining arm between a closed position and an open position. In other aspects, each of the first retaining arm and the second retaining arm include at least one finger tab to assist in moving the first retaining arm and the second retaining arm between the closed position and the open position. In certain aspects, the first retaining surface of the first retaining arm and the second retaining surface of the second retaining arm each define a retaining groove to receive at least a portion of the distal end of the pressure jacket. In the open position, the first retaining surface of the first retaining arm and the second retaining surface of the second retaining arm are separated from one another at a first distance configured to permit insertion and engagement of at least one of the pressure jacket and the syringe with the fluid injector and/or removal of at least one of the pressure jacket and the syringe from the fluid injector. In the closed position, the first retaining surface of the first retaining arm and the second retaining surface of the second retaining arm are separated from one another at a second distance configured to retain the pressure jacket and the syringe between the first retaining arm and the second retaining arm. The first distance is greater than the second distance. The retaining portions of the first retaining arm and the second retaining arm have a curvature relative to a longitudinal axis of the syringe corresponding to at least a portion of a distal end of at least one of the pressure jacket and the syringe.

In further examples of the present disclosure, an assembly for retaining a pressure jacket and a syringe on a fluid injector is described. The assembly comprises a base plate comprising a body; at least a first retaining arm and a second retaining arm operatively mounted on the body of the base plate. The first retaining arm has a first retaining surface at a distal end thereof and the second retaining arm has a second retaining surface at a distal end thereof, where the first retaining surface and the second retaining surface are configured for abutting a distal surface of at least one of the pressure jacket and the syringe. The assembly includes a linkage assembly operatively connected to the first retaining arm and the second retaining arm, where the linkage assembly is configured to move at least one of the first retaining arm and the second retaining arm between at least a first open position and a closed position. Each of the first retaining arm and the second retaining arm comprises at least one base member operatively connected to the body of the base plate and at least one retaining portion provided on a distal end of the at least one base member configured to engage at least one of the pressure jacket and the syringe when in the closed position. The first retaining surface of the first retaining arm is provided on the retaining portion of the first retaining arm and the second retaining surface of the second retaining arm is provided on the retaining portion of the second retaining arm.

In further examples of the present disclosure, the linkage assembly is operatively connected to a proximal end of the first retaining arm and a proximal end of the second retaining arm. The linkage assembly operatively connects the first retaining arm to the second retaining arm such that the first retaining arm and the second retaining arm are configured to move in unison between at least the first open position and the closed position. The linkage assembly comprises at least one biasing member configured for biasing the first retaining arm and the second retaining arm to move in unison between at least the first open position and the closed position. The first retaining arm and the second retaining arm are connected to the body of the base plate at a first pivot point and a second pivot point, respectively, so that the first retaining arm and the second retaining arm pivot between at least the first open position and the closed position about the first pivot point and the second pivot point. The first retaining arm and the second retaining arm are further configured to move to a second open position between the first open position and the closed position. In the first open position, the first retaining surface of the first retaining arm and the second retaining surface of the second retaining arm are separated from one another at a first distance configured to permit insertion and engagement of at least one of the pressure jacket and the syringe with the fluid injector and/or removal of at least one of the pressure jacket and the syringe from the fluid injector. In the closed position, the first retaining surface of the first retaining arm and the second retaining surface of the second retaining arm are separated from one another at a second distance configured to retain the pressure jacket and the syringe between the first retaining arm and the second retaining arm. The first distance is greater than the second distance. The first retaining surface of the first retaining arm and the second retaining surface of the second retaining arm each include at least one inner protrusion to engage a distal end of at least one of the pressure jacket and the syringe. In certain aspects, the at least one inner protrusion is a syringe retaining protrusion extending at an angle relative to a longitudinal axis of the syringe and configured to interact with a corresponding angled distal surface of a circumferential wall on a distal end of the syringe to urge the distal ends of the first retaining arm and the second retaining arm with an inward retaining force. In certain aspects, at least one of the first retaining arm and the second retaining arm includes at least one finger tab configured to assist in moving the first retaining arm and the second retaining arm between the closed position and the open position. In certain aspects, each of the first retaining arm and the second retaining arm includes at least one finger tab configured to assist in moving the first retaining arm and the second retaining arm between the closed position and the open position. In certain aspects, the first retaining surface of the first retaining arm and the second retaining surface of the second retaining arm each define a retaining groove to receive at least a portion of the distal end of the pressure jacket. The first retaining surface of the first retaining arm and the second retaining surface of the second retaining arm have a curvature relative to a longitudinal axis of the syringe corresponding to at least a portion of a distal end of at least one of the pressure jacket and the syringe.

In further examples of the present disclosure, a fluid injector comprising an assembly for retaining a pressure jacket and a syringe is described. The fluid injector comprises injector housing; at least one port defined in the injector housing to receive at least one syringe, wherein the syringe is received within at least one pressure jacket; and an assembly for retaining the at least one pressure jacket on the fluid injector and retaining the at least one syringe in the at least one port. The assembly comprises a base plate comprising a body; at least a first retaining arm and a second retaining arm operatively mounted on the body of the base plate, and includes features according to various aspects of the syringe and pressure jacket retention assemblies described herein.

In certain aspects, an electromechanical motor is provided in the injector housing to move the first retaining arm and the second retaining arm between the first open position and the closed position whereas in other aspects, movement of the first retaining arm and the second retaining arm between the first open position and the closed position may be performed manually.

In specific embodiments, the retention features may be utilized with cardiovascular angiography (CV) injectors, which typically require injection pressures of up to 1200 psi. As described herein, such retention features and retaining elements may provide specific designs and features to withstand increased injection pressures.

The following clauses also recite further features of the present disclosure:

Clause 1: An assembly for retaining a pressure jacket and a syringe on a fluid injector, the assembly comprising: a base plate comprising a body; at least a first retaining arm and a second retaining arm operatively mounted on the body of the base plate, the first retaining arm having a first retaining surface at a distal end thereof and the second retaining arm having a second retaining surface at a distal end thereof, wherein the first retaining surface and the second retaining surface are configured for abutting a distal surface of at least one of the pressure jacket and the syringe; a linkage assembly operatively connected to at least one of the first retaining arm and the second retaining arm, wherein the linkage assembly is configured to move at least one of the first retaining arm and the second retaining arm between at least a first open position and a closed position.

Clause 2: The assembly of Clause 1, wherein the linkage assembly is operatively connected to a proximal end of the first retaining arm and a proximal end of the second retaining arm.

Clause 3: The assembly of Clause 1 or 2, wherein the linkage assembly operatively connects the first retaining arm to the second retaining arm such that the first retaining arm and the second retaining arm are configured to move in unison between at least the first open position and the closed position.

Clause 4: The assembly of Clause 3, wherein the linkage assembly comprises at least one biasing member configured for biasing the first retaining arm and the second retaining arm to move in unison between at least the first open position and the closed position.

Clause 5: The assembly of any of Clauses 1-4, wherein the first retaining arm and the second retaining arm are connected to the body of the base plate at a first pivot point and a second pivot point, respectively, so that the first retaining arm and the second retaining arm pivot between at least the first open position and the closed position about the first pivot point and the second pivot point.

Clause 6: The assembly of any of Clauses 1-5, wherein the first retaining arm and the second retaining arm are further configured to move to a second open position between the first open position and the closed position.

Clause 7: The assembly of Clause 6, wherein, in the first open position, the first retaining surface of the first retaining arm and the second retaining surface of the second retaining arm are separated from one another at a first distance configured to permit insertion and engagement of at least one of the pressure jacket and the syringe with the fluid injector or removal of at least one of the pressure jacket and the syringe from the fluid injector, wherein, in the closed position, the first retaining surface of the first retaining arm and the second retaining surface of the second retaining arm are separated from one another at a second distance to retain the pressure jacket and the syringe between the first retaining arm and the second retaining arm, wherein, in the second open position, the first retaining surface of the first retaining arm and the second retaining surface of the second retaining arm are separated from one another at a third distance to retain the pressure jacket in the fluid injector and allow removal of the syringe from the fluid injector, wherein the first distance is greater than the second distance, and wherein the third distance is less than the first distance and greater than the second distance.

Clause 8: The assembly of any of Clauses 1-7, wherein, in the first open position, the first retaining surface of the first retaining arm and the second retaining surface of the second retaining arm are separated from one another at a first distance configured to permit insertion and engagement of at least one of the pressure jacket and the syringe with the fluid injector or removal of at least one of the pressure jacket and the syringe from the fluid injector, wherein, in the closed position, the first retaining surface of the first retaining arm and the second retaining surface of the second retaining arm are separated from one another at a second distance to retain the pressure jacket and the syringe between the first retaining arm and the second retaining arm, and wherein the first distance is greater than the second distance.

Clause 9: The assembly of any of Clauses 1-8, wherein each of the first retaining arm and the second retaining arm comprises at least one base member operatively connected to the body of the base plate and at least one retaining portion provided on a distal end of the at least one base member.

Clause 10: The assembly of any of Clauses 1-9, wherein the first retaining surface of the first retaining arm comprises a first syringe retaining surface and a first pressure jacket retaining surface, and wherein the second retaining surface of the second retaining arm comprises a second syringe retaining surface and a second pressure jacket retaining surface.

Clause 11: The assembly of any of Clauses 4-10, wherein the at least one biasing member is configured to bias the first retaining arm and the second retaining arm in the first open position or a second open position.

Clause 12: An assembly for retaining a pressure jacket and a syringe in a fluid injector, the assembly comprising: a base plate comprising a body; and at least a first retaining arm and a second retaining arm operatively mounted on the body of the base plate, the first retaining arm having a first retaining surface at a distal end thereof and the second retaining arm having a second retaining surface at a distal end thereof, wherein the first retaining surface and the second retaining surface are configured for abutting a distal surface of at least one of the pressure jacket and the syringe, wherein each of the first retaining arm and the second retaining arm comprises at least one base member operatively connected to the body of the base plate and at least one retaining portion provided on a distal end of the at least one base member configured to engage at least one of the pressure jacket and the syringe.

Clause 13: The assembly of Clause 12, wherein the first retaining surface of the first retaining arm and the second retaining surface of the second retaining arm each include at least one inner protrusion to engage a distal end of at least one of the pressure jacket and the syringe.

Clause 14: The assembly of Clause 13, wherein at least one of the inner protrusions is a syringe retaining protrusion extending at an angle relative to a longitudinal axis of the syringe configured to interact with a corresponding angled surface of a circumferential wall on a distal end of the syringe to urge the distal ends of the first retaining arm and the second retaining arm with an inward retaining force.

Clause 15: The assembly of any of Clauses 12-14, wherein at least one of the first retaining arm and the second retaining arm includes at least one finger tab configured to assist in moving the first retaining arm and the second retaining arm between the closed position and the open position.

Clause 16: The assembly of any of Clauses 12-15, wherein each of the first retaining arm and the second retaining arm includes at least one finger tab to assist in moving the first retaining arm and the second retaining arm between the closed position and the open position.

Clause 17: The assembly of any of Clauses 12-16, wherein the first retaining surface of the first retaining arm and the second retaining surface of the second retaining arm each define a retaining groove to receive at least a portion of the distal end of the pressure jacket.

Clause 18: The assembly of any of Clauses 12-17, wherein, in the open position, the first retaining surface of the first retaining arm and the second retaining surface of the second retaining arm are separated from one another at a first distance configured to permit insertion and engagement of at least one of the pressure jacket and the syringe with the fluid injector or removal of at least one of the pressure jacket and the syringe from the fluid injector, wherein, in the closed position, the first retaining surface of the first retaining arm and the second retaining surface of the second retaining arm are separated from one another at a second distance configured to retain the pressure jacket and the syringe between the first retaining arm and the second retaining arm, and wherein the first distance is greater than the second distance.

Clause 19: The assembly of any of Clauses 12-18, wherein the retaining portions of the first retaining arm and the second retaining arm have a curvature relative to a longitudinal axis of the syringe corresponding to a distal end of at least one of the pressure jacket and the syringe.

Clause 20: An assembly for retaining a pressure jacket and a syringe on a fluid injector, the assembly comprising: a base plate comprising a body; at least a first retaining arm and a second retaining arm operatively mounted on the body of the base plate, the first retaining arm having a first retaining surface at a distal end thereof and the second retaining arm having a second retaining surface at a distal end thereof, wherein the first retaining surface and the second retaining surface are configured for abutting a distal surface of at least one of the pressure jacket and the syringe; a linkage assembly operatively connected to the first retaining arm and the second retaining arm, wherein the linkage assembly is configured to move at least one of the first retaining arm and the second retaining arm between at least a first open position and a closed position, and wherein each of the first retaining arm and the second retaining arm comprises at least one base member operatively connected to the body of the base plate and at least one retaining portion provided on a distal end of the at least one base member configured to engage at least one of the pressure jacket and the syringe when in the closed position, wherein the first retaining surface of the first retaining arm is provided on the retaining portion of the first retaining arm and the second retaining surface of the second retaining arm is provided on the retaining portion of the second retaining arm.

Clause 21: The assembly of Clause 20, wherein the linkage assembly is operatively connected to a proximal end of the first retaining arm and a proximal end of the second retaining arm.

Clause 22: The assembly of Clause 20 or 21, wherein the linkage assembly operatively connects the first retaining arm to the second retaining arm such that the first retaining arm and the second retaining arm are configured to move in unison between at least the first open position and the closed position.

Clause 23: The assembly of Clause 22, wherein the linkage assembly comprises at least one biasing member configured for biasing the first retaining arm and the second retaining arm to move in unison between at least the first open position and the closed position.

Clause 24: The assembly of any of Clauses 20-23, wherein the first retaining arm and the second retaining arm are connected to the body of the base plate at a first pivot point and a second pivot point, respectively, so that the first retaining arm and the second retaining arm pivot between at least the first open position and the closed position about the first pivot point and the second pivot point.

Clause 25: The assembly of any of Clauses 20-24, wherein the first retaining arm and the second retaining arm are further configured to move to a second open position between the first open position and the closed position.

Clause 26: The assembly of any of Clauses 20-25, wherein, in the first open position, the first retaining surface of the first retaining arm and the second retaining surface of the second retaining arm are separated from one another at a first distance configured to permit insertion and engagement of at least one of the pressure jacket and the syringe with the fluid injector or removal of at least one of the pressure jacket and the syringe from the fluid injector, wherein, in the closed position, the first retaining surface of the first retaining arm and the second retaining surface of the second retaining arm are separated from one another at a second distance configured to retain the pressure jacket and the syringe between the first retaining arm and the second retaining arm, and wherein the first distance is greater than the second distance.

Clause 27: The assembly of any of Clauses 20-26, wherein the first retaining surface of the first retaining arm and the second retaining surface of the second retaining arm each include at least one inner protrusion to engage a distal end of at least one of the pressure jacket and the syringe.

Clause 28: The assembly of Clause 27, wherein the at least one inner protrusion is a syringe retaining protrusion extending at an angle relative to a longitudinal axis of the syringe configured to interact with a corresponding angled surface of a circumferential wall on a distal end of the syringe to urge the distal ends of the first retaining arm and the second retaining arm with an inward retaining force.

Clause 29: The assembly of any of Clauses 20-28, wherein at least one of the first retaining arm and the second retaining arm includes at least one finger tab configured to assist in moving the first retaining arm and the second retaining arm between the closed position and the open position.

Clause 30: The assembly of any of Clauses 20-29, wherein each of the first retaining arm and the second retaining arm includes at least one finger tab configured to assist in moving the first retaining arm and the second retaining arm between the closed position and the open position.

Clause 31: The assembly of any of Clauses 20-30, wherein the first retaining surface of the first retaining arm and the second retaining surface of the second retaining arm each define a retaining groove to receive at least a portion of the distal end of the pressure jacket.

Clause 32: The assembly of any of Clauses 20-31, wherein the first retaining surface of the first retaining arm and the second retaining surface of the second retaining arm have a curvature relative to a longitudinal axis of the syringe corresponding to a distal end of at least one of the pressure jacket and the syringe.

Clause 33: A fluid injector, comprising: an injector housing; at least one port defined in the injector housing to receive at least one syringe, wherein the syringe is received within at least one pressure jacket; and an assembly for retaining the at least one pressure jacket on the fluid injector and retaining the at least one syringe in the at least one port, the assembly comprising: a base plate comprising a body; at least a first retaining arm and a second retaining arm operatively mounted on the body of the base plate, the first retaining arm having a first retaining surface at a distal end thereof and the second retaining arm having a second retaining surface at a distal end thereof, wherein the first retaining surface and the second retaining surface are configured for abutting a distal surface of at least one of the pressure jacket and syringe; a linkage assembly operatively connected to at least one of the first retaining arm and the second retaining arm, wherein the linkage assembly is configured to move at least one of the first retaining arm and the second retaining arm between at least a first open position and a closed position, and wherein each of the first retaining arm and the second retaining arm comprises at least one base member operatively connected to the body of the base plate and at least one retaining portion provided on a distal end of the at least one base member to engage at least one of the pressure jacket and the syringe when in the closed position.

Clause 34: The fluid injector of Clause 33, wherein the linkage assembly is operatively connected to a proximal end of the first retaining arm and a proximal end of the second retaining arm.

Clause 35: The fluid injector of Clause 33 or 34, wherein the linkage assembly operatively connects the first retaining arm to the second retaining arm such that the first retaining arm and the second retaining arm are configured to move in unison between at least the first open position and the closed position.

Clause 36: The fluid injector of Clause 35, wherein the linkage assembly comprises at least one biasing member configured for biasing the first retaining arm and the second retaining arm to move in unison between at least the first open position and the closed position.

Clause 37: The fluid injector of any of Clauses 33-36, wherein the first retaining arm and the second retaining arm are connected to the body of the base plate at a first pivot point and a second pivot point, respectively, so that the first retaining arm and the second retaining arm pivot between at least the first open position and the closed position about the first pivot point and the second pivot point.

Clause 38: The fluid injector of any of Clauses 33-37, wherein the first retaining arm and the second retaining arm are further configured to move to a second open position between the first open position and the closed position.

Clause 39: The fluid injector of any of Clauses 33-38, wherein, in the first open position, the first retaining surface of the first retaining arm and the second retaining surface of the second retaining arm are separated from one another at a first distance configured to permit insertion and engagement of at least one of the pressure jacket and the syringe with the fluid injector or removal of at least one of the pressure jacket and the syringe from the fluid injector, wherein, in the closed position, the first retaining surface of the first retaining arm and the second retaining surface of the second retaining arm are separated from one another at a second distance configured to retain the pressure jacket and the syringe between the first retaining arm and the second retaining arm, and wherein the first distance is greater than the second distance.

Clause 40: The fluid injector of any of Clauses 33-39, wherein the first retaining surface of the first retaining arm and the second retaining surface of the second retaining arm each include at least one inner protrusion to engage a distal end of at least one of the pressure jacket and the syringe.

Clause 41: The fluid injector of Clause 40, wherein the at least one inner protrusion is a syringe retaining protrusion extending at an angle relative to a longitudinal axis of the syringe configured to interact with a corresponding angled surface of a circumferential wall on a distal end of the syringe to urge the distal ends of the first retaining arm and the second retaining arm with an inward retaining force.

Clause 42: The fluid injector of any of Clauses 33-41, wherein at least one of the first retaining arm and the second retaining arm includes at least one finger tab configured to assist in moving the first retaining arm and the second retaining arm between the closed position and the first open position.

Clause 43: The fluid injector of any of Clauses 33-42, wherein each of the first retaining arm and the second retaining arm includes at least one finger tab configured to assist in moving the first retaining arm and the second retaining arm between the closed position and the first open position.

Clause 44: The fluid injector of any of Clauses 33-43, wherein the first retaining surface of the first retaining arm and the second retaining surface of the second retaining arm each define a retaining groove to receive at least a portion of the distal end of the pressure jacket.

Clause 45: The fluid injector of any of Clauses 33-44, wherein the first retaining surface of the first retaining arm and the second retaining surface of the second retaining arm have a curvature relative to a longitudinal axis of the syringe corresponding to a distal end of at least one of the pressure jacket and the syringe.

Clause 46: The fluid injector of any of Clauses 33-45, further comprising an electromechanical motor provided in the injector housing to move the first retaining arm and the second retaining arm between the open position and the closed position.

Clause 47: The fluid injector of any of Clauses 33-46, wherein the syringe comprises a drip flange provided on a distal end of the syringe, and wherein the first retaining surface of the first retaining arm and the second retaining surface of the second retaining arm are configured to engage the drip flange of the syringe to retain the syringe in the at least one port of the injector housing.

Further details and advantages of the various examples described in detail herein will become clear upon reviewing the following detailed description of the various examples in conjunction with the accompanying drawing figures.

BRIEF DESCRIPTION OF THE DRAWINGS

FIGS. 12A to 12H illustrate a fluid injector having a 2-positon breech loading pressure jacket carriage configuration according to one embodiment.

FIGS. 13A to 13E illustrate a mechanism for engaging the pressure jacket in a receiving portion of a fluid injector carriage according to one embodiment.

FIG. 15A is a perspective drawing of the retention mechanism.

FIG. 15B is a side view of a linkage arrangement of the retention mechanism. FIG. 15C is a cross-sectional view of the support arms for the distal retaining surfaces.

FIG. 16A is a perspective drawing of the retention mechanism. FIG. 16B is a side view of a linkage arrangement of the retention mechanism. FIG. 16C is a cross-sectional view of the support arms for the distal retaining surfaces.

FIG. 17A is a perspective drawing of the retention mechanism. FIG. 17B is a side view of a linkage arrangement of the retention mechanism. FIG. 17C is a cross-sectional view of the support arms for the distal retaining surfaces.

FIG. 20A is a perspective drawing of the retention mechanism.

FIG. 20B is a side view of a linkage arrangement of the retention mechanism. FIG. 20C is a cross-sectional view of the linkage arrangement.

FIG. 21A is a perspective drawing of the retention mechanism. FIG. 21B is a side view of a linkage arrangement of the retention mechanism. FIG. 21C is a cross-sectional view of the linkage arrangement.

FIG. 22A is a perspective drawing of the retention mechanism. FIG. 22B is a side view of a linkage arrangement of the retention mechanism. FIG. 22C is a cross-sectional view of the linkage arrangement.

DETAILED DESCRIPTION

Figure 1:
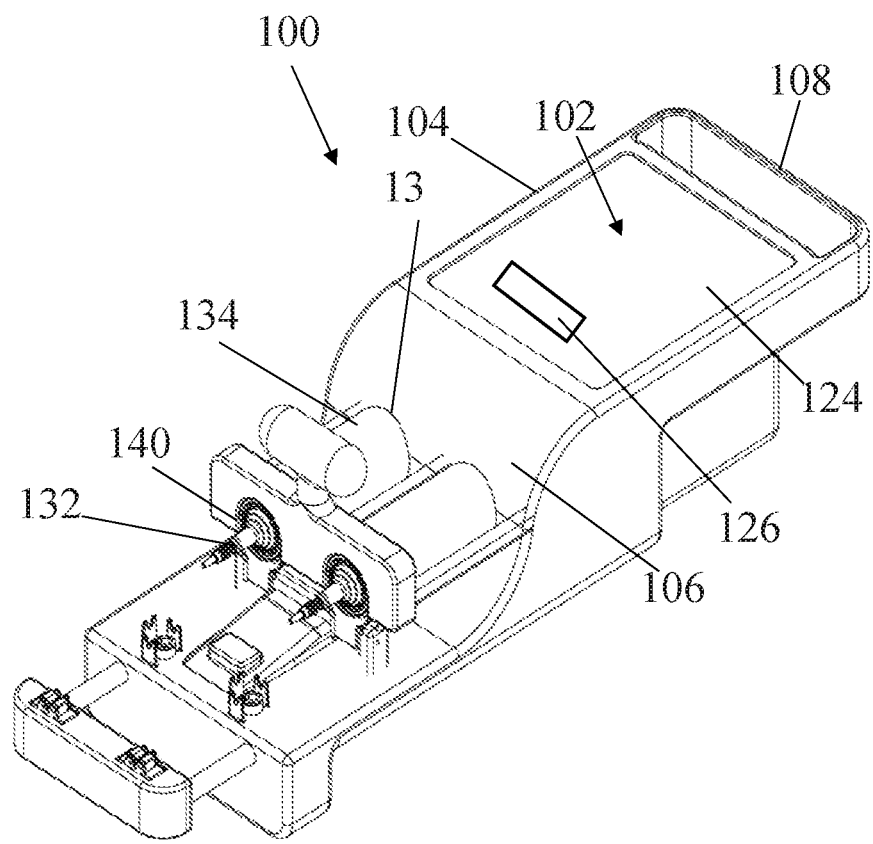
FIG. 1 is a perspective view of a fluid injector configured for use in a multi-fluid delivery system, according to one example or aspect of the present disclosure.

As used herein, the singular form of "a", "an", and "the" include plural referents unless the context clearly dictates otherwise.

Spatial or directional terms, such as "left", "right", "inner", "outer", "above", "below", and the like, relate to the invention as shown in the drawing figures and are not to be considered as limiting as the invention can assume various alternative orientations.

All numbers used in the specification and claims are to be understood as being modified in all instances by the term "about". The term "about" is meant to include plus or minus twenty-five percent of the stated value, such as plus or minus ten percent of the stated value. However, this should not be considered as limiting to any analysis of the values under the doctrine of equivalents.

Unless otherwise indicated, all ranges or ratios disclosed herein are to be understood to encompass the beginning and ending values and any and all subranges or sub-ratios subsumed therein. For example, a stated range or ratio of "1 to 10" should be considered to include any and all subranges or sub-ratios between (and inclusive of) the minimum value of 1 and the maximum value of 10; that is, all subranges or sub-ratios beginning with a minimum value of 1 or more and ending with a maximum value of 10 or less. The ranges and/or ratios disclosed herein represent the average values over the specified range and/or ratio.

The terms "first", "second", and the like are not intended to refer to any particular order or chronology, but refer to different conditions, properties, or elements.

All documents referred to herein are "incorporated by reference" in their entirety.

The term "at least" is synonymous with "greater than or equal to".

The term "not greater than" is synonymous with "less than or equal to".

As used herein, "at least one of" is synonymous with "one or more of". For example, the phrase "at least one of A, B, and C" means any one of A, B, or C, or any combination of any two or more of A, B, or C. For example, "at least one of A, B, and C" includes A alone; or B alone; or C alone; or A and B; or A and C; or B and C; or all of A, B, and C.

The term "includes" is synonymous with "comprises".

When used in relation to a syringe, for example, a rolling diaphragm syringe, the term "proximal" refers to a portion of a syringe nearest a piston element for engaging with an end wall of the syringe and delivering fluid from a syringe. When used in relation to a fluid path, the term "proximal" refers to a portion of the fluid path nearest to an injector system when the fluid path is connecting with the injector system. When used in relation to a syringe, the term "distal" refers to a portion of a syringe nearest to a delivery nozzle. When used in relation to a fluid path, the term "distal" refers to a portion of the fluid path nearest to a patient when the fluid path is connected with an injector system. The term "radial" refers to a direction in a cross-sectional plane normal to a longitudinal axis of a syringe extending between proximal and distal ends. The term "circumferential" refers to a direction around an inner or outer surface of a sidewall of a syringe. The term "axial" refers to a direction along a longitudinal axis of the syringe extending between the proximal and distal ends.

It is to be understood, however, that the disclosure may assume alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the examples disclosed herein are not to be considered as limiting.

Referring to the drawings in which like reference characters refer to like parts throughout the several views thereof, the present disclosure is generally directed to a medical injector/injection system 100 (hereinafter "fluid injector system 100") for example an injector system including one or more syringes, including front-loading syringes and rolling diaphragm-type syringes. However, the various methods and protocols of the present disclosure may be utilized or incorporated into other syringe-based injector systems.

With reference to FIG. 1, the fluid injector system 100 includes multiple components as individually described herein. Generally, the fluid injector system 100 has a powered injector administrator or device configured to move various components of the injector during an injection protocol and operated by at least one processor and a fluid delivery set intended to be associated with the powered injector to take in and deliver one or more fluids from one or more fluid reservoirs under pressure into a patient. The various devices, components, and features of the fluid injector system 100 and the fluid delivery set associated therewith are likewise described in detail herein according to a non-limiting embodiment. In one example, a fluid injector system 100 may include at least one fluid reservoir, such as syringe 132, at least one piston (not shown) having an interface that is reversibly connectable to a plunger of the syringe, and a fluid control module (not pictured). Embodiments and features of suitable syringes are described in U.S. Provisional Application Ser. No. 63/073,519, filed 2 Sep. 2020, the disclosure of which is incorporated herein by this reference. The at least one syringe 132 is generally adapted to interface with at least one component of the system, such as a syringe port 13 and/or a pressure jacket 134. The fluid injector system 100 is generally configured to deliver at least one fluid to a patient during an injection procedure, such as an angiography injection procedure. The fluid injector system 100 is configured to releasably receive the at least one syringe 132, which is to be filled with at least one fluid, such as an imaging contrast media, saline solution, Ringer's lactate, or any desired medical fluid, supplied by a fluid source through a fluid line. The system may be a multi-syringe injector, wherein two or more syringes may be oriented side-by-side or other spatial relationship and are separately actuated by respective pistons associated with the injector. The at least one syringe 132 may be oriented in any manner such as upright, downright, or positioned at any degree angle.

With continued reference to FIG. 1, the injector system 100 may be used during a medical procedure to inject the at least one medical fluid into the vasculature system of a patient by driving a plunger of at least one syringe 132 with a drive member, such as the at least one piston (not shown). The at least one piston may be reciprocally operable upon at least a portion of the at least one syringe 132, such as the plunger. Upon engagement, the at least one piston may move the plunger toward the distal end 140 of the at least one syringe 132, as well as retracting the plunger toward the proximal end of the at least one syringe 132. The syringe 132 extends along a longitudinal axis. The fluid line may also be connected in fluid communication to an outlet port of each syringe 132 to place each syringe 132 in fluid communication with a bulk fluid reservoir for filling each syringe 132 with a medical fluid and/or a catheter for delivering the fluid from each of syringes 132 to the catheter (not shown) inserted into a patient at a vascular access site.

In various examples, the syringe retention features of the present disclosure may be suited for use in single or dual syringe-type front-loading fluid injector systems, such as are disclosed in U.S. Pat. Nos. 5,383,858, 7,553,294, 7,563,249, 7,666,169, 8,945,051, 9,173,995, 9,199,033, 9,474,857, and 10,124,110, U.S. patent application Ser. Nos. 15/305,285, 15/541,573, and 15/568,505, and in PCT Application Publication Nos. WO 2016/191485; WO 2016/112163; and WO 2020/055785, the disclosures of which are incorporated herein by reference in their entireties.

With reference to FIG. 1, the fluid injector system 100 (also referred to as "the injector") includes an injector housing 102 having opposed lateral sides 104, a distal or upper end 106, and a proximal or lower end 108. The housing 102 encloses the various mechanical drive components, electrical and power components necessary to drive the mechanical drive components, and control components, such as electronic memory and electronic control devices (hereinafter electronic control device(s)), used to control operation of reciprocally movable piston elements associated with the fluid injector system 100 described herein including communication with a controller or processor.

With reference to FIG. 1, embodiments of the fluid injector system 100 may include one or more user interfaces 124, such as a graphical user interface (GUI) display window or touch screen, and/or one or more buttons and readouts. The user interface 124 may display information pertinent to a fluid injection procedure involving the fluid injector system 100, such as current flow rate, fluid pressure, and volume remaining in the fluid sources 21 connected to the fluid injector system 100. In certain embodiments, the one or more user interfaces 124 may be at least one touch screen GUI that allows an operator to input commands and/or data for operation of the fluid injector system 100. While the user interface 124 is shown on the injector housing 102, interface 124 may also be in the form of or include an additional remote display that is wired or wirelessly linked to the housing 102 and electrical control devices and mechanical elements of the fluid injector system 100. In some aspects, the user interface 124 may be a tablet computer that is detachably connected to the housing 102 and is in wired or wirelessly linked communication with the housing 102. The fluid injector system 100 may further include one or more processors in electronic communication with and configured to control one or more functions of the fluid injector system 100. Additionally, the fluid injector system 100 and/or user interface 124 may include at least one control button 126 for tactile operation by an attendant operator of the fluid injector system 100, such as a button for engaging and disengaging the syringe retention features described herein. In certain aspects, the at least one control button 126 may be part of a keyboard for inputting commands and/or data by the operator. The at least one control button 126 may be hard-wired or wirelessly connected to the electronic control device(s) associated with the fluid injector system 100 to provide direct input to the electronic control device(s). The at least one control button 126 may also be graphically part of the user interface 124, such as a touch screen. In either arrangement, the at least one control button 126 desirably provides certain individual control features to the attendant operator of the fluid injector system 100, such as but not limited to: (1) filling/purging of the fluid injector system 100; (2) inputting information and/or data related to the patient and/or injection procedure, and (3) initiating/stopping an injection procedure. The user interface 124 and/or any electronic processing units associated with the fluid injector system 100 may be wired or wirelessly connected to an operation and/or data storage system such as a hospital network system.

As used herein, the electronic control device includes a processor to, or is operable to, execute appropriate custom-designed or conventional software to perform and implement the processing steps of the embodiments of the methods and systems of the present disclosure, thereby forming a specialized and particular computing system. Accordingly, the presently-disclosed methods and systems may include one or more electronic control devices or similar computing devices having a computer-readable storage medium capable of storing computer-readable program code or instructions that cause the processing unit to execute, configure, or otherwise implement the methods, processes, and transformational data manipulations discussed hereinafter in connection with the present disclosure. Still further, the electronic control device may be in the form of a computer, a personal digital assistant, a portable computer, a laptop, a palmtop, a mobile device, a mobile telephone, a server, or any other type of computing device having the necessary processing hardware to appropriately process data to effectively implement the presently-disclosed computer-implemented method and system. In one example, the electronic control devices may be housed in the user interface 124 and corresponding processor.

The present disclosure is directed to syringe and pressure jacket retention features particularly for angiography (CV) injectors. Contrast enhanced angiography involves injection of fluid through a catheter to the heart. Due to the viscosity of the contrast agent, high flow rates, and small diameter of the catheter, angiography injections can involve high pressures up to 1200 psi. Under such high pressures, conventional plastic syringes used in contrast enhanced computed tomography, which includes pressures up to 300 psi, may experience excessive radial expansion of the syringe wall which can result in undesired changes in fluid delivery volumes and flow rates or potentially even structural failure. To counter this, pressure jackets with thick walls or walls of stronger materials have been developed to limit the radial expansion of the pressurized syringes. CV injectors must be designed to engage with and retain not only with the syringe but also the corresponding pressure jacket surrounding at least a portion of the sidewall of the syringe. The present disclosure describes various embodiments of retention mechanisms to interface a pressure jacket and/or syringe with a CV fluid injector.

For example, according to various embodiments, the present disclosure describes assemblies for retaining a pressure jacket and a syringe on a CV fluid injector. The syringe and pressure jacket may interface with a base plate of the fluid injector where the base plate may include a body. The assembly may include one or more retaining arms protruding distally from the base plate and having a retaining surface at a distal end thereof for abutting and engaging a distal end of the pressure jacket and/or syringe. In certain embodiments, the assembly may include at least a first retaining arm and a second retaining arm operatively mounted on the body of the base plate. The first retaining arm may have a first retaining surface at a distal end thereof and the second retaining arm may have a second retaining surface at a distal end thereof, where the first retaining surface and the second retaining surface are configured for abutting a distal surface of at least one of the pressure jacket and the syringe. The assembly may further include a linkage assembly operatively connected to one or both of the first retaining arm and the second retaining arm. The linkage assembly may be configured for moving at least one of the first retaining arm and the second retaining arm between at least a first open position and a closed position. The first and second retaining arms may each comprise at least one and in certain embodiments, two longitudinal supports connecting opposite sides of the base plate to opposite sides of the corresponding retaining surface. The two first longitudinal supports of the first retaining arm may be connected and move in concert around commonly aligned first pivot points. The two second longitudinal supports of the second retaining arm may be connected and move in concert around commonly aligned and second pivot points.

In certain embodiments, the linkage assembly may be operatively connected to a proximal end of the first retaining arm and a proximal end of the second retaining arm. For example, the linkage assembly may operatively connect the first retaining arm to the second retaining arm such that the first retaining arm and the second retaining arm are configured to move in unison between at least the first open position and the closed position. Alternatively, the linkage assembly may operatively connect the first retaining arm to the second retaining arm such that the first retaining arm and the second retaining arm are configured to move individually between at least the first open position and the closed position. In certain embodiments, the first retaining arm and the second retaining arm are connected to the body of the base plate at a first pivot point and a second pivot point, respectively, so that the first retaining arm and the second retaining arm pivot between at least the first open position and the closed position about the first pivot point and the second pivot point.

In a first open position, the first retaining surface of the first retaining arm and the second retaining surface of the second retaining arm are separated from one another at a first distance configured to permit insertion and engagement of at least one of the pressure jacket and the syringe with the fluid injector or removal of at least one of the pressure jacket and the syringe from the fluid injector. In certain embodiments, in the first open position the distance between the first retaining surface and the second retaining surface may be wide enough to allow insertion and engagement of the syringe into the pressure jacket and removal of the syringe from the pressure jacket and the retention assembly, but not allow insertion/engagement and removal of the pressure jacket from the retention assembly. In other embodiments, in the first open position the distance between the first retaining surface and the second retaining surface may be wide enough to allow insertion and engagement of the syringe into the pressure jacket and removal of the syringe from the pressure jacket and the retention assembly, and also be sufficiently wide to allow insertion/engagement and removal of the pressure jacket from the retention assembly, either concurrent with insertion/removal of the syringe or in a separate operation.

In the closed position, the first retaining surface of the first retaining arm and the second retaining surface of the second retaining arm may be separated from one another at a second distance to retain the pressure jacket and the syringe between the first retaining arm and the second retaining arm. For example, in the closed position the first retaining surface of the first retaining arm and the second retaining surface of the second retaining arm may be held in a position where the first retaining surface abuts the second retaining surface to retain the syringe and the pressure jacket in the retention assembly, for example during a pressurized fluid delivery procedure. In certain embodiments, the first retaining surface and the second retaining surface may be arcuate or semi-circular in shape and, when in the closed, abutting position, may form at least a partial circular retaining surface for engaging with and retaining the distal end of the syringe and the distal end of the pressure jacket. According to various embodiments, the first distance between the first retaining arm and the second retaining arm may be greater than the second distance.

In various embodiments, the first retaining arm and the second retaining arm may pivot between at least an intermediate, second open position about the first pivot point and the second pivot point. In the second open position, first retaining surface of the first retaining arm and the second retaining surface of the second retaining arm are separated from one another at a third distance to retain the pressure jacket in the fluid injector and allow insertion and removal of the syringe from the pressure jacket and allow engagement and disengagement of the syringe with the fluid injector. In particular, in the second open position the distance between the first retaining surface and the second retaining surface may be wide enough to allow insertion and engagement of the syringe into the pressure jacket and removal of the syringe from the pressure jacket and the retention assembly, but not allow insertion/engagement and removal of the pressure jacket from the retention assembly. According to these embodiments, the first position first distance is greater than the second distance and the third distance is less than the first distance and greater than the second distance.

In various embodiments, the first retaining surface of the first retaining arm comprises a first syringe retaining surface and a first pressure jacket retaining surface and the second retaining surface of the second retaining arm comprises a second syringe retaining surface and a second pressure jacket retaining surface. The first and second syringe retaining surfaces and/or the first and second pressure jacket retaining surfaces may include one or more protrusions for engaging the syringe and/or pressure jacket, respectively.

In certain embodiments, the first retaining surface of the first retaining arm and the second retaining surface of the second retaining arm may each include at least one inner protrusion to engage a distal end of at least one of the pressure jacket and the syringe. In certain embodiments, the first retaining surface and the second retaining surface include an inner syringe retaining protrusion to engage a circular load bearing wall at the distal end of the syringe. The syringe retaining protrusion may be at least partially circumferential and extend proximally from each of the retaining surfaces and include a proximal surface at an angle relative to a longitudinal axis of the syringe and having an innermost, at least partial circumference that extends more proximal than the outermost at least partial circumference creating the angled proximal surface. The angled proximal surface may be configured to interact with a corresponding oppositely angled surface of the circumferential load bearing wall on a distal end of the syringe. The complementary angled surfaces interact under the distally directed pressure on the syringe associated with a fluid injection procedure to urge the distal ends of the first retaining arm and the second retaining arm with an inward retaining force. That is, the angled surface of the syringe circumferential load bearing wall is urged in the distal direction when the syringe is pressurized and creates an inward radial force on the corresponding complementary angled surface of the syringe retaining protrusion to urge the first retaining surface and first retaining arm towards the second retaining surface and second retaining arm with an inward retaining force to help retain the first and second retaining arms in the closed position under fluid injection pressure.

According to various embodiments, the first retaining surface of the first retaining arm and the second retaining surface of the second retaining arm may each include at least one pressure jacket protrusion to engage a distal end of the pressure jacket. For example, the pressure jacket protrusion may form a circumferential groove in the proximal surface of the first and second retaining surfaces that interacts with and provides a slot into which the distal end of the pressure jacket may insert and be retained. The first and second retaining surfaces may include one or more engagement slots, tabs, or other features which interact with corresponding tabs, slots, or features on the distal end of the pressure jacket to engage and retain the pressure jacket when the retaining assembly is in the closed position, for example to prevent the pressure jacket from sliding laterally out of alignment with the engagement arms.

According to various embodiments, the linkage assembly may comprise at least one biasing member configured for biasing the first retaining arm and the second retaining arm to move in unison between at least the first open position and the closed position, and in certain embodiments between the intermediate second open position. The biasing member may include multiple biasing members, such as springs, that bias the first retaining arm into the first open position and may work with a first biasing plate, to bias the first retaining arm into the closed position. Likewise, the second retaining arm may include more than one biasing members, such as springs, that bias the second retaining arm into the first open position and may work with a second biasing plate, to bias the first retaining arm into the closed position.

According to various embodiments, at least one of the first retaining arm and the second retaining arm may include at least one finger tab configured to assist in moving the first retaining arm and the second retaining arm between the closed position and the first and/or second open positions. The one or more finger tabs may be arranged on the first and second retaining arms to allow the user to manually open and/or close the first and second retaining arms so that a syringe and/or pressure jacket can be inserted or removed from the retention assembly. In certain embodiments, each longitudinal support of the first retaining arm and each longitudinal support of the second retaining arm may each include one finger tab.

In other embodiments, the assembly and/or the fluid injector may include an electromechanical motor provided in the injector housing to move the first retaining arm and the second retaining arm between the first open position and the closed position. According to specific embodiments, the electromechanical motor may further move the first retaining arm and the second retaining arm to the intermediate second open position.

Figure 2A:
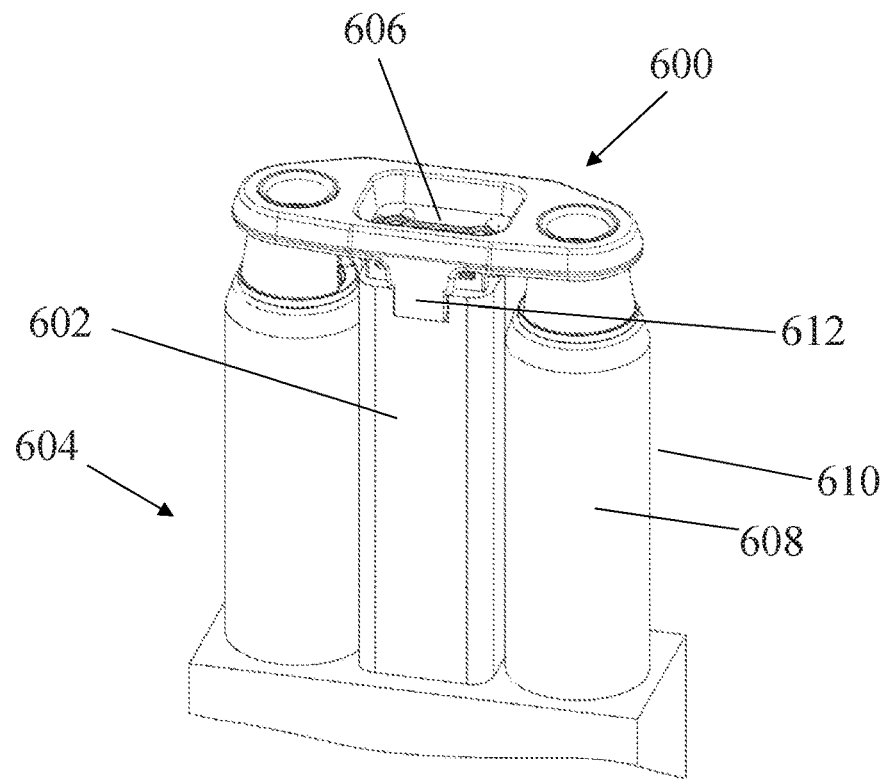
FIGS. 2A and 2B illustrate a hinged retaining element for a CV application according to various embodiments.
Figure 2B:
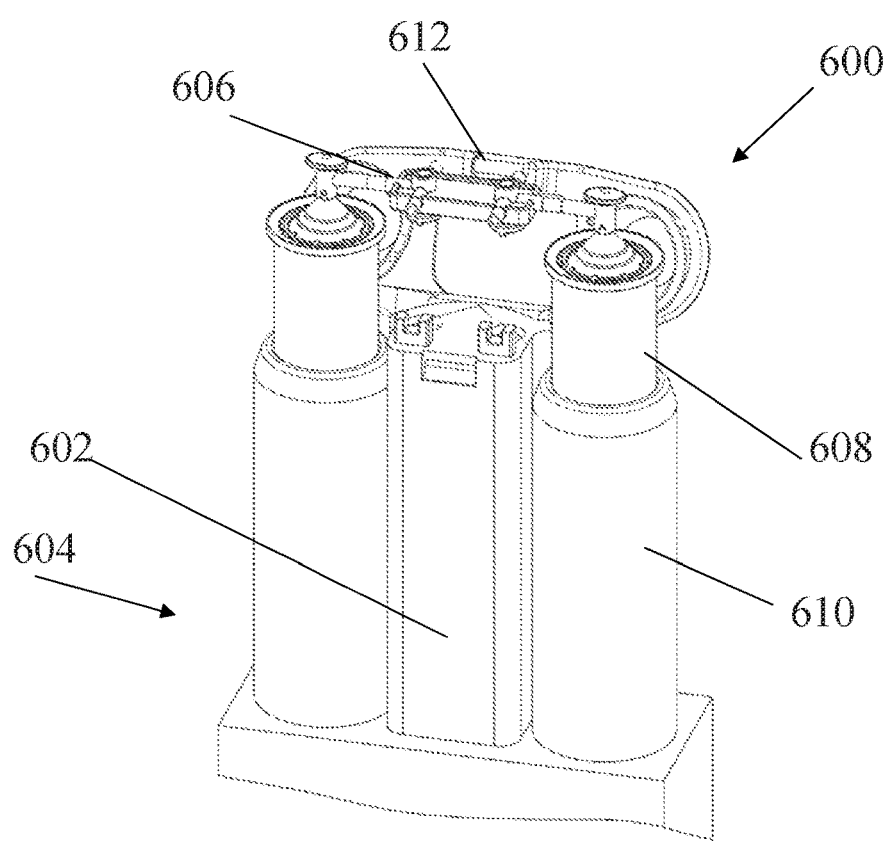

FIGS. 2A and 2B illustrate a retaining element 600 according to various embodiments that is attached to a central support 602 of the CV fluid injector 604 by a hinged mechanism 606 that can move between an open position (FIG. 2B) where at least one syringe 608 may be inserted into the pressure jacket assembly 610, and a closed position (FIG. 2A) where the at least one syringe 608 is fixedly retained within the pressure jacket assembly 610 for a fluid delivery process. In various embodiments, the retaining element 600 may include a rotatable plate member that is rotatable between the open position and the closed position. The retaining element 600 may be locked in the closed position using a snap tab feature 612 to prevent the retaining element 600 from moving to the open position during use of the CV fluid injector 604. In various embodiments, other locking mechanisms may be utilized to hold the retaining element 600 in the closed position.

Figure 3A:
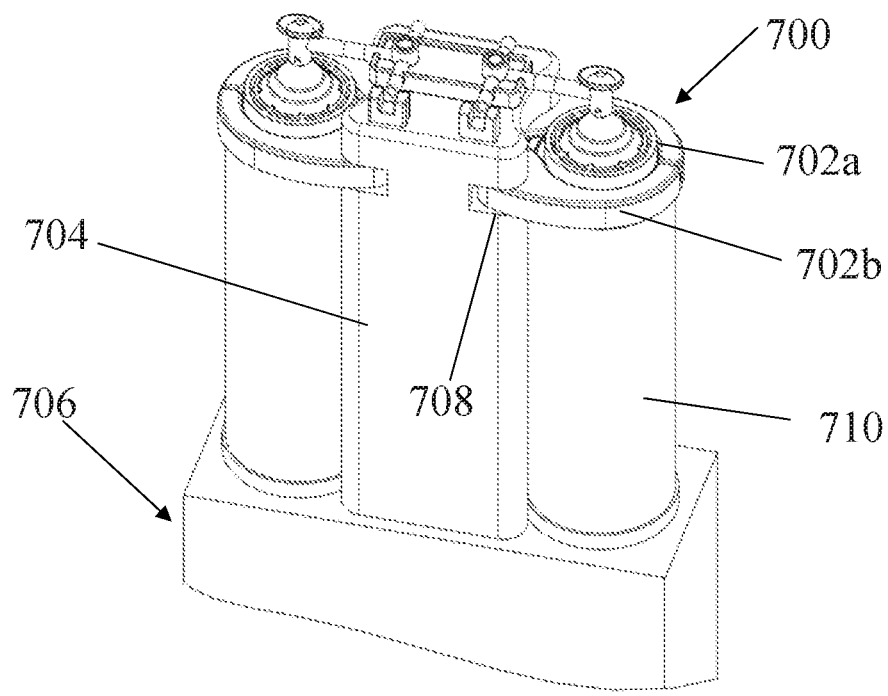
FIGS. 3A and 3B illustrate a pivot clamp retaining element for a CV application according to various embodiments.
Figure 3B:
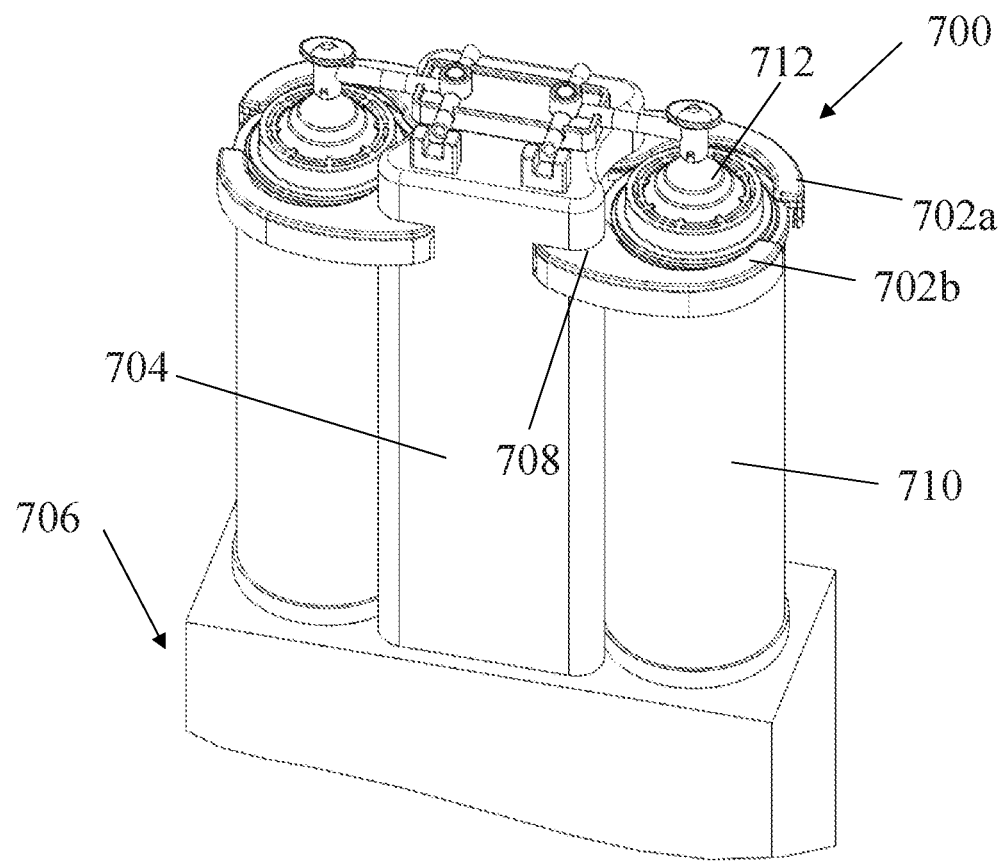

FIGS. 3A and 3B illustrate a retaining element 700 according to various embodiments where the retaining element 700 comprises two or more arms 702a, 702b that are attached to a central support 704 of the CV fluid injector 706 by pivoting mechanisms 708. The retaining elements 700 may move between an open position (FIG. 3B) where at least one syringe 710 may be inserted into or removed from the pressure jacket assembly 712, and a closed position (FIG. 3A) where the at least one syringe 710 is fixedly retained within the pressure jacket assembly 712 for a fluid delivery process. The pivoting mechanisms 708 may be manually actuated by an operator, for example by moving a lever or other activation assembly, or may be automatically moved by a motor assembly (not illustrated). The pivoting mechanisms 708 are configured such that, in the closed position, the retaining elements 700 create a clamping force and a downward force on a distal end of one or both of the syringe 710 and the pressure jacket assembly 712 to prevent one or both of the syringe 710 and the pressure jacket assembly 712 from moving during operation of the CV fluid injector 706.

Figure 4A:
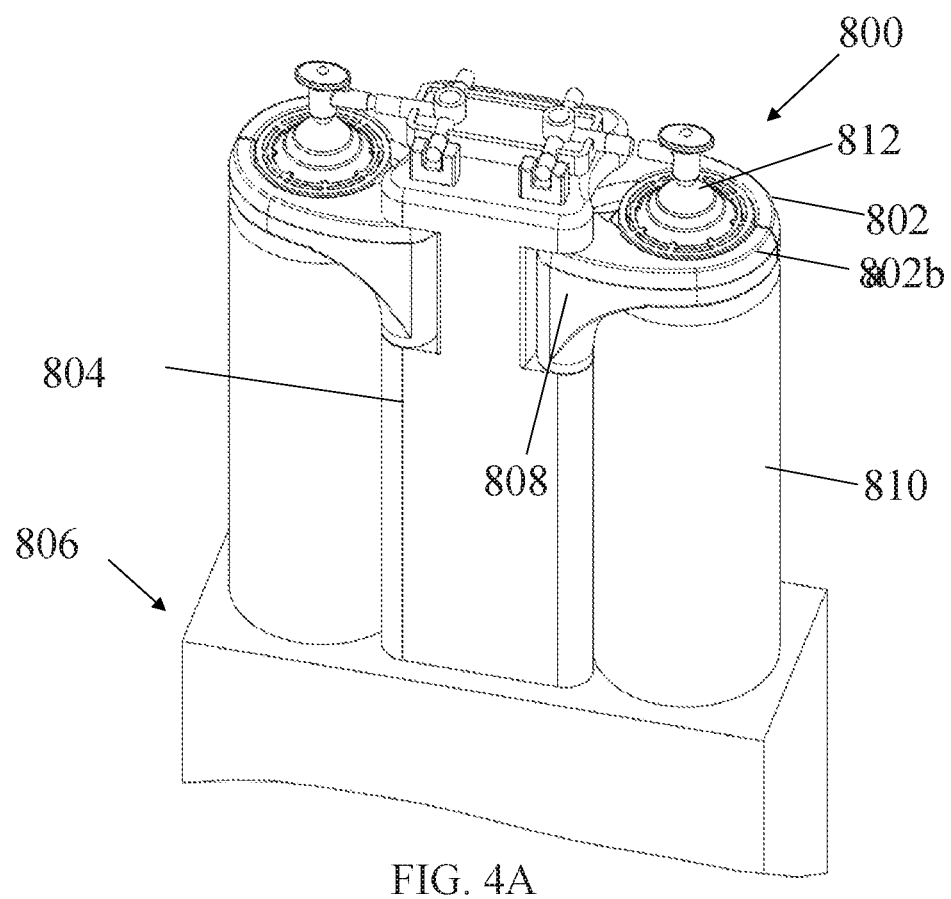
FIGS. 4A, 4B, and 4C illustrate another pivot clamp retaining element for a CV application according to various embodiments.
Figure 4B:
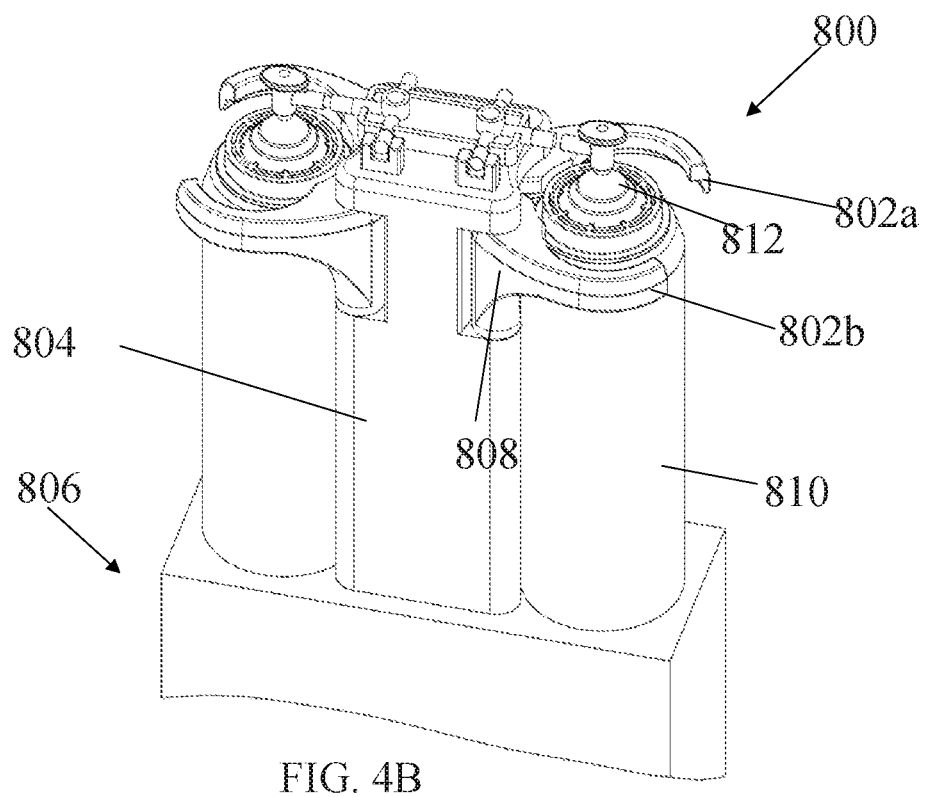
Figure 4C:
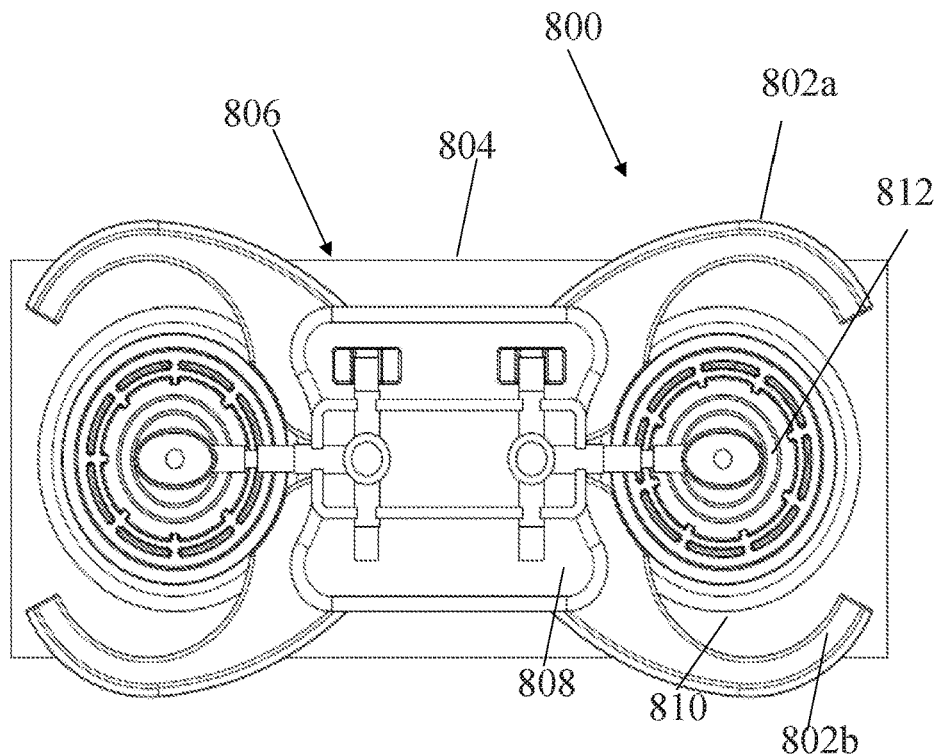

FIGS. 4A, 4B and 4C illustrate a retaining element 800 according to an embodiment similar to that described in FIGS. 3A and 3B where the retaining element 800 comprises two or more arms 802a, 802b that are attached to a central support 804 of the CV fluid injector 806 by a pivoting mechanisms 808. The retaining elements 800 may move between a first open position (top view in FIG. 4C) where the at least one syringe 810 and a pressure jacket assembly 812 may be inserted into or removed from the assembly, a second open position where the at least one syringe 810 may be inserted into or removed from the pressure jacket assembly 812 (FIG. 4B), and a closed position (FIG. 4A) where the at least one syringe 810 and the pressure jacket assembly 812 are fixedly retained within the retaining element 800 for a fluid delivery process. The pivoting mechanisms 808 may be manually actuated by an operator or may be automatically moved by a motor assembly (not illustrated). The pivoting mechanisms 808 are configured such that, in the closed position, the retaining elements 800 create a clamping force and a downward force on a distal end of one or both of the syringe 810 and the pressure jacket assembly 812 to prevent one or both of the syringe 810 and the pressure jacket assembly 812 from moving during operation of the CV fluid injector 806. The embodiment of FIGS. 4A, 4B and 4C differs from that of FIGS. 3A and 3B at least in the distance that the two or more arms 802a, 802b pivot to allow the syringe 810 and/or pressure jacket assembly 812 to be inserted into or removed from the fluid injector 806.

Figure 5A:
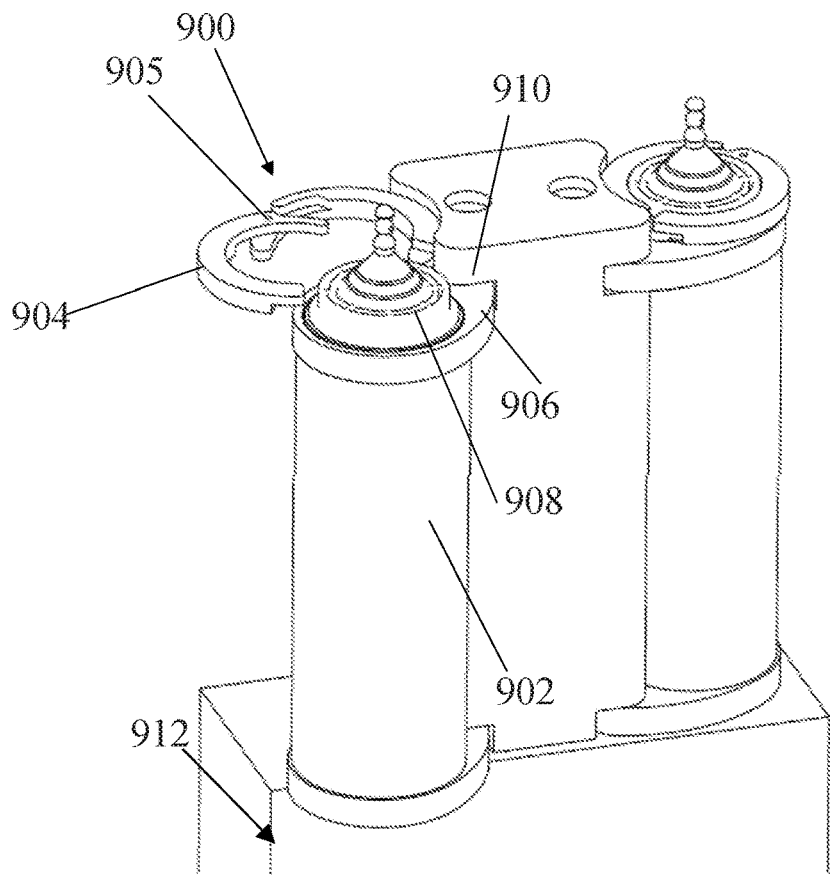
FIGS. 5A and 5B illustrate a retaining element for a CV application having a rotatable pressure jacket according to various embodiments.
Figure 5B:
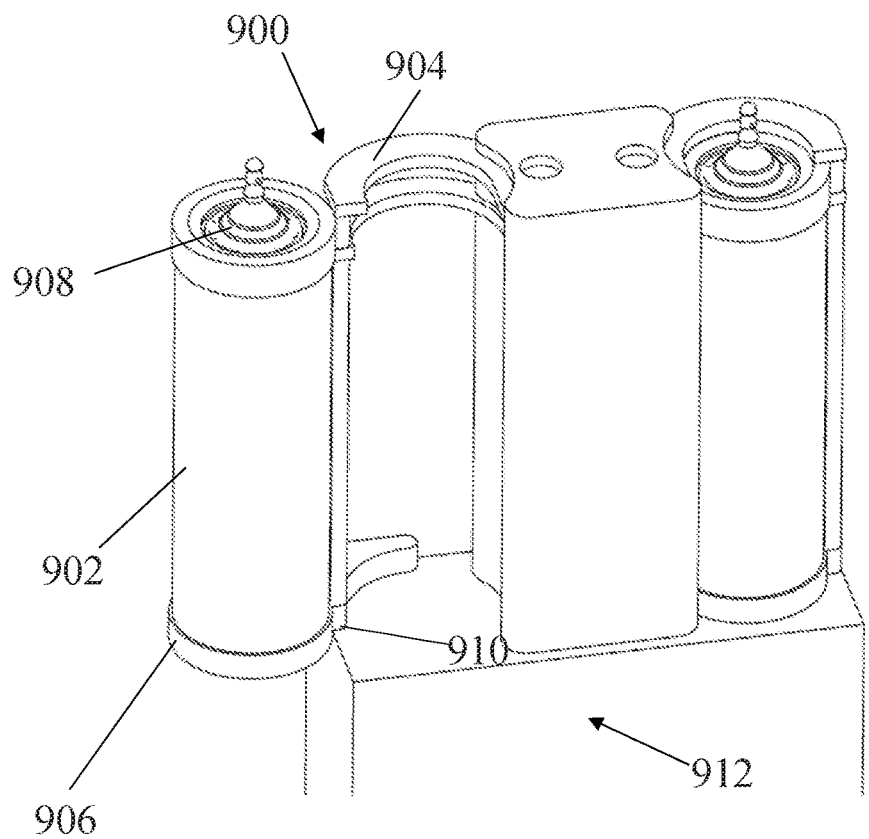
Figure 6A:
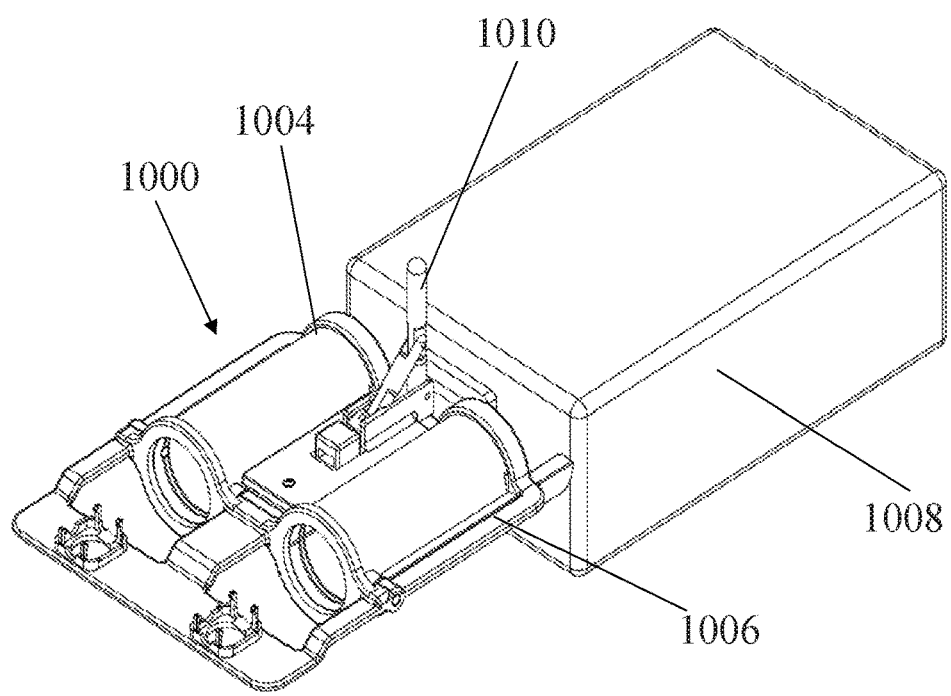
FIGS. 6A to 6E illustrate a retaining element for a CV application having breach loading according to various embodiments.
Figure 6B:
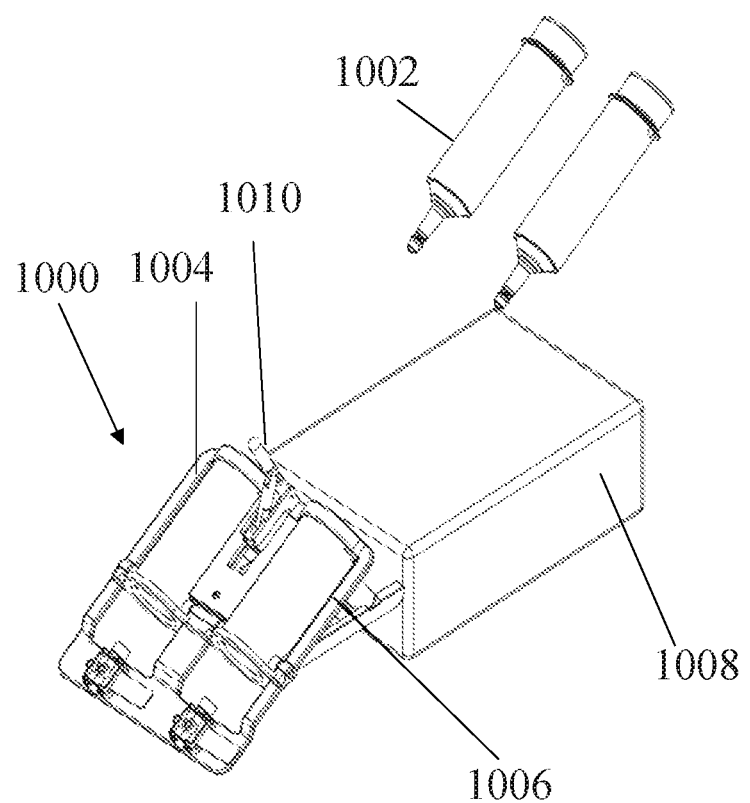
Figure 6C:
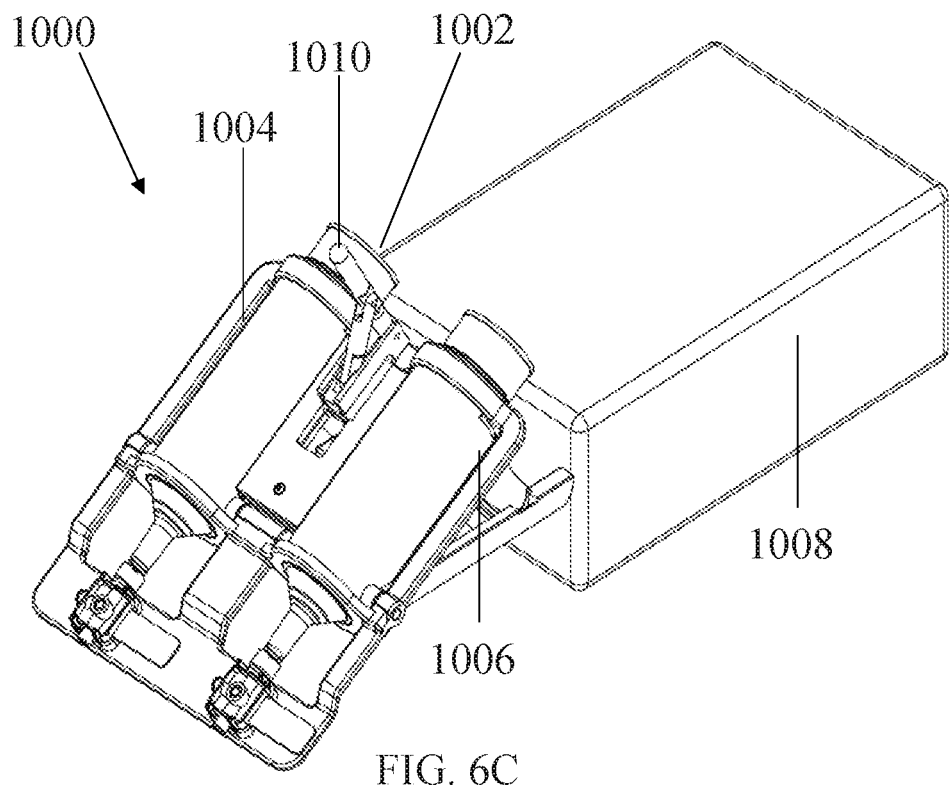
Figure 6D:
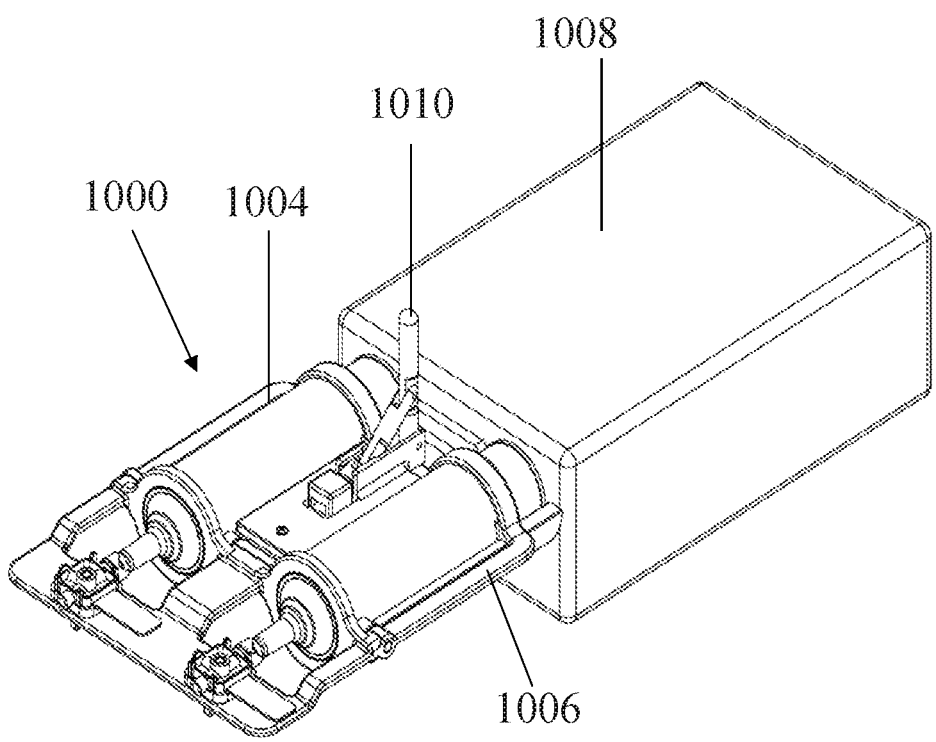
Figure 6E:
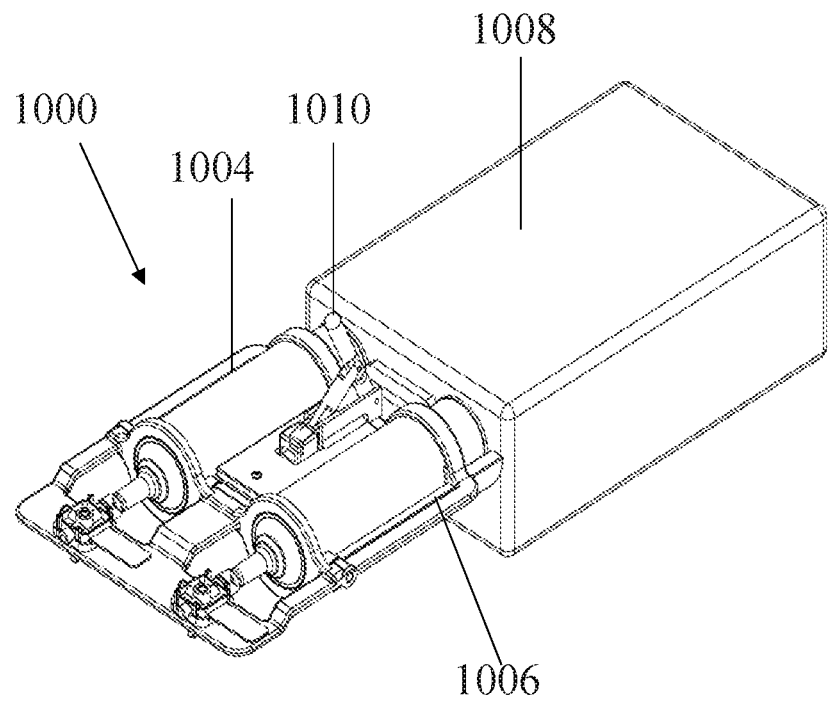
Figure 7A:
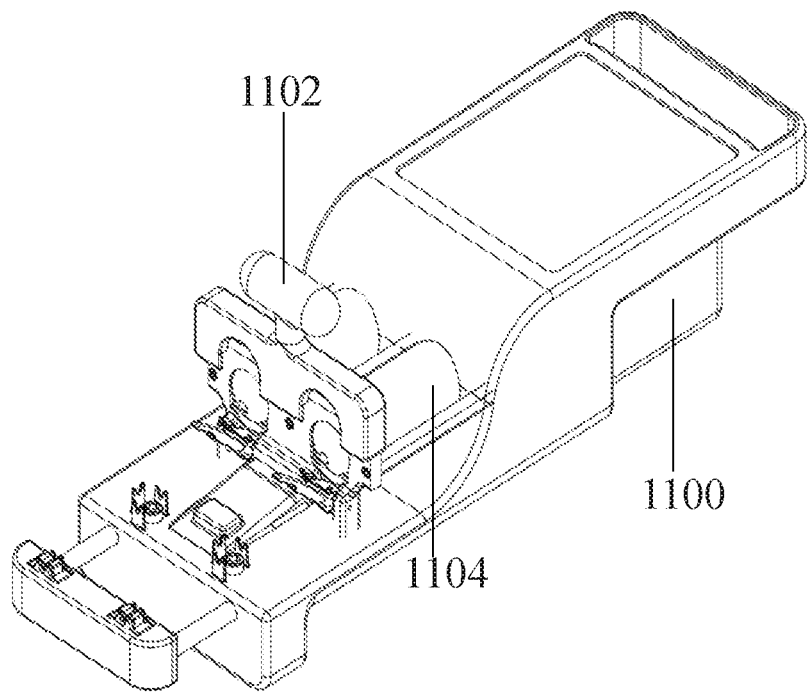
FIGS. 7A to 7D illustrate a front loading sliding retaining element for a CV application according to various embodiments.
Figure 7B:
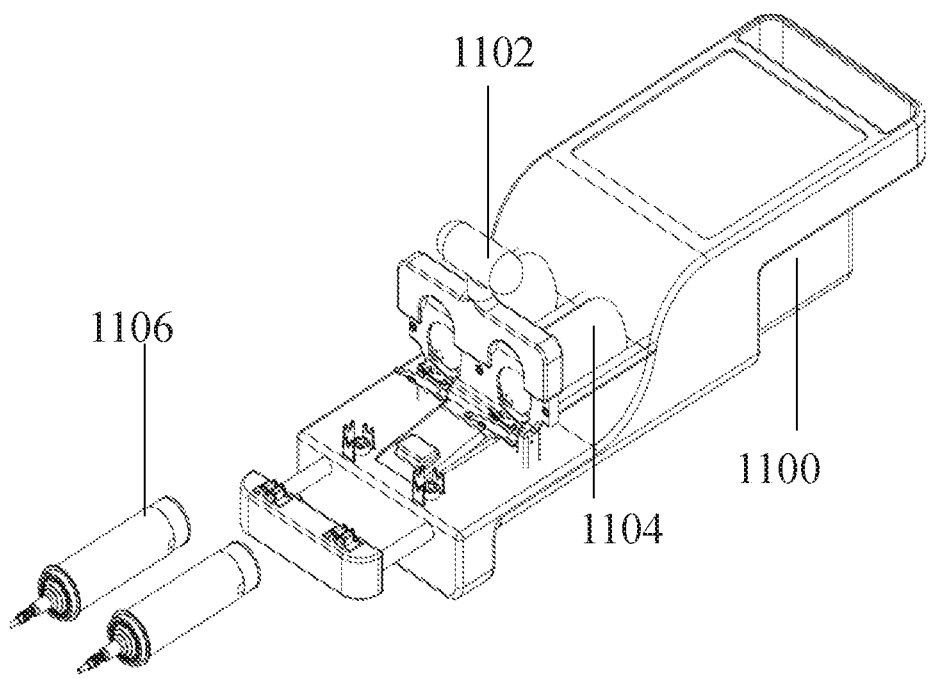
Figure 7C:
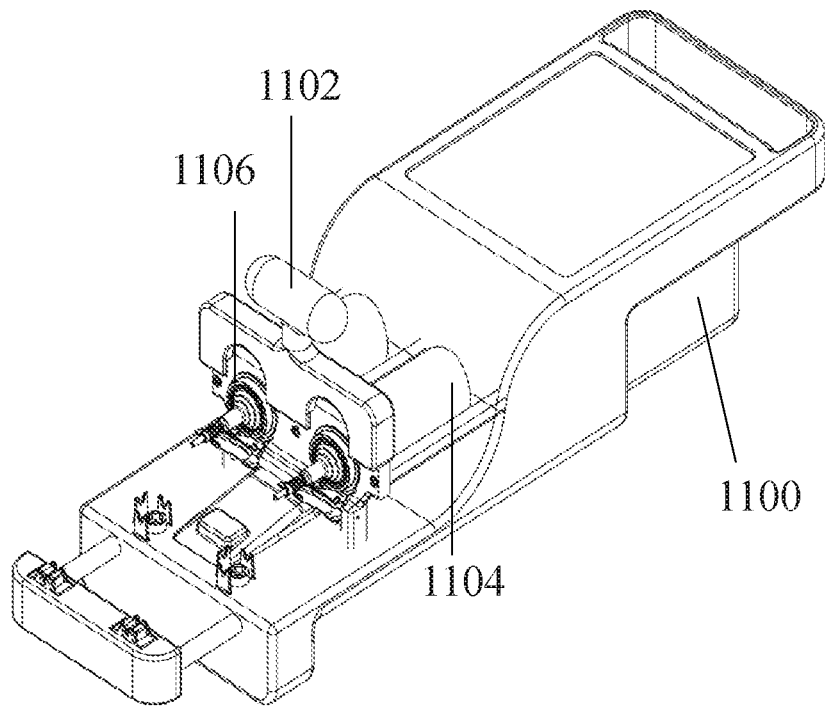
Figure 7D:
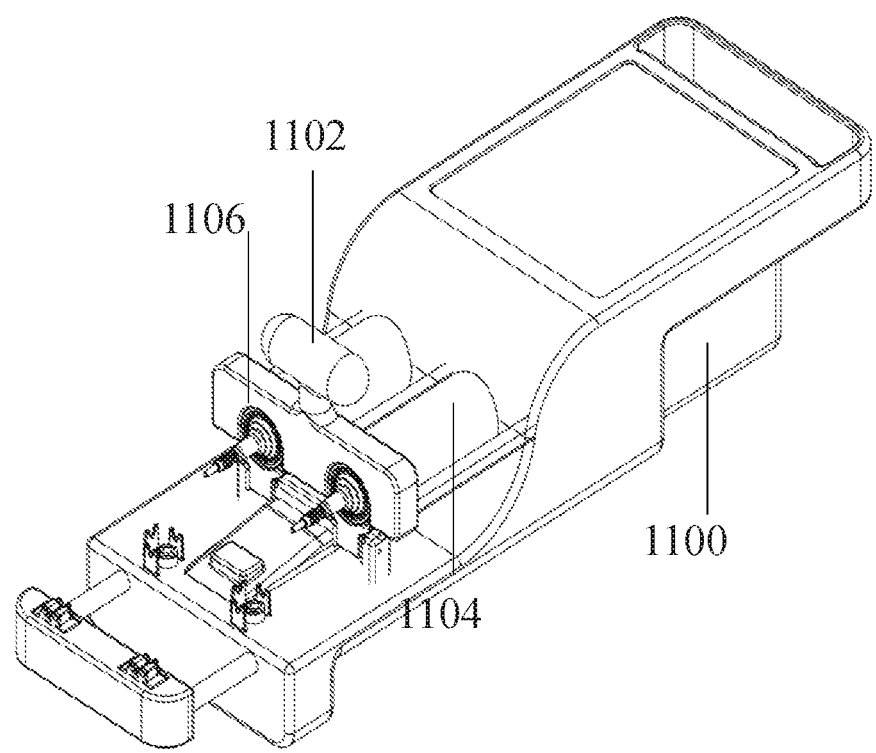

FIGS. 5A and 5B illustrate an embodiment of a retaining element 900 for a CV application having a rotatable pressure jacket 902 on a rotatable retainer assembly 906 according to various embodiments. In FIG. 5A, both a portion of a retaining arm 904 and a retainer assembly 906 holding the pressure jacket 902 and syringe assembly 908 rotate around respective pivot points 905, 910 to allow insertion and removal of the pressure jacket 902 and syringe assembly 908 from the retaining fixture. As shown in FIG. 5A, the retaining arm 904 and retainer assembly 906 may pivot in opposite directions. In FIG. 5B, an embodiment in which a retainer assembly holding the pressure jacket 902 and syringe 908 rotates the syringe 908 and pressure jacket 902 into and out of engagement with a fixed retaining surface of the retaining element 900. The retainer assembly 906 is independently rotatable relative to the CV fluid injector 912 to move the syringe 908 and pressure jacket 902 away from and towards the CV fluid injector 912. When the retainer assembly 906 is rotated into a docked position (shown in right-hand side of FIG. 5B), the retaining arm 904 can be rotated into engagement with the syringe 908 and pressure jacket 902 in the retainer assembly 906 to retain the syringe 908 and pressure jacket 902 within the CV fluid injector 912. The retaining arm 904 may include one or more elements for retaining the syringe 908 and pressure jacket 902 assembly. The retainer assembly 906 may be manually moved, for example, using arm 910, to pivot retainer assembly 906 between the open and closed position. Alternatively, a motor associated with fluid injector 912 may be used to move retainer assembly 906 between the open and closed positions.

FIGS. 6A to 6E illustrate an embodiment of a retaining element 1000 for a CV application having breach loading of the syringe 1002 according to various embodiments. In contrast to conventional front loading syringe based injectors, according to this embodiment, the syringe 1002 is loaded into the pressure jackets 1004 by a breach loading mechanism 1006 where the proximal end of the pressure jacket 1004 pivots upwardly (see FIGS. 6B and 6C) or downwardly to allow insertion of the at least one syringe 1002 into the proximal end of the pressure jacket 1004. Subsequently, the pressure jackets 1004 are pivoted back to the plane of the injector 1008 (see FIG. 6D) and locked in place by a locking mechanism 1010 (see FIG. 6E) so that the fluid injector pistons may engage the syringe 1002. In certain embodiments, the pressure jacket 1004 may include a distal cap (not shown) having a shape that is complementary to the distal end of the syringe 1002. For example, the distal cap may be conical to engage a conical distal end of the syringe 1002. The cap may be unitary with the pressure jacket 1004 or may be attachable to the distal end of the pressure jacket 1004. In other embodiments, the distal cap may be installed on the distal end of the syringe 1002 prior to insertion into the breach of the pressure jacket 1004 so that the outer circumference of the distal cap engages an inner ledge on an inside surface of distal end of the pressure jacket 1004.

FIGS. 7A to 7D illustrate an embodiment for a CV fluid injector 1100 having front loading with a slidable retaining element 1102 according to various embodiments. The slidable retaining element 1102 is configured to slide upwardly (see FIG. 7A) or downwardly (see FIG. 7D) relative to the longitudinal axis of the pressure jackets 1104 to allow access to the distal end of the pressure jackets 1104 so that syringes 1106 may be inserted therein or removed therefrom (see FIGS. 7B and 7C). After syringe insertion, the slidable retaining element 1102 is slid into the closed position and locked in place to retain the syringes 1106 in the pressure jacket 1104 (see FIG. 7D). Fluid tubing components 1108 may then be attached to the fluid outlet at the distal end of the syringes 1106.

Figure 8A:
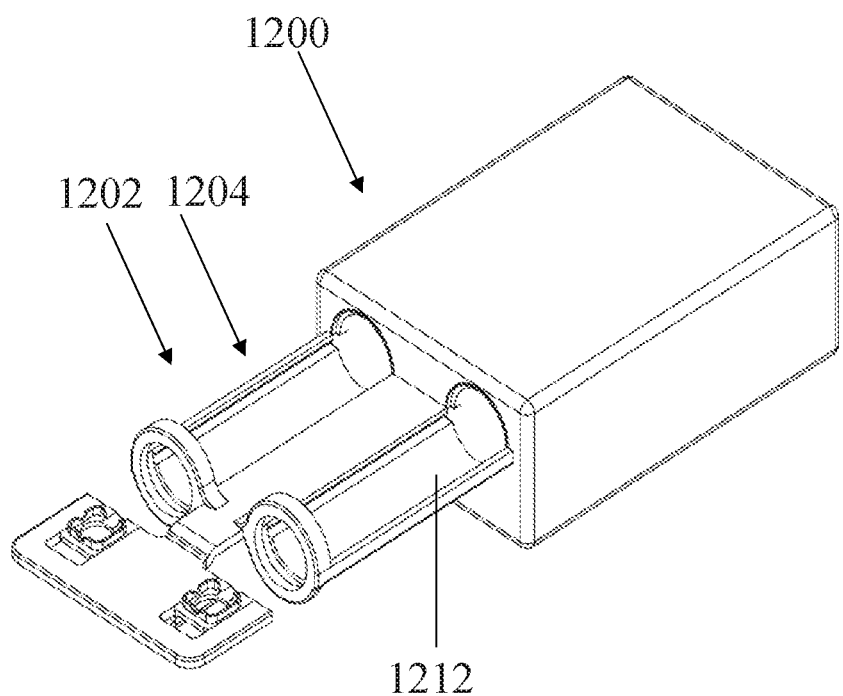
FIGS. 8A to 8E illustrate a fixed retaining element and two-piece pressure jackets for a CV application according to various embodiments.
Figure 8B:
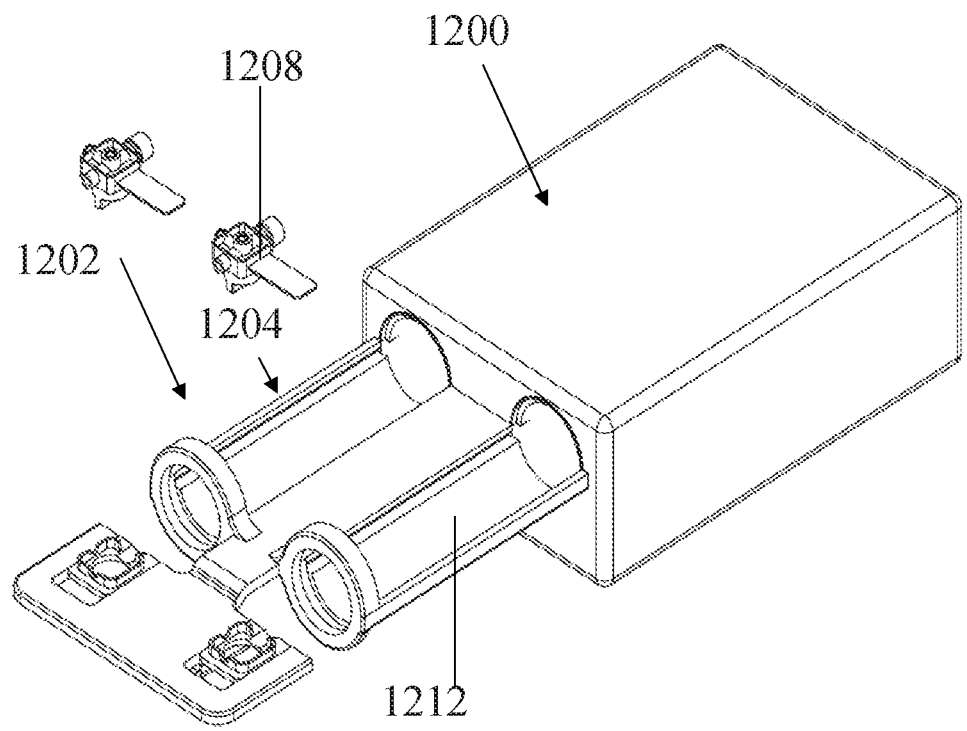
Figure 8C:
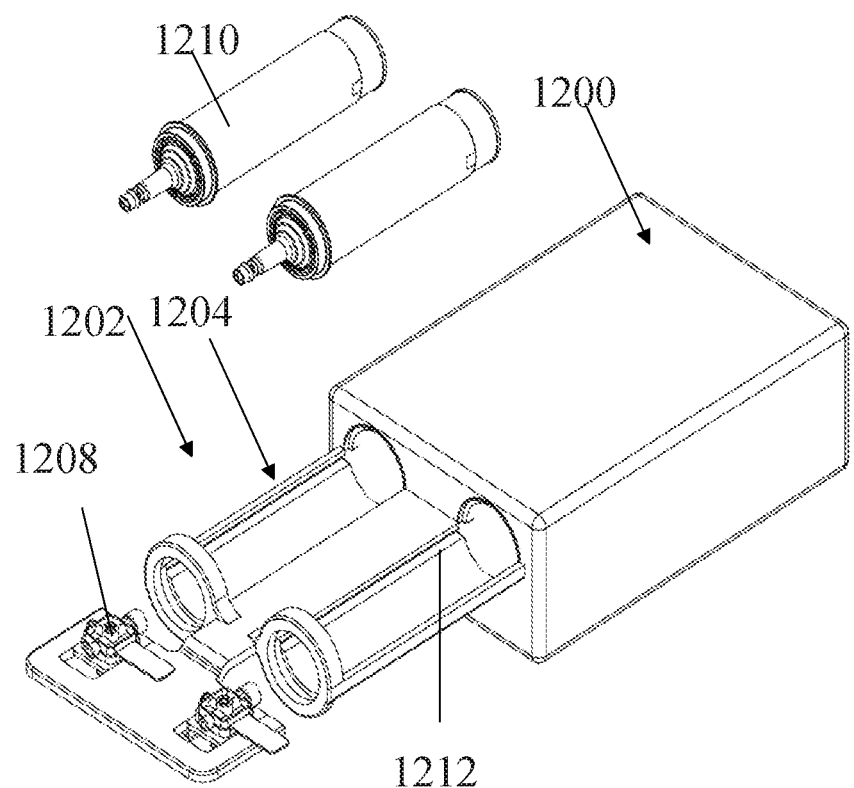
Figure 8D:
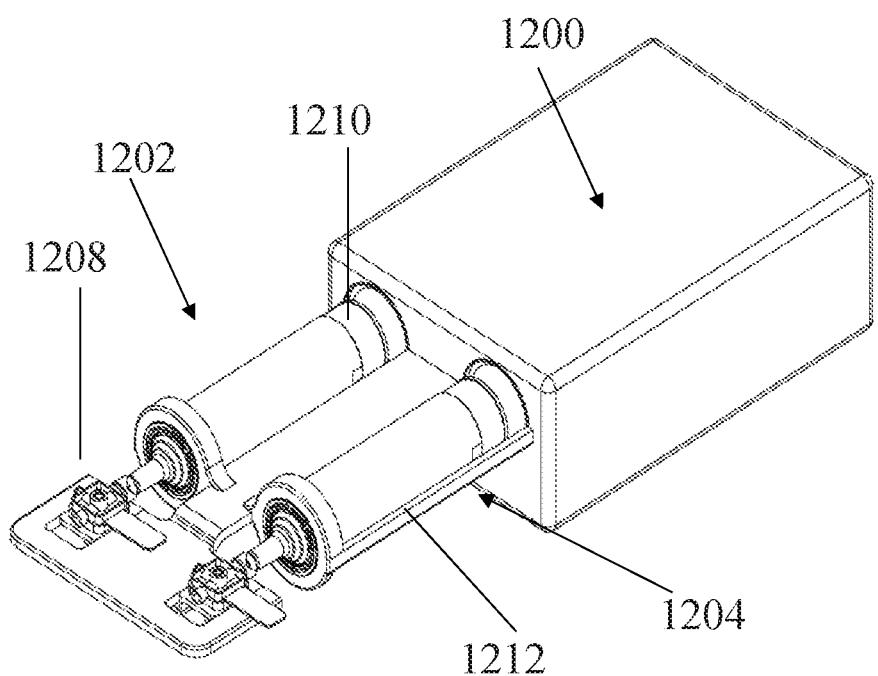
Figure 8E:
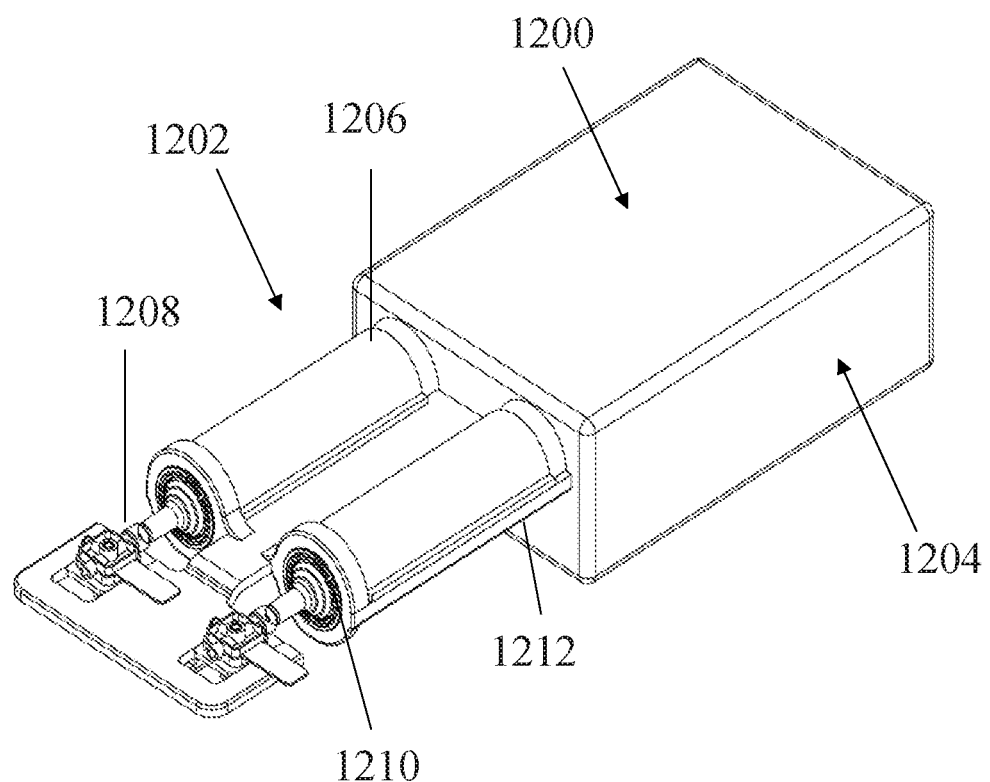

FIGS. 8A to 8E illustrate an embodiment of a CV fluid injector 1200 having a fixed retaining element 1202 (see FIG. 8A) and a two-piece pressure jacket 1204 according to various embodiments (see FIG. 8E). According to this embodiment, the upper portion 1206 of the pressure jacket 1204 may be removed, fluid path components 1208 and valving is installed (FIG. 8B) and the syringe 1210 is inserted into the lower pressure jacket assembly 1212 (FIGS. 8C and 8D). The upper portion 1206 of the pressure jacket 1204 may then be reinstalled (FIG. 8E) and the system prepared for the fluid delivery process, for example by attaching fluid path components 1208. The upper portion 1206 of the pressure jacket 1204 may engage a retention surface at a distal end of the lower pressure jacket assembly 1212 and an engagement feature on the port of the fluid injector 1200 for example, when the syringe is pressurized and urged in the distal direction by a piston.

Figure 9A:
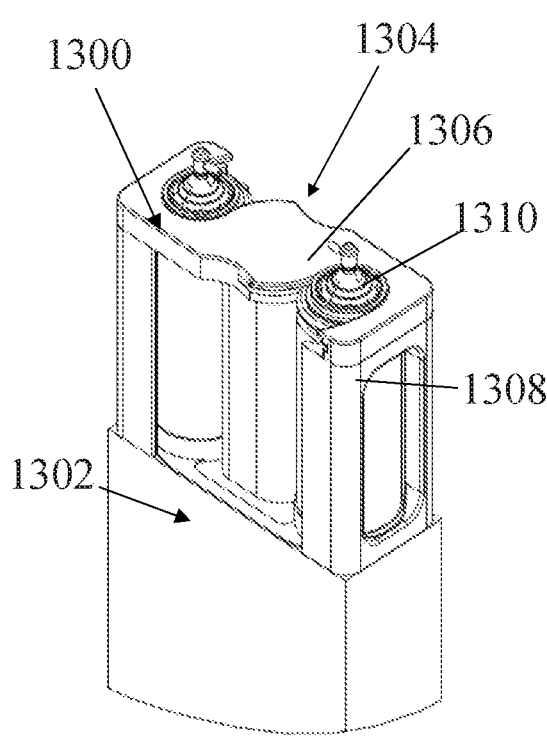
FIGS. 9A and 9B illustrate a rotating retaining element for a CV application having hinged pressure jacket retention features according to various embodiments.
Figure 9B:
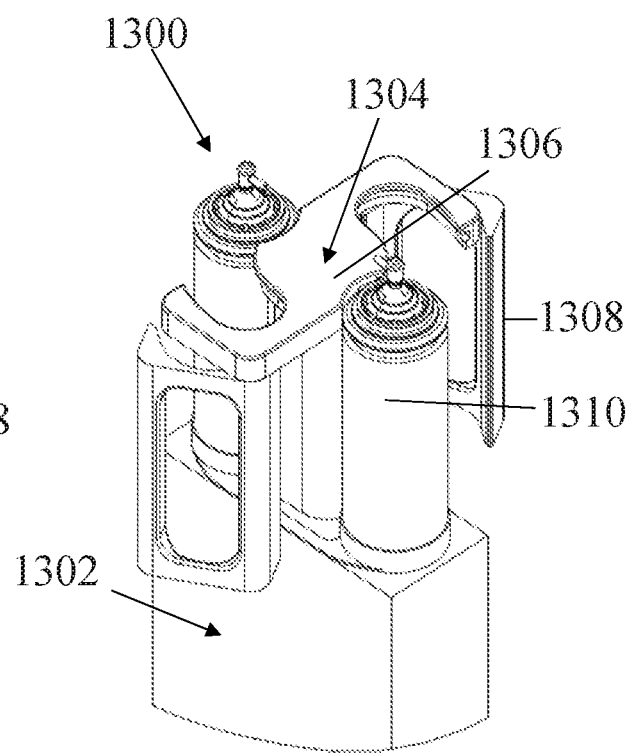

FIGS. 9A and 9B illustrate an embodiment of a rotating retaining element 1300 for allowing access to a pressure jacket/syringe assembly 1310 of a CV fluid injector 1302 having hinged pressure jacket retention features 1304 according to various embodiments. FIG. 9A illustrates the retaining member/pressure jacket assembly 1304 in the closed and locked position. In FIG. 9B, the retaining member/pressure jacket assembly 1304 is shown in the open position where the top plate 1306 of the assembly 1304 rotates up to 90 degrees and a hinged pressure jacket cover 1308 is pivoted to access the pressure jacket/syringe assembly 1310 for insertion or removal.

Figure 10A:
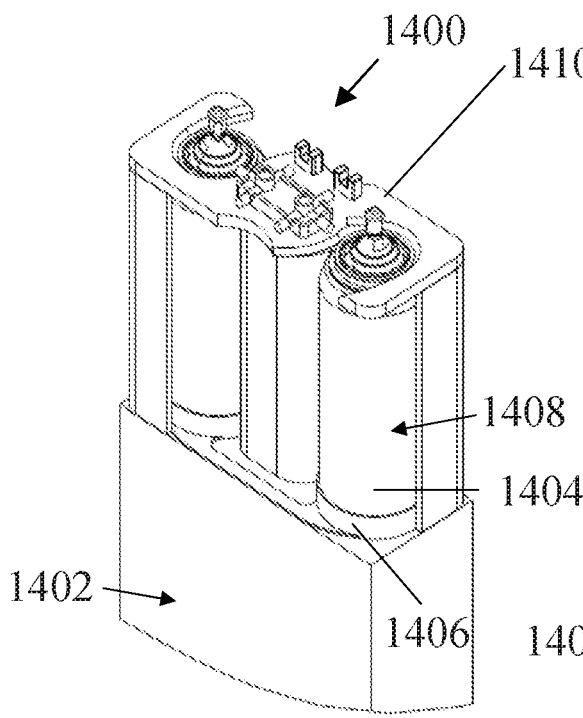
FIGS. 10A and 10B illustrate a retaining element for a CV application having pressure jackets on a rotatable plate according to various embodiments.
Figure 10B:
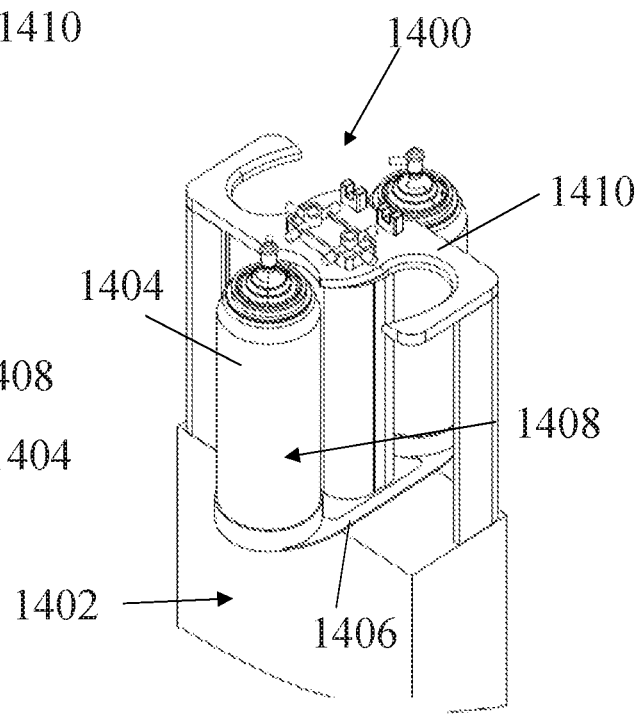

FIGS. 10A and 10B illustrate an embodiment of a retaining element 1400 for a CV fluid injector 1402 having pressure jackets 1404 on a rotatable plate 1406 according to various embodiments. The pressure jacket and syringe assembly 1408 is retained on a rotatable proximal plate 1406 that rotates between a closed position (FIG. 10A) where a distal end of the pressure jacket and syringe assembly 1408 is engaged with a distal retaining plate 1410 and an open position (FIG. 10B) where the rotatable proximal plate 1406 is rotated up to 90 degrees to disengage the pressure jacket and syringe assembly 1408 from the distal retaining plate 1410. After rotation to the open position, the pressure jacket and syringe assembly 1408 may be inserted or removed from the CV fluid injector 1402.

FIGS. 11A to 11I illustrate an embodiment of a fluid injector head with a breech-loading pressure jacket and rotating pressure jacket engagement arm 1500. The pressure jacket engagement arm 1500 includes an opening 1502 through which a pressure jacket 1504 may be loaded when the pressure jacket engagement arm 1500 is loaded. The pressure jacket engagement arm 1500 may include a pressure jacket retention mechanism (see, e.g., FIGS. 13A-E and 14A-F) to releasably retain the pressure jacket 1504 within the pressure jacket engagement arm 1500. The rotating pressure jacket engagement arm 1500 may rotate from an open position (shown in FIG. 11A) to an engaged position (shown in FIG. 11C) around a pivot point 1506 (see FIG. 11B). The rotating pressure jacket engagement arm 1500 may be manually rotated by a user or may be automatically rotated by the fluid injector operating system, for example after a user presses a button or other activation mechanism on the fluid injector system or after the fluid injector senses that a syringe 1508 has been located into the pressure jacket 1504. In other embodiments, the pressure jacket engagement arm 1500 may slide between the open position and the engaged position.

Figure 11A:
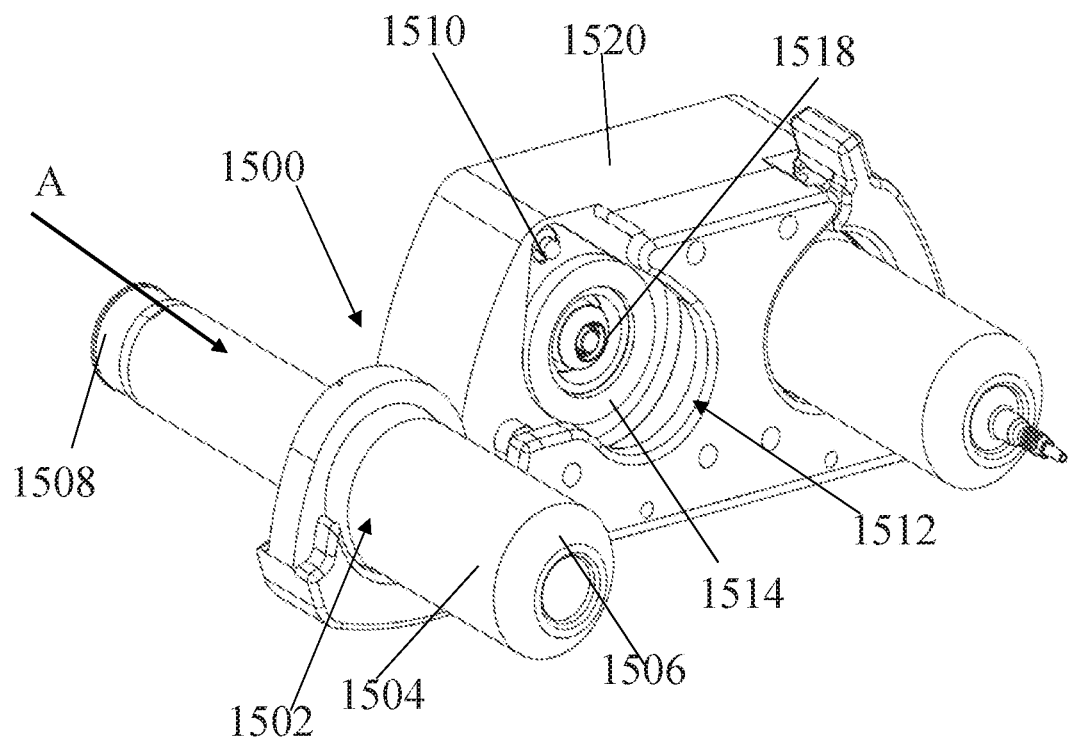
FIGS. 11A to 11I illustrate a fluid injector front plate having a 3-position breech loading pressure jacket carriage configuration according to one embodiment.
Figure 11B:
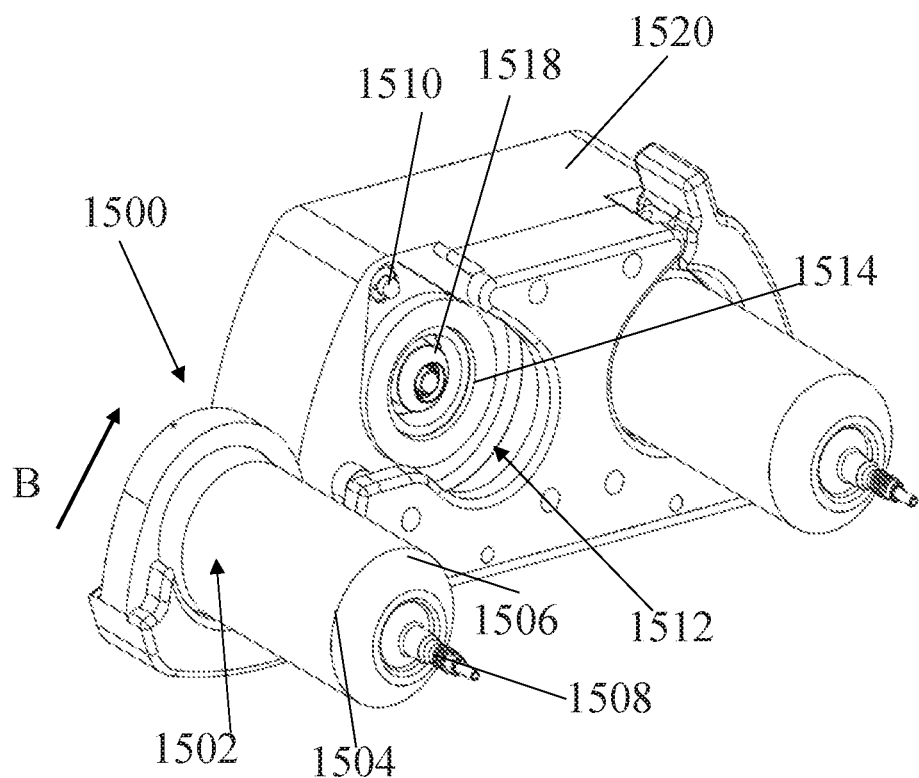
Figure 11C:
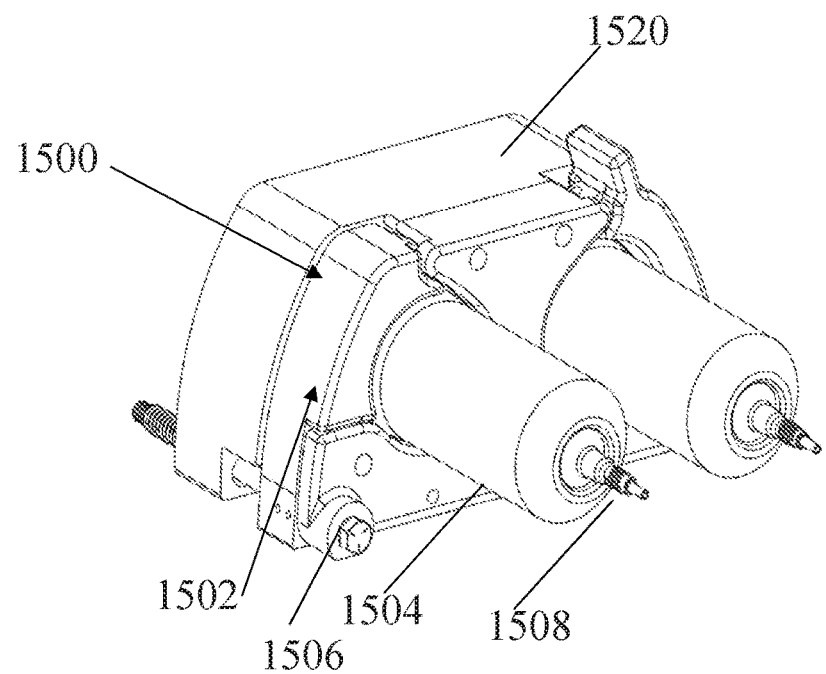

In the open position, a syringe 1508 may be loaded into the pressure jacket 1504 by a breech loading process, see FIG. 11A. As used herein, the term "breech loading" means that the syringe 1508 is inserted into the proximal open end of the pressure jacket 1504, as shown by arrow A of FIG. 11A, for example until the distal tip and fluid delivery port of the syringe 1508 protrude from a distal opening of the pressure jacket 1504. According to these embodiments, the pressure jacket 1504 may include a circumferential side wall that has an inner diameter that is slightly larger than the outer diameter of the side wall of the syringe 1508 and may include a partially closed distal end having an inner wall that covers a portion of the distal end of the pressure jacket 1504 and has an inner surface that has a shape that is complementary to a shape of the outer surface of the distal end of the syringe 1508. For example, in one embodiment, the distal ends of the pressure jacket 1504 and the syringe 1508 may have complementary conical distal ends. In other embodiments, a portion of the distal end of the syringe 1508 may include an outer surface perpendicular to the longitudinal axis of the syringe 1508 which engages an inner surface of the distal end of the pressure jacket 1504 that is perpendicular to the longitudinal axis of the pressure jacket 1504. Once the syringe 1508 is loaded into the pressure jacket 1504, the pressure jacket engagement arm 1500 may be rotated as shown by arrow B in FIG. 11B to the engaged position FIG. 11C. The pressure jacket engagement arm 1500 may be held in the engaged position, for example by a latching mechanism or detent mechanism 1510.

Figure 11D:
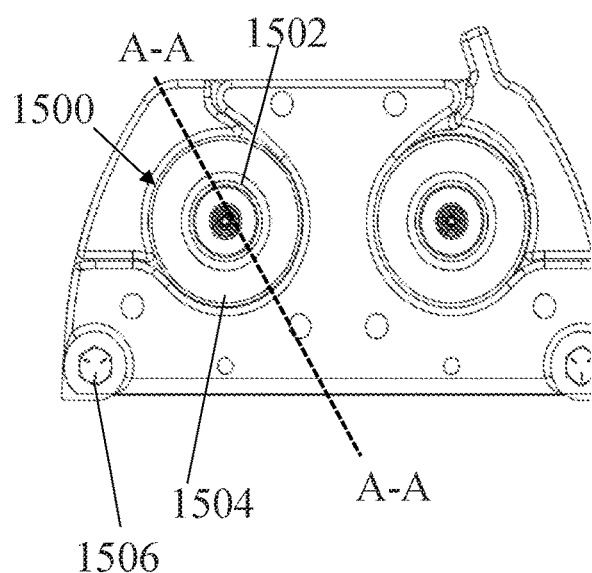
Figure 11E:
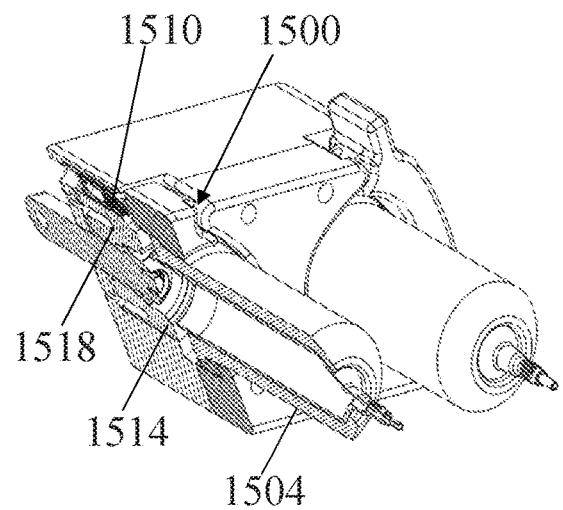
Figure 11F:
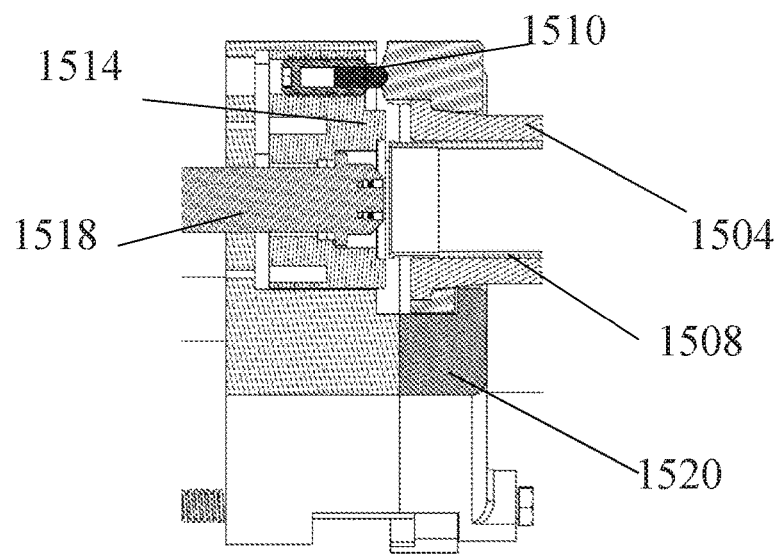

FIG. 11D illustrates a front view of the fluid injector pressure jacket retention mechanism according to embodiments of the present disclosure in the engaged position. FIG. 11E illustrates a cross-section side perspective along line A-A of the fluid injector carriage operation according to an embodiment.

According to embodiment illustrated in FIGS. 11A to 11I, the assembly may include three carriage positions when the pressure jacket engagement arm 1500 is in the engaged position during a fill or injection procedure. Various features of the interface between the fluid injector port 1512 and the rotating pressure jacket engagement arm 1500 when in the engaged position is illustrated in cross-sectional view of FIG. 11F. Features of the interface include a carriage 1514 on an axial slide, a detent or latch 1510 for releasably locking the pressure jacket engagement arm 1500 in the engaged position, a plunger interface 1518 which is attached by a piston to a ball screw or other drive implementation mechanism, a frame 1520 on the proximal end of the fluid injector, a pressure jacket 1504 and the syringe 1508 within the pressure jacket 1504.

Figures 11G, 11H, 11I:
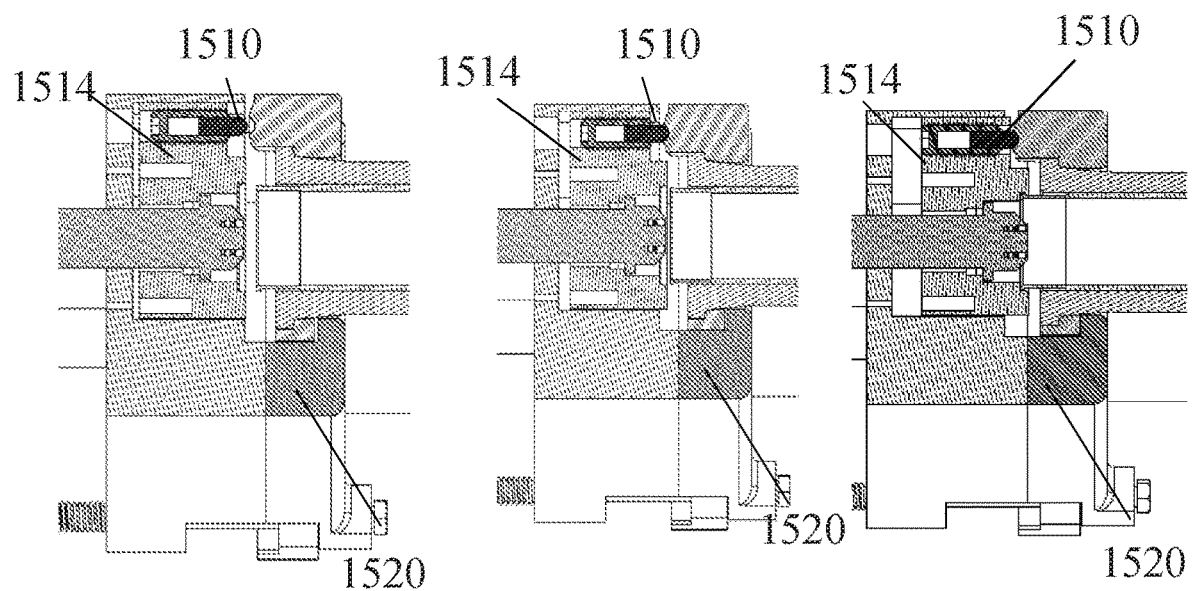

Operation of these features is shown in the three carriage positions illustrated in FIGS. 11G, 11H, and 11I. In FIG. 11G, the detent or latch 1510 is initially in the disengaged position to allow rotation of the pressure jacket engagement arm 1500 from the open position to the engaged position. To facilitate the rotation into the engaged position, the fluid injector carriage apparatus 1514 is in a first disengaged position and there is clearance between the rotating pressure jacket engagement arm 1500 and the frame 1520 of the fluid injector. The clearance between the carriage apparatus 1514 and the pressure jacket/syringe features with the pressure jacket engagement arm 1500, shown in FIG. 11H, results in mechanical slack between the components of the injector, the pressure jacket 1504, and the syringe 1508. Once the pressure jacket engagement arm 1500 is in the engaged position, the user may lock the pressure jacket engagement arm 1500 into the engaged position as shown in FIG. 11H by activating the detent or latch 1510 to the locked position to lock the pressure jacket engagement arm 1500 in the engaged position. The detent or latch 1510 may be motor operated by a screw mechanism, solenoid, or other mechanism to distally move and lock the detent post into the corresponding hole of the pressure jacket engagement arm 1500. Alternatively, a user may latch or manually lock the detent or latch 1510 into the locked position. While the detent/latch 1510 is now in the engaged position, the fluid injector carriage apparatus 1514 remains in the first disengaged position and also maintaining clearance between the rotating pressure jacket engagement arm 1500 and the frame 1520 of the fluid injector. Movement of the carriage 1514 to the locked and operating position is shown in FIG. 11I. The carriage 1514 is moved in the distal direction, for example by a spring or other biasing member or by a motor such as one associated with the piston of the fluid injector. For example, in one embodiment, the carriage 1514 may be distally moved by a ball screw connected to the piston interface or other motorized component. As the carriage 1514 is moved to the locked and operating position, a distal surface of the carriage 1514 seats the syringe 1508 in the pressure jacket 1504 by abutting the proximal end of the syringe 1508 and pushing it in the distal direction. Further, as the carriage 1514 is moved in the distal direction, the proximal circumferential flange of the pressure jacket 1504 is abutted against the pressure jacket engagement arm 1500 and the distal surface of the pressure jacket engagement arm 1500 is seated against the fluid injector frame 1520. When the system is placed in the locked and operating position, the mechanical slack associated with the syringe 1508, pressure jacket 1504, and the piston is reduced and accounted for, thereby limiting the compliance associated with the fluid injection system and resulting in more accurate injection volumes. In embodiments including a spring loaded or otherwise distally biased carriage 1514, the spring force or biasing force is sufficient to prevent proximal motion of the syringe 1508 and/or pressure jacket 1504 during a fill operation of the syringe 1508. Further, the spring force or biasing force should be sufficient to overcome the spring force when the pressure jacket engagement arm 1500 pushes the arm back during a syringe loading operation. In certain embodiments including a spring biasing force biasing the carriage 1514 in the distal direction, retracting the piston proximally will retract the carriage 1514 proximally against the spring biasing force, thereby allowing the pressure jacket engagement arm 1500 to automatically open in response to a second, torsion spring associated with the pressure jacket engagement arm 1500. In various embodiment, a carriage latching mechanism may be incorporated into the fluid injector to prevent distal movement of the carriage 1514, for example in the event of a power outage to prevent the interface from being accidently locked in the locked and delivery position.

FIGS. 12A to 12H illustrate another embodiment of a fluid injector head with a breech-loading pressure jacket and rotating pressure jacket engagement arm 1600. The pressure jacket engagement arm 1600 includes an opening through which a pressure jacket 1602 may be loaded when the pressure jacket engagement arm 1600 is loaded. The pressure jacket engagement arm 1600 may include a pressure jacket retention mechanism 1604 (see, e.g., FIGS. 13 and 14) to releasably retain the pressure jacket 1602 within the pressure jacket engagement arm 1600. The rotating pressure jacket engagement arm 1600 may rotate from an open position (shown in FIG. 12A) to an engaged position (shown in FIG. 12C) around a pivot point 1606 (see FIG. 12C). The rotating pressure jacket engagement arm 1600 may be manually rotated by a user using a user engagement handle 1610 on the pressure jacket engagement arm 1600 or may be automatically rotated by the fluid injector operating system, for example after a user presses a button or other activation mechanism on the fluid injector system or after the fluid injector senses that a syringe 1612 has been located into the pressure jacket 1602. In other embodiments, the pressure jacket engagement arm 1600 may slide between the open position and the engaged position.

Figure 12A:
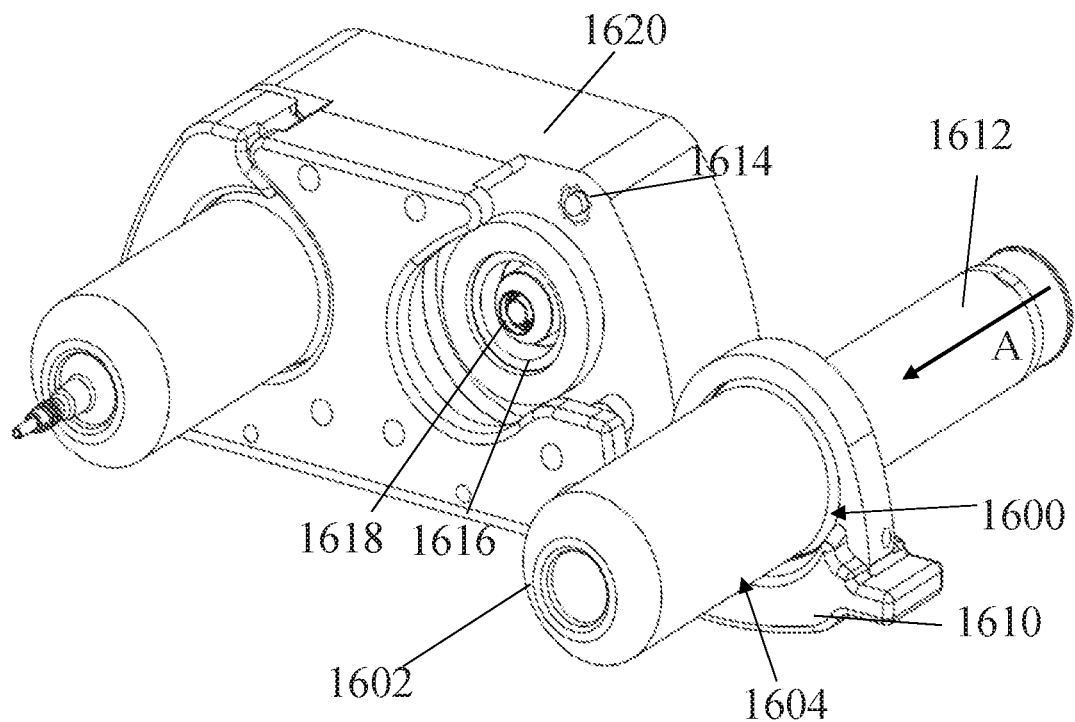
Figure 12B:
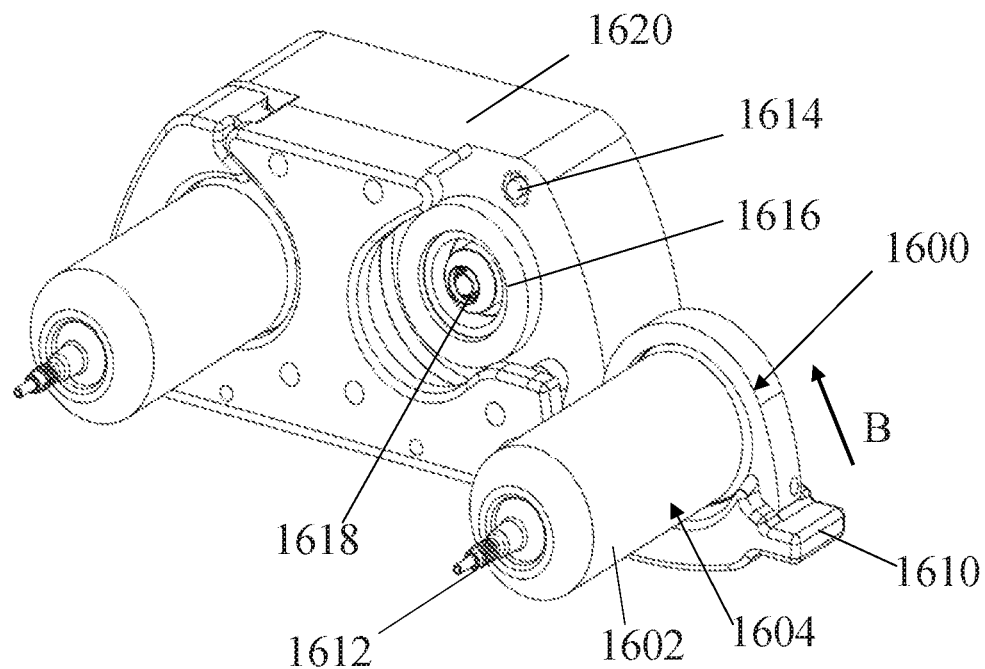
Figure 12F:
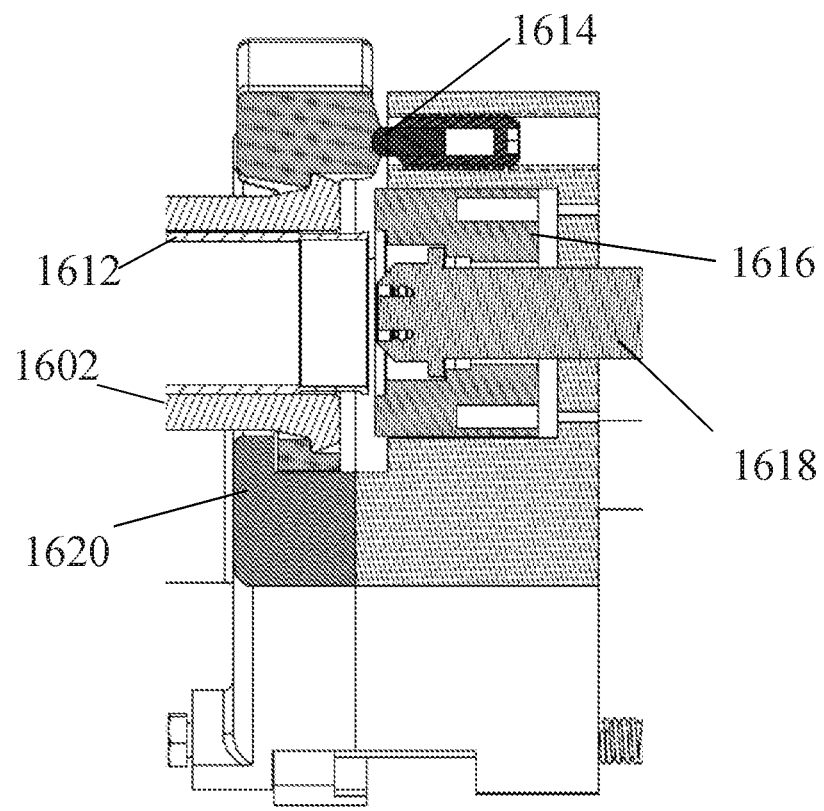

In the open position, a syringe 1612 may be loaded into the pressure jacket 1602 by a breech loading process, see FIG. 12A as described herein. The syringe 1612 is inserted into the proximal open end of the pressure jacket 1602, as shown by arrow A of FIG. 12A, for example until the distal tip and fluid delivery port of the syringe 1612 protrude from a distal opening of the pressure jacket 1602. Once the syringe 1612 is loaded into the pressure jacket 1602, the pressure jacket engagement arm 1600 may be rotated as shown by arrow B in FIG. 12B to the engaged position FIG. 12C. The pressure jacket engagement arm 1600 may be held in the engaged position, for example by a latching mechanism or detent mechanism 1614.

FIG. 12D illustrates a front view of the fluid injector pressure jacket retention mechanism according to embodiments of the present disclosure in the engaged position. FIG. 12E illustrates a cross-section side perspective along line B-B of the fluid injector carriage operation according to an embodiment.

According to embodiments illustrated in FIGS. 12A to 12H, the assembly may include two carriage positions when the pressure jacket engagement arm 1600 is in the engaged position during a fill or injection procedure. Various features of the interface between the fluid injector port and the rotating pressure jacket engagement arm 1600 when in the engaged position is illustrated in cross-sectional view of FIG. 12F. Features of the interface include a carriage 1616 on an axial slide, a biased latching mechanism or detent mechanism 1614 for releasably locking the pressure jacket engagement arm 1600 in the engaged position, a plunger interface 1618 which is attached by a piston to a ball screw or other drive implementation mechanism, a frame 1620 on the proximal end of the fluid injector, a pressure jacket 1602 and the syringe 1612 within the pressure jacket 1602.

Figures 12G, 12H:
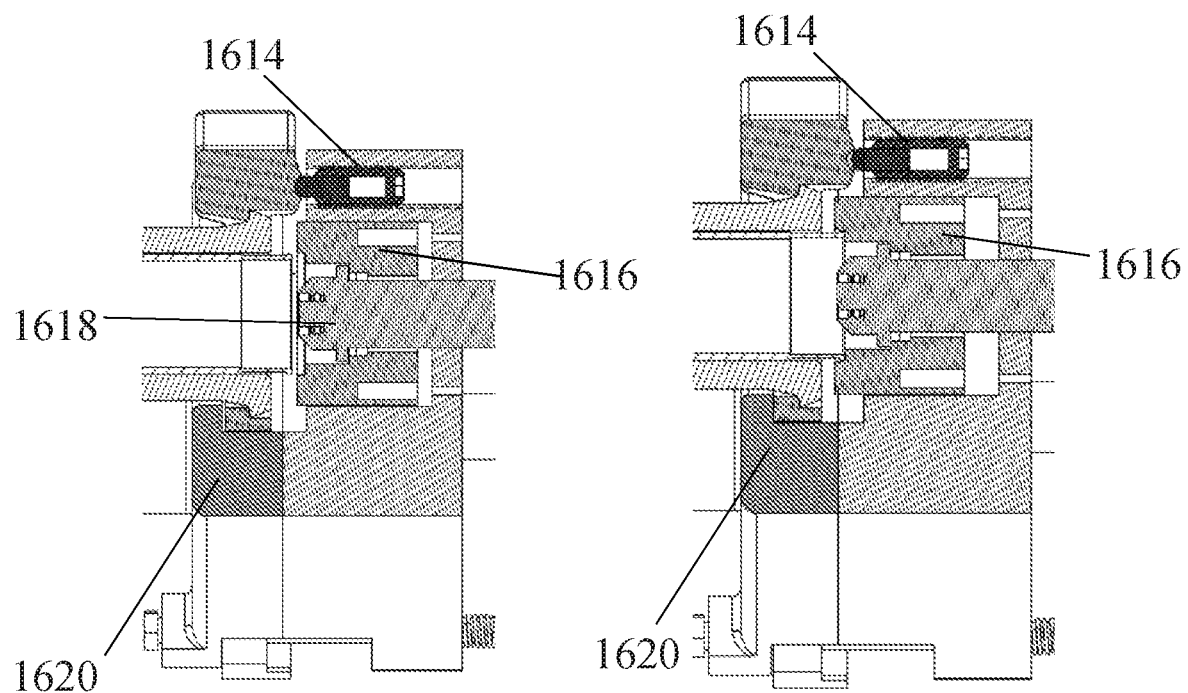

Operation of these features is shown in the two carriage positions illustrated in FIGS. 12G and 12H. In FIG. 12G, rotation of the pressure jacket engagement arm 1600 from the open position to the engaged position moves the biased latching mechanism or detent mechanism1614 in the engaged position. To facilitate the rotation into the engaged position, the fluid injector carriage 1616 is in a first disengaged position and there is clearance between the rotating pressure jacket engagement arm 1600 and the frame 1620 of the fluid injector, shown in FIG. 12G, which results in mechanical slack between the components of the injector, the pressure jacket 1602, and the syringe 1612 and allows movement of the pressure jacket engagement arm 1600 once the biasing force of the latching mechanism or detent mechanism 1614 is overcome. While the latching mechanism or detent mechanism 1614 is now in an engaged position, the fluid injector carriage 1616 remains in the first disengaged position and also maintaining clearance between the rotating pressure jacket engagement arm 1600 and the frame 1620 of the fluid injector. Movement of the carriage 1616 to the locked and operating position is shown in FIG. 12H. The carriage 1616 is moved in the distal direction, for example by a spring or other biasing member or by a motor such as one associated with the piston of the fluid injector, such as a ball screw connected to the piston interface or other motorized component. As the carriage 1616 is moved to the locked and operating position, a distal surface of the carriage 1616 seats the syringe 1612 in the pressure jacket 1602 by abutting the proximal end of the syringe 1612 and pushing it in the distal direction. Further, as the carriage 1616 is moved in the distal direction the proximal circumferential flange of the pressure jacket 1602 is abutted against the pressure jacket engagement arm 1600 and the distal surface of the pressure jacket engagement arm 1600 is seated against the fluid injector frame 1620. According to an embodiment, the latching mechanism or detent mechanism 1614 may move to an unlocked position once the fluid injector is in the locked and operating position. Alternatively, the latching mechanism or detent mechanism 1614 may remain in the biased locked position whenever the pressure jacket engagement arm 1600 is in the closed position. When the system is placed in the locked and operating position, the mechanical slack associated with the syringe 1612, pressure jacket 1602, and the piston is reduced and accounted for, thereby limiting the compliance associated with the fluid injection system and resulting in more accurate injection volumes. In embodiments including a spring loaded or otherwise distally biased carriage1616, the spring force or biasing force is sufficient to prevent proximal motion of the syringe 1612 and/or pressure jacket 1602 during a fill operation of the syringe 1612. Further the spring force or biasing force should be sufficient to overcome the spring force when the pressure jacket engagement arm 1600 pushes the arm back during a syringe loading operation. In certain embodiments including a spring biasing force biasing the carriage 1616 in the distal direction, retracting the piston proximally will retract the carriage 1616 proximally against the spring biasing force, thereby allowing the pressure jacket engagement arm 1600 to automatically open in response to a second, torsion spring associated with the pressure jacket engagement arm 1600. Alternatively, a user may manually rotate the pressure jacket engagement arm 1600 back to the open position by grasping the handle 1610 and rotating the arm 1600 outwardly. In various embodiment, a carriage latching mechanism may be incorporated into the fluid injector to prevent distal movement of the carriage1616, for example in the event of a power outage to prevent the interface from being accidently locked in the locked and delivery position.

FIGS. 13A to 13E illustrate one embodiment of a pressure jacket retention mechanism 1700 that may be used with embodiments of a breech loading fluid injector system. The pressure jacket retention mechanism 1700 ensures that the pressure jacket 1702 is securely retained in a pressure jacket engagement arm 1704, while allowing the pressure jacket 1702 to be removed, for example, for cleaning or replacement of the pressure jacket 1702. FIG. 13A illustrates a proximal perspective view of a pressure jacket 1702 retained in the pressure jacket retention mechanism 1700 of an engagement arm 1704 according to one embodiment. The pressure jacket 1702 may comprise a circumferential flange 1706 at the proximal end of the pressure jacket sidewall. The outer circumference of the circumferential flange 1706 may have a beveled surface having a greater diameter at the distal edge of the flange 1706 relative to the proximal edge, see FIG. 13B. The beveled circumferential flange 1706 may be used to retain the pressure jacket 1702 in the mechanism 1700. As shown in FIG. 13B, the pressure jacket 1702 is breech loaded at an angle shown by arrow A into the receiving opening of the engagement arm 1704. On one side of the receiving opening, an internal lip engages a side of the beveled circumferential flange 1706. The pressure jacket 1702 may then be swiveled as shown by arrow B in FIG. 13C until the pressure jacket 1702 seats in the receiving opening as shown in FIG. 13D. When the pressure jacket 1702 is seated, as shown in FIG. 13D, the other side of the beveled circumferential flange 1706 engages a biased detent or latch 1708 on the inner surface of the receiving opening, which retains the pressure jacket 1702 into receiving opening of the pressure jacket engagement arm 1704, FIG. 13E. The pressure jacket 1702 may be removed from the pressure jacket engagement arm 1704 by reversing these steps.

Figure 14A:
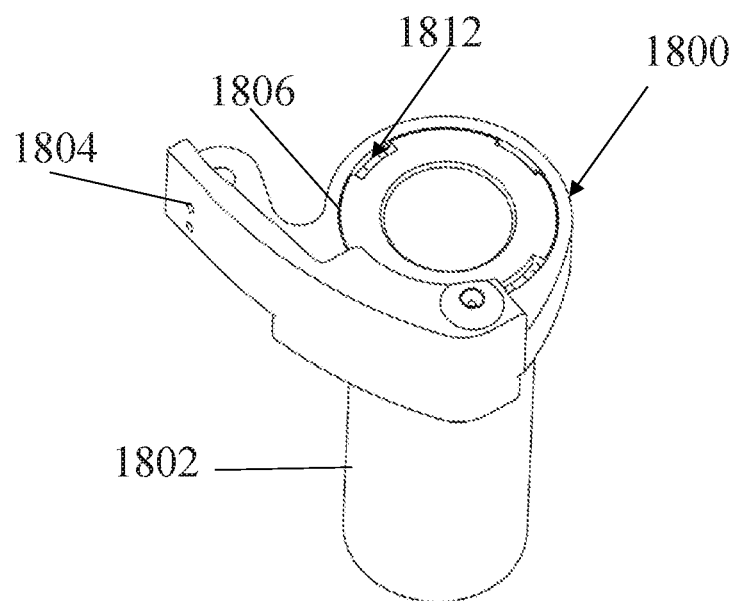
FIGS. 14A to 14F illustrate an alternate mechanism for engaging the pressure jacket in a receiving portion of a fluid injector carriage according to one embodiment.
Figure 14B:
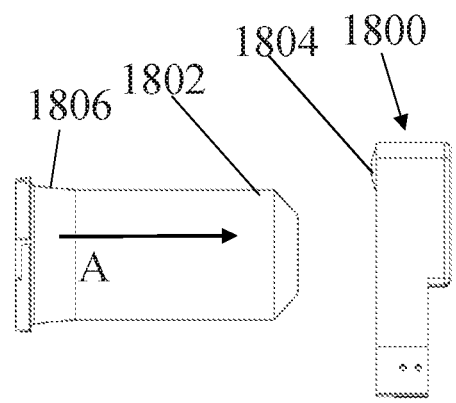
Figure 14C:
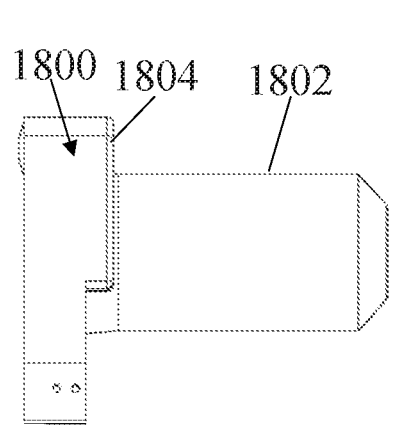
Figure 14D:
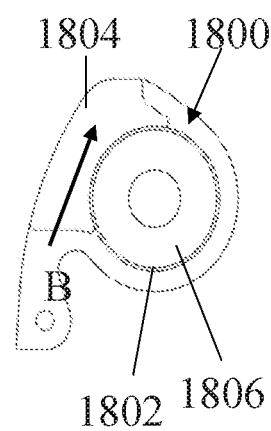
Figure 14E:
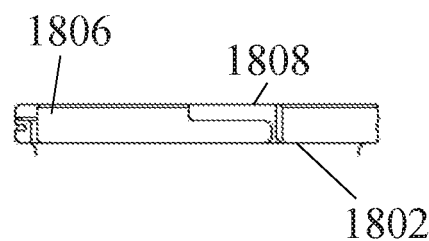
Figure 14F:
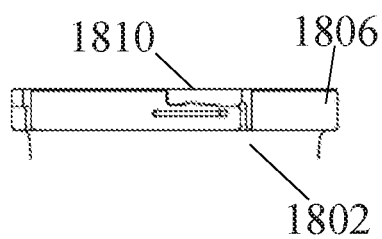

FIGS. 14A to 14F illustrate another embodiment of a pressure jacket retention mechanism 1800 that may be used with embodiments of a breech loading fluid injector system using a bayonet type retention mechanism. FIG. 14A illustrates a proximal perspective view of a pressure jacket 1802 retained in the pressure jacket retention mechanism 1800 of an engagement arm 1804 according to one embodiment. The pressure jacket 1802 may comprise a circumferential flange 1806 at the proximal end of the pressure jacket sidewall. The outer circumference of the circumferential flange 1806 includes a holding groove, such as a standard bayonet-type holding groove 1808, see FIG. 14E or a latching bayonet-type groove 1810, see FIG. 14F. The grooves on the circumferential flange 1806 interact with associated engagement pins 1812 on the inner surface of the opening of the pressure jacket retaining arm 1804 as shown in FIG. 14A. As shown in FIG. 14B, the pressure jacket 1802 is breech loaded shown by arrow A into the receiving opening of the engagement arm 1804 in an orientation where the lateral portions of the holding grooves align with the engagement pins 1812 on the engagement arm 1804 until the pressure jacket circumferential flange 1806 abuts the corresponding flange of the opening as shown in FIG. 14C. Once the pressure jacket 1802 is loaded and the lateral portions of the holding grooves have engaged the pins 1812, the pressure jacket 1802 may then be rotated clockwise or counterclockwise, as shown by arrow B in FIG. 14D to engage the pins 1812 with the portions of the groove that is perpendicular to the lateral axis in a bayonet-type locking process. FIG. 14E illustrates an embodiment of a holding groove 1808 for holding the pins and thereby holding the pressure in position. FIG. 14F illustrates another embodiment of a latching groove 1810 for latching the pins 1812 by the groove having a pocket to accept the pins 1812 and thereby latching the pressure jacket 1802 in position.

With reference to FIGS. 15A-17C, a pressure jacket and syringe retaining assembly 1900 according to another example or aspect of the present disclosure is illustrated. The pressure jacket and syringe retaining assembly 1900 may include a base plate 1902 operatively connected to an injector housing, such as the injector housing 102 of the fluid injector system 100 illustrated in FIG. 1. The fluid injector system 100 of FIG. 1 may include one or more of the pressure jacket and syringe retaining assemblies 1900 depending on the number of syringes to be attached. According to various embodiments, the fluid injector system 100 of FIG. 1 may include two or more pressure jacket and syringe retaining assemblies 1900 to retain two or more syringes. The base plate 1902 may include a body 1904 for supporting the components of the pressure jacket and syringe retaining assembly 1900. According to various embodiments, the base plate 1902 may be operatively connected to or attached to a fluid injector system, such as the fluid injector system 100 illustrated in FIG. 1, or may be formed integrally with the fluid injector system. The base plate 1902 may hold a pressure jacket 1906 that is configured to receive and hold a syringe 1908. The pressure jacket 1906 may be pre-installed in the pressure jacket and syringe retaining assembly 1900 such that only the syringe 1908 may be inserted or removed from the pressure jacket 1906 or may be inserted/replaced after assembly of the pressure jacket and syringe retaining assembly 1900.

The pressure jacket and syringe retaining assembly 1900 may also include at least two retaining arms 1910a, 1910b that are operatively connected to the base plate 1902 and used to retain the syringe 1908 in the pressure jacket 1906 and to retain the pressure jacket 1906 on the fluid injector. Each retaining arm 1910a, 1910b may include at least two base members or support arms 1912a, 1912b, 1912c, 1912d pivotably connected at respective pivot points 1914a, 1914b to the base plate 1902. The base members 1912a, 1912b, 1912c, 1912d may be configured to rotate towards and away from the pressure jacket 1906 and the syringe 1908 between an open position and a closed position. In the open position (shown in FIGS. 17A-17C), the retaining arms 1910a, 1910b may be separated from one another at a first distance that permits insertion of the pressure jacket 1906 and the syringe 1908 between the retaining arms 1910a, 1910b for operative connection to the fluid injector system. The retaining arms 1910a, 1910b may also be pivoted towards one another to move into the closed position. In the closed position, the retaining arms 1910a, 1910b are positioned in contact with one another or adjacent to one another such that an installed pressure jacket 1906 and syringe 1908 are retained within the pressure jacket and syringe retaining assembly 1900 such that the pressure jacket 1906 and the syringe 1908 are prevented from moving in a distal direction. In the closed position, the retaining arms 1910a, 1910b are separated at a second distance from one another. In various embodiments, the first distance between the retaining arms 1910a, 1910b in the open position is greater than the second distance between the retaining arms 1910a, 1910b in the closed position. In various alternative embodiments, the retaining arms 1910a, 1910b may be positioned at an intermediate position, such that the syringe 1908 may be removed from the pressure jacket and syringe retaining assembly 1900 but the pressure jacket 1906 is retained in the pressure jacket and syringe retaining assembly 1900 by the retaining arms 1910a, 1910b. The retaining arms 1910a, 1910b may be moved to the intermediate position when an operator wishes to replace the syringe 1908 within the pressure jacket 1906 without removing the pressure jacket 1906 from the pressure jacket and syringe retaining assembly 1900. In various embodiments, when the retaining arms 1910a, 1910b are moved to the intermediate position, the retaining arms 1910a, 1910b are positioned at a third distance from one another, in which the third distance is less than the first distance when the retaining arms 1910a, 1910b are in the open position and greater than the second distance when the retaining arms 1910a, 1910b are in the closed position.

Each retaining arm 1910a, 1910b may also include a retaining portion 1916a, 1916b that include respective retaining surfaces operatively connected to a distal end of the respective base members 1912a, 1912b, and 1912c, 1912d, respectively. In some examples or aspects, at least a portion of the retaining portions 1916a, 1916b may be made of a plastic or metal, such as stainless steel. Each retaining portion 1916a, 1916b may form a half-circle that, when formed with the opposing retaining element 1916a, 1916b, creates a full-circle that encompasses the distal ends of the pressure jacket 1906 and of the syringe 1908. Each of the retaining portions 1916a, 1916b may have a curvature along its longitudinal axis that generally corresponds to a curvature of the distal end of the syringe 1908 and the distal end of the pressure jacket 1906. Contact between the retaining portions 1916a, 1916b prevent distal movement of the pressure jacket 1906 and the syringe 1908 within the pressure jacket and syringe retaining assembly 1900. As fluid pressure from the fluid injector works to move the pressure jacket 1906 and the syringe 1908 in the distal direction, the retaining portions 1916a, 1916b create an opposing force in a proximal direction to prevent the pressure jacket 1906 and the syringe 1908 from moving in the distal direction relative to the fluid injector.

In various embodiments, each retaining portion 1916a, 1916b may also include a syringe cone support positioned and held within the retaining element 1916a, 1916b. The syringe cone supports may be made of a transparent or translucent material, such as a polymeric material to support the distal portions of the syringe 1908 and allow inspection of the distal portion of the syringe 1908, for example visual inspection or inspection using a camera, sensor, or other detector set-up. For example, inspection of the distal portion of the syringe 1908 may allow for detection of air within the syringe 1908 or detection of fluid type within the syringe 1908, as described in PCT International Application Publication Nos. WO 2017/040152 and 2017/040154, the disclosures of which are incorporated by reference herein. The retaining elements 1916a, 1916b may surround and stiffen the syringe cone supports and provide a stronger abutment surface for the conical distal end of the syringe 1908. The syringe cone supports may be conical in shape to correspond to the conical shape of the distal end of the syringe 1908. While the syringe cone supports are illustrated as conical in shape, the shape of the syringe cone supports may be any shape that is contoured to match the shape of the distal end of the syringe 1908.

Figure 15A:
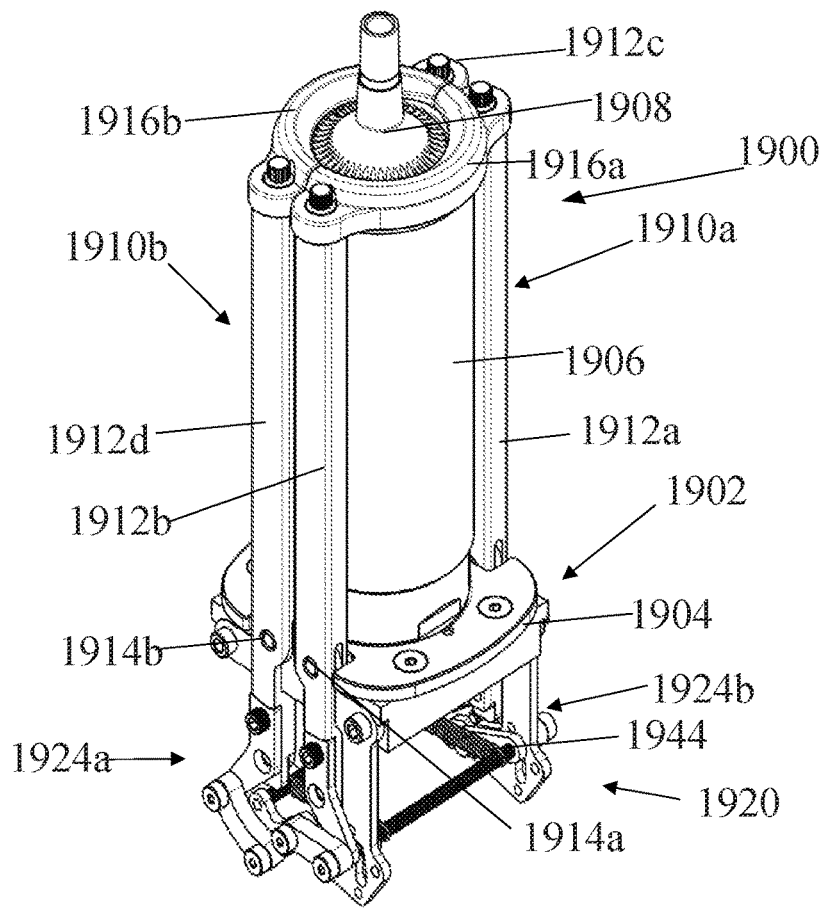
FIGS. 15A to 15C illustrate an embodiment of a front-loading pressure jacket retention mechanism in a closed position with a syringe and pressure jacket according to an aspect of the present disclosure.
Figure 15B:
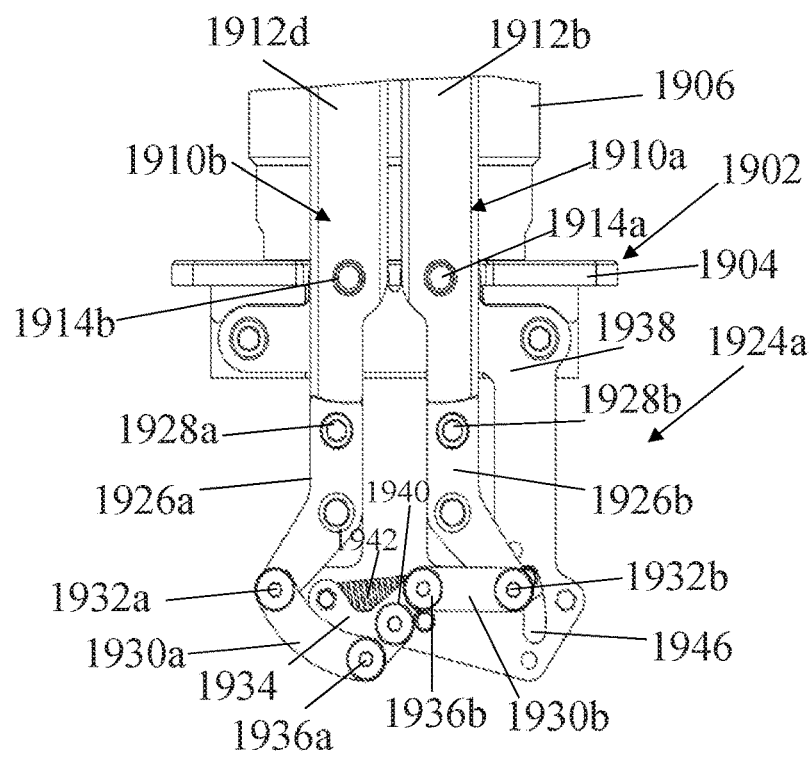
Figure 16A:
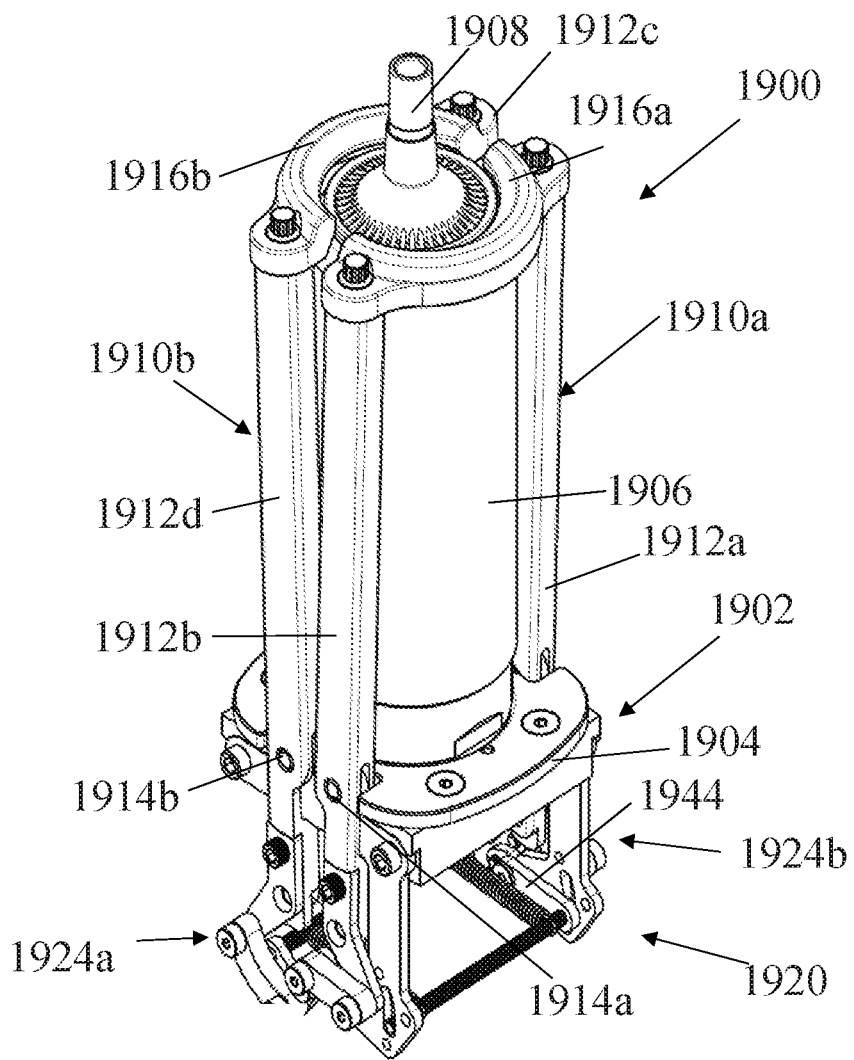
FIGS. 16A to 16C illustrate the front-loading pressure jacket retention mechanism of FIGS. 15A-15C in a second open position.
Figure 16B:
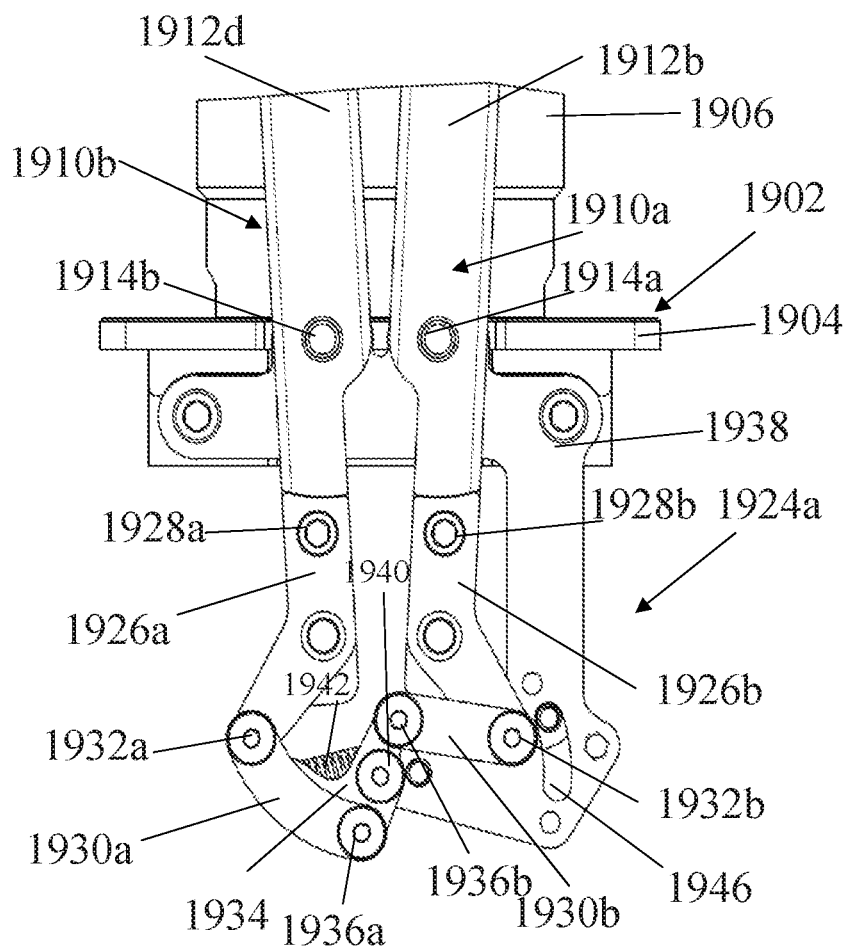
Figure 17A:
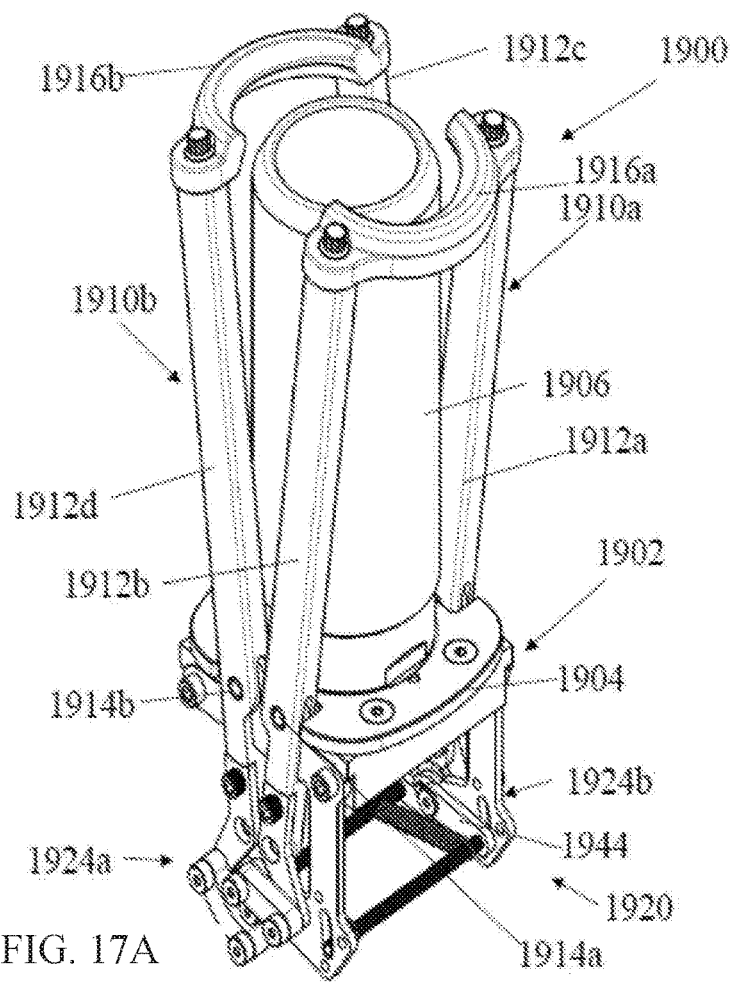
FIGS. 17A to 17C illustrate the front-loading pressure jacket retention mechanism of FIGS. 15A-15C in a first open position showing the syringe removed from the pressure jacket.
Figure 17B:
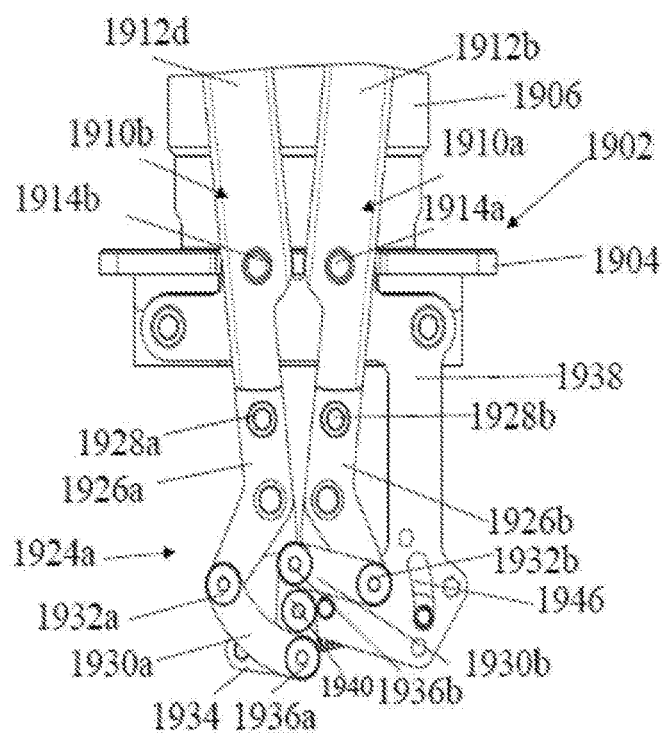
Figure 18:
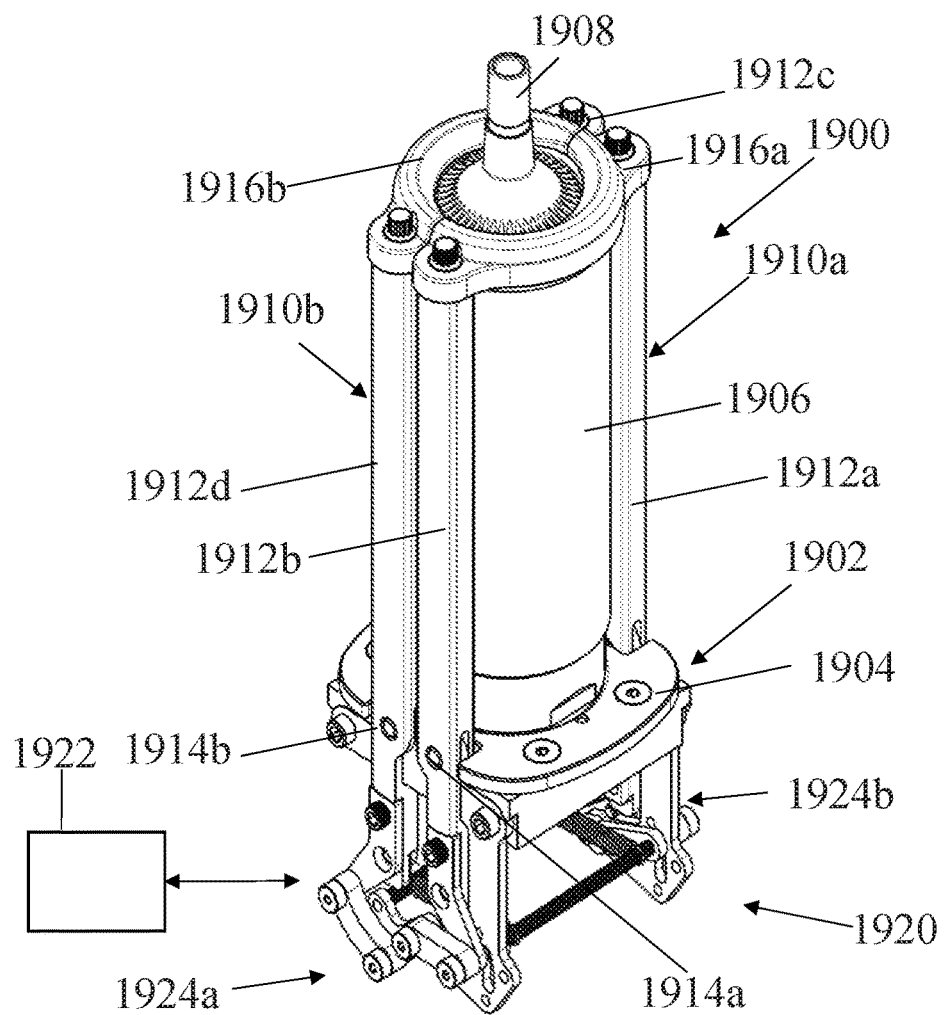
FIG. 18 is a perspective view of the front-loading pressure jacket retention mechanism of FIGS. 15A-17C that includes an electro-mechanical motor operatively connected thereto according to an aspect of the present disclosure.

With continued reference to FIGS. 15B, 16B, and 17B, a linkage arrangement 1920 according to various embodiments for actuating movement of the retaining arms 1910a, 1910b for the pressure jacket and syringe retaining assembly 1900 is shown and described. The linkage arrangement 1920 is provided to move the retaining arms 1910a, 1910b between the closed position, the intermediate position, and the open position. In various embodiments, the linkage arrangement 1920 may be manually activated by an operator by pulling apart or pushing together the retaining arms 1910a, 1910b. In various embodiments, the linkage arrangement 1920 may be activated using an electromechanical motor 1922 (see FIG. 18) provided within the fluid injector or operatively connected to the fluid injector. In various embodiments, the linkage arrangement 1920 is configured to move the retaining arms 1910a, 1910b in unison between the closed position, the intermediate position, and the open position. For example, in one embodiment, "in unison" is understood to mean that the retaining arms 1910a, 1910b move outwardly and inwardly relative to one another at the same or similar speed or rate to ensure that each retaining arm 1910a, 1910b moves the same or similar distance. By moving in unison, the linkage arrangement 1920 ensures that the retaining arms 1910a, 1910b are provided at the correct distance from one another when moved to the closed position, the intermediate position, or the open position.

In various embodiments, the linkage arrangement 1920 may include a first linkage assembly 1924a and a second linkage assembly 1924b. The linkage assemblies 1924a, 1924b may be provided on opposing sides of the base plate 1902. In various embodiments, the first linkage assembly 1924a is identical to the second linkage assembly 1924b. Therefore, a description of the first linkage assembly 1924a is provided below, which also corresponds to the description of the second linkage assembly 1924b. The first linkage assembly 1924a may include a first retaining arm link 1926a and a second retaining arm link 1926b. The first retaining arm link 1926a may be connected, at one end, to a proximal end of one of the retaining arms 1910a and the second retaining arm link 1926b may be connected, at one end, to a proximal end of the other retaining arm 1910b. The retaining arm links 1926a, 1926b may be connected to the retaining arms 1910a, 1910b via mechanical fasteners 1928a, 1928b. Each of the retaining arm links 1926a, 1926b may be operatively connected to a corresponding connecting link 1930a, 1930b. Each connecting link 1930a, 1930b may be connected, at one end, to a corresponding end of the retaining arm link 1926a, 1926b. Each connecting link 1930a, 1930b may be connected to the corresponding retaining arm link 1926a, 1926b using a connecting pin 1932a, 1932b.

In various embodiments, the connecting links 1930a, 1930b may also be connected to a central link 1934. The connecting links 1930a, 1930b may be connected to the central link 1934 with connecting pins 1936a, 1936b. In various embodiments, the central link 1934 may also be connected to a base link 1938 that is also connected to the base plate 1902. The central link 1934 may be connected to the base link 1938 using a connecting pin 1940.

With reference to FIGS. 15B, 16B, and 17B, in operation of the linkage arrangement 1920, to move the retaining arms 1910a, 1910b from the closed position to the open position, the retaining arms 1910a, 1910b may be pulled apart from one another. As the retaining arms 1910a, 1910b are separated, the proximal ends of the retaining arm links 1926a, 1926b move inwardly towards one another in an inward direction. As the proximal ends of the retaining arm links 1926a, 1926b move inwards towards one another, the connecting links 1930a, 1930b also move inwardly towards one another. The ends of the connecting links 1930a, 1930b that are connected to the central link 1934 begin to rotate relative to one another in a counter-clockwise direction. Based on this movement of the linkage arrangement 1920, the retaining arms 1910a, 1910b are permitted to rotate outwardly relative to one another to move into the open position. In a similar fashion, the linkage arrangement 1920 may move in a manner opposite to the manner described above to move the retaining arms 1910a, 1910b from the open position to the closed position or intermediate position.

The first linkage assembly 1924a may also include a biasing member 1942 that is configured to bias the first linkage assembly 1924a and, indirectly, the retaining arms 1910a, 1910b towards the closed position. Therefore, as the operator or the electromechanical motor 1922 pulls the retaining arms 1910a, 1910b apart from one another, the retaining arms 1910a, 1910b are biased to closed towards one another with the release of the outward pressure on the retaining arms 1910a, 1910b. In various embodiments, the biasing member 1942 may be a spring. The biasing member 1942 may be connected, at one end, to the central link 1934 and, at an opposing end, biasing member link 1944. The biasing member link 1944 is connected at both ends to the base link 1938. One end of the biasing member link 1944 is fixed to the base link 1938 and an opposing end of the biasing member link 1944 is pivoting connected to a groove 1946 defined in the base link 1938. The end of the biasing member link 1944 connected to the groove 1946 permits the corresponding end of the biasing member link 1944 to slide along the groove 1946.

During operation of the first linkage assembly 1924a, the ends of the connecting links 1930a, 1930b connected to the central link 1934 rotate in a first or counter-clockwise direction in order to rotate the central link 1934 in the same first or counter-clockwise direction. With this counter-clockwise rotation, the end of the central link 1934 that is connected to the biasing member 1942 rotates in a first or counter-clockwise direction and begins to stretch or expand the biasing member 1942. With continued rotation of the central link 1934, the biasing member 1942 continues to be stretched or expanded. With the stretching or expanding of the biasing member 1942, the potential energy stored in the biasing member 1942 increases. Therefore, as the outward pressure on the retaining arms 1910a, 1910b is reduced, the biasing member 1942 is configured to pull the central link 1934 back to its resting position such that the biasing member 1942 causes the central link 1934 to rotate in a second or clockwise direction to ensure the connecting links 1930a, 1930b also rotate in a second or clockwise direction and pull the retaining arms 1910a, 1910b back into the closed position.

To ensure a smooth and consistent transition between the closed position, the open position, and the intermediate position, the groove 1946 defined in the base link 1938 permits the end of the biasing member 1942 connected to the groove 1946 to maintain an equilibrium between the components of the first linkage assembly 1924a. As the central link 1934 rotates in the counter-clockwise direction and pulls the connected end of the biasing member 1942 in the counter-clockwise direction, the opposing end of the biasing member 1942 is configured to slide within the groove 1946 to ensure that the biasing member 1942 remains substantially horizontal relative to the first linkage assembly 1924a. Once the retaining arms 1910a, 1910b have been pulled apart into the open position, the end of the biasing member 1942 connected to the groove 1946 is moved to the bottom of the groove 1946 and holds the biasing member 1942 in the expanded position to allow the retaining arms 1910a, 1910b to remain in the open position until an inward force is applied to the retaining arms 1910a, 1910b.

Figure 15C:
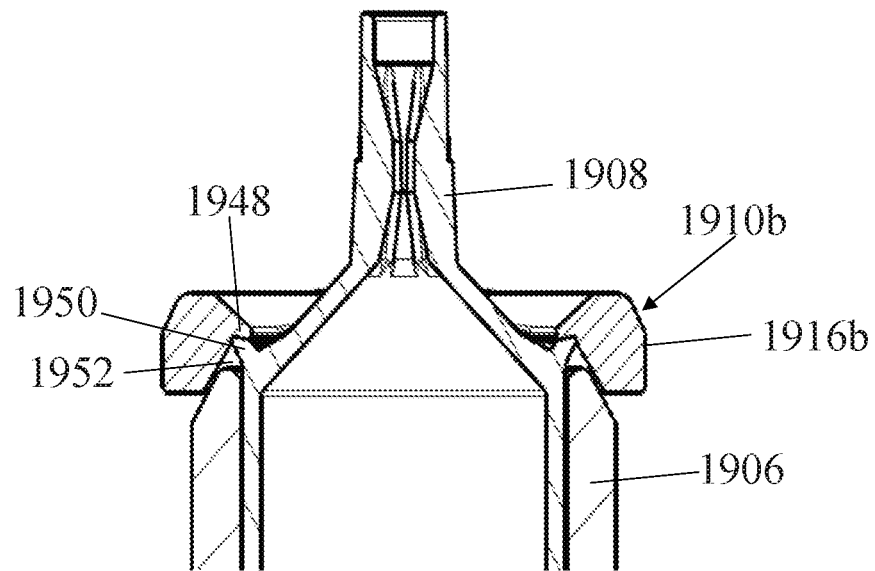
Figure 16C:
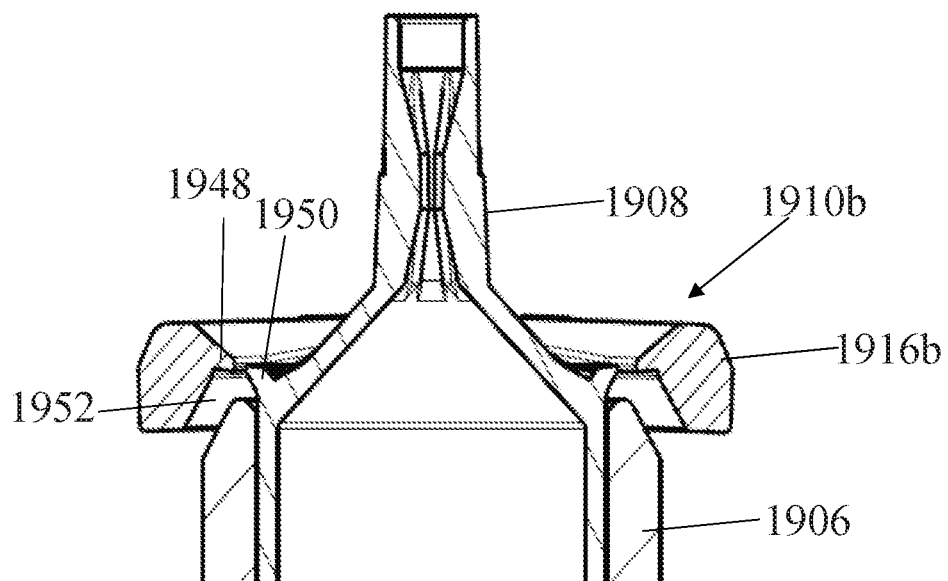
Figure 17C:
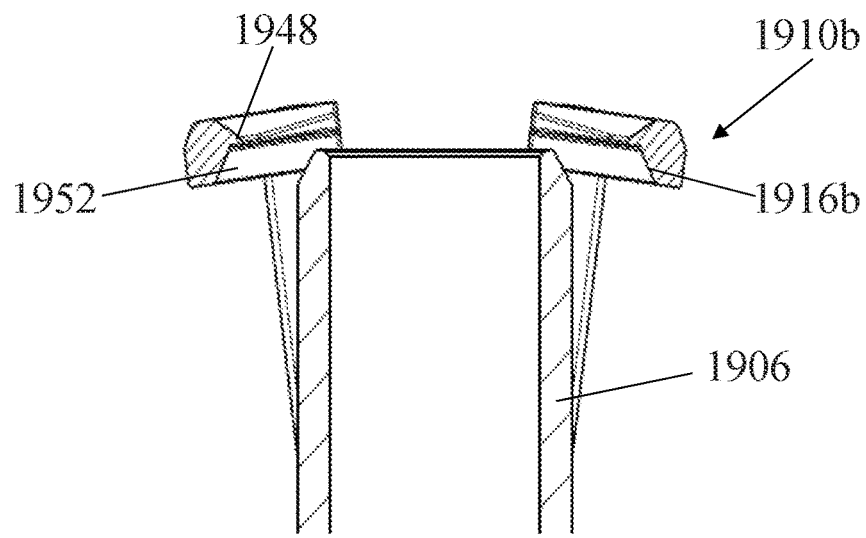

With reference to FIGS. 15C, 16C, and 17C, in various embodiments, the pressure jacket and syringe retaining assembly 1900 may also include features provided on the retaining portions 1916a, 1916b to assist in retaining the pressure jacket 1906 and the syringe 1908 in the fluid injector. In one embodiment, each of the retaining portions 1916a, 1916b may include an inner protrusion 1948 (also referred to as a syringe retaining surface) that circumferentially extends along an inner surface of the retaining portions 1916a, 1916b. The inner protrusions 1948 further reduce the diameter of the retaining portions 1916a, 1916b to engage at least a portion of the distal end of the syringe 1908 loaded into the fluid injector. In one embodiment, the inner protrusions 1948 may be dimensioned to engage and establish contact with a drip flange 1950 of the distal end of the syringe 1908 that acts as a circumferential wall around the distal end of the syringe 1908. It is also to be understood, however, that the inner protrusions 1948 may be structured and dimensioned to contact any portion of the distal end of the syringe 1908. The inner protrusions 1948 may include a surface that engages the distal end of the syringe 1908 that is angled relative to a longitudinal axis of the syringe 1908 to create an inward pushing force on the syringe 1908 to retain the syringe 1908 in the fluid injector. As the syringe 1908 may try to move in a distal direction due to fluid pressures exerted by the fluid injector, the inner protrusions 1948 may create an increasing inward pressure on the syringe 1908 to ensure the syringe 1908 remains retained in the fluid injector. In one embodiment, the drip flange 1950 may extend at a 45 degree angle relative to the longitudinal axis of the syringe 1908, while the inner protrusions 1948 may extend at the same or similar angle relative to the longitudinal axis of the syringe 1908.

With continued reference to FIGS. 15C, 16C, and 17C, in various embodiments, the retaining portions 1916a, 1916b may also define a retaining groove 1952 (also referred to as a pressure jacket retaining surface) configured to receive at least a portion of the pressure jacket 1906 and/or the syringe 1908. In one embodiment, the retaining grooves 1952 may be structured and dimensioned to receive the distal end of the pressure jacket 1906 to assist in retaining the pressure jacket 1906 within the fluid injector. The retaining grooves 1952 also assist in creating an inward radial pressure to keep the retaining arms 1910a, 1910b in the closed position when the pressure jacket 1906 and the syringe 1908 are pushed in a distal direction due to fluid pressure exerted by the fluid injector.

Figure 19:
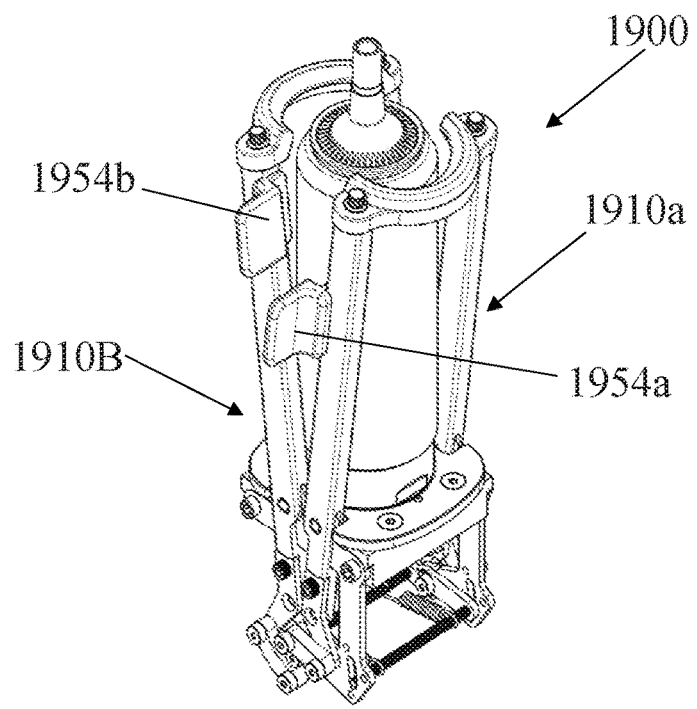
FIG. 19 is a perspective view of the front-loading pressure jacket retention mechanism of FIGS. 15A-17C that includes at least one finger tab provided on the retaining arms according to an aspect of the present disclosure.

As shown in FIG. 19, in various embodiments, the retaining arms 1910a, 1910b may also include at least one finger tab 1954a, 1954b to assist in opening the retaining arms 1910a, 1910b to insert or remove the pressure jacket 1906 and/or syringe 1908. In one embodiment, a finger tab 1954a, 195b is provided on each of the base members 1912a, 1912b, 1912c, 1912d. In this embodiment, an operator can use his/her thumb and index fingers to assert an outward force on an inner surface of the finger tabs 1954a, 1954b to push the retaining arms 1910a, 1910b apart from one another. In a similar fashion, the operator can create an inward pressing force on the finger tabs 1954a, 1954b to push the retaining arms 1910a, 1910b into the closed position. In another embodiment, a single finger tab 1954a, 1954b may be provided on only one of the retaining arms 1910a, 1910b, which can be used to move the retaining arms 1910a, 1910b between the open position, the closed position, and the intermediate position. In one embodiment, the finger tabs 1954a, 1954b may be positioned at or proximate to the distal end of the retaining arms 1910a, 1910b.

FIGS. 20A-22C illustrate, in another embodiment, the structure and operation of a front-loading pressure jacket and syringe retaining assembly 2000. FIGS. 20A-22C illustrate the front-loading pressure jacket and syringe retaining assembly 2000 after insertion of the syringe through a distal access opening. The pressure jacket and syringe retaining assembly 2000 includes the same base plate and retaining arms using the pressure jacket and syringe retaining assembly 1900 illustrated in FIGS. 15A-17C.

Figure 20A:
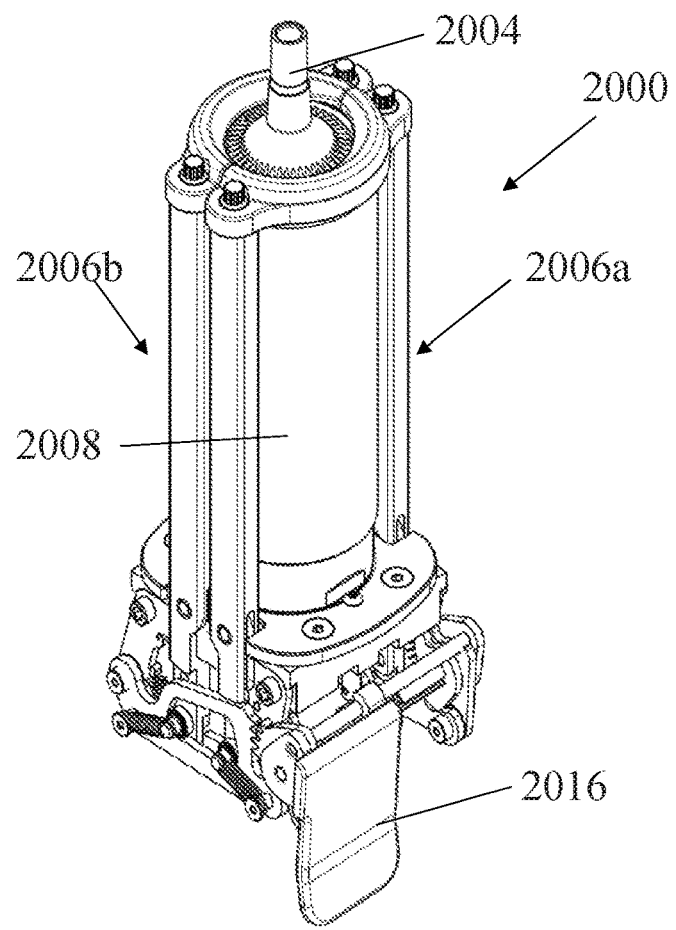
FIGS. 20A to 20C illustrate another embodiment of a front-loading pressure jacket retention mechanism in a closed position with a syringe and pressure jacket according to an aspect of the present disclosure.
Figure 20B:
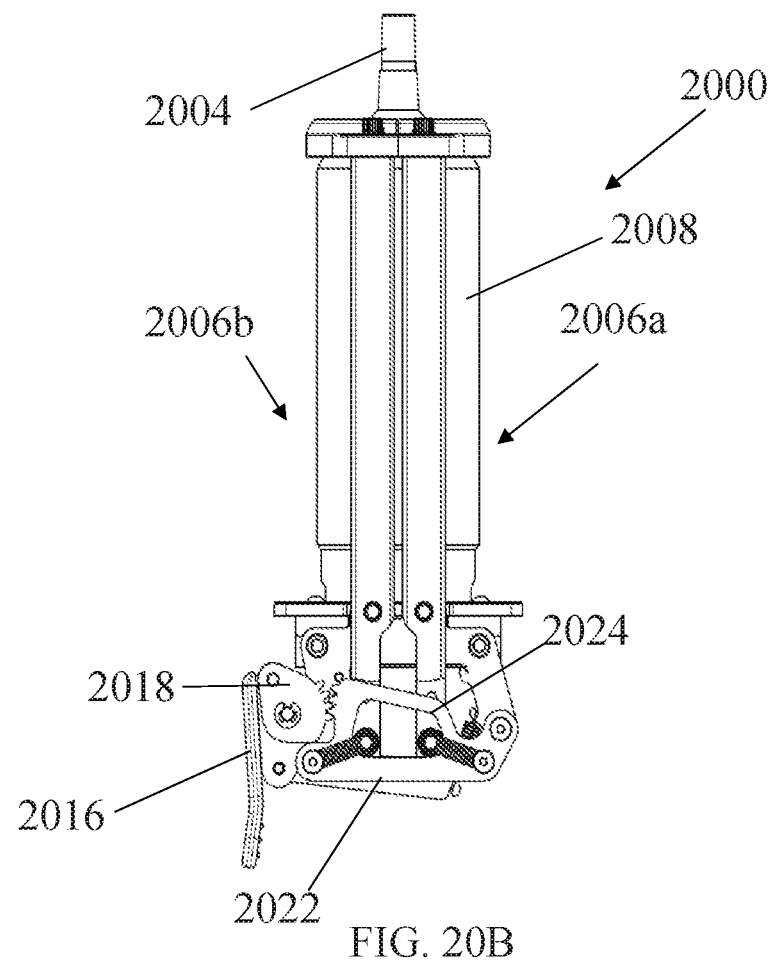
Figure 20C:
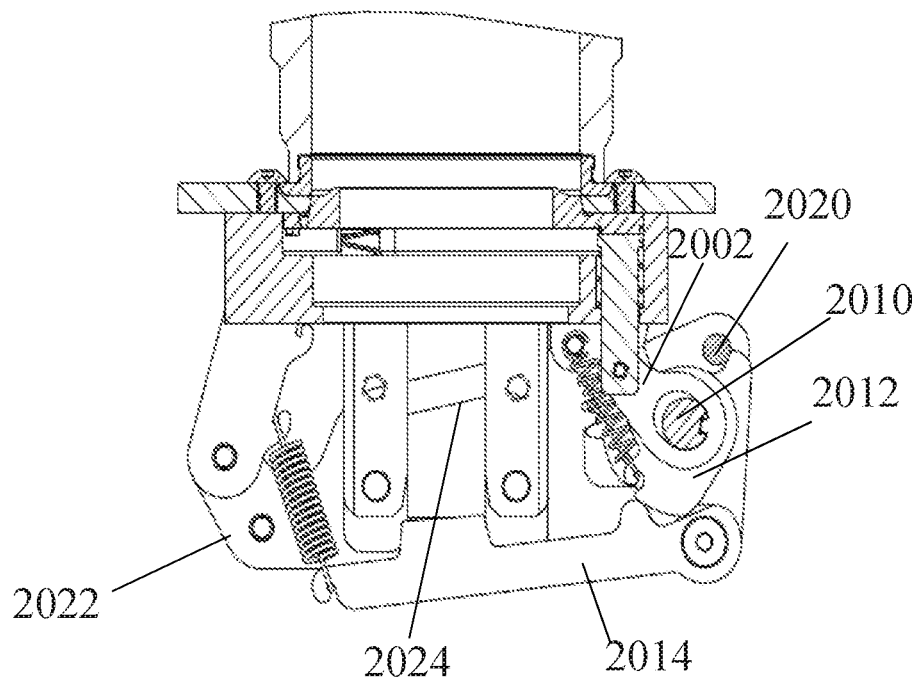
Figure 21A:
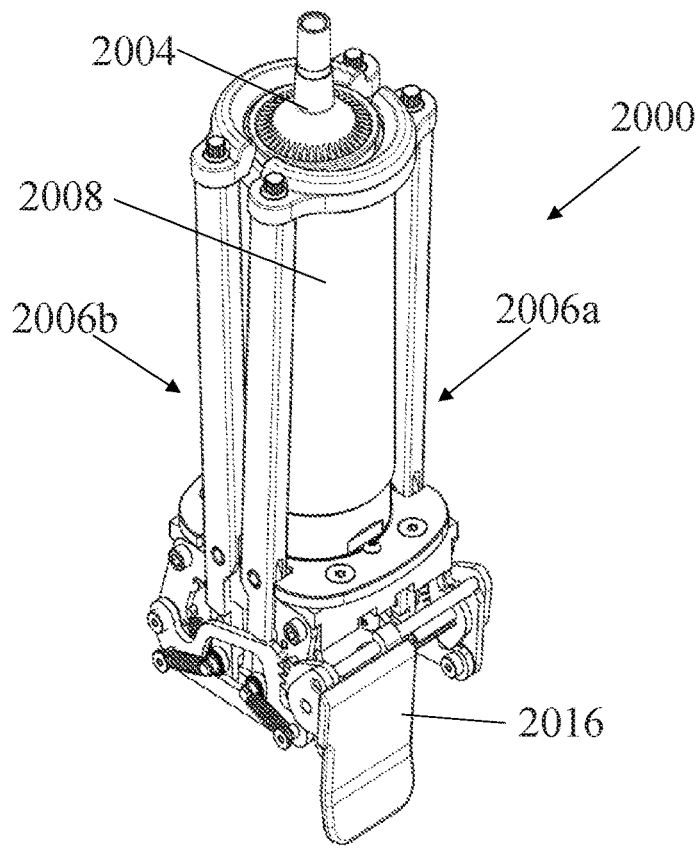
FIGS. 21A to 21C illustrate the front-loading pressure jacket retention mechanism of FIGS. 20A-20C in a second open position.
Figure 21B:
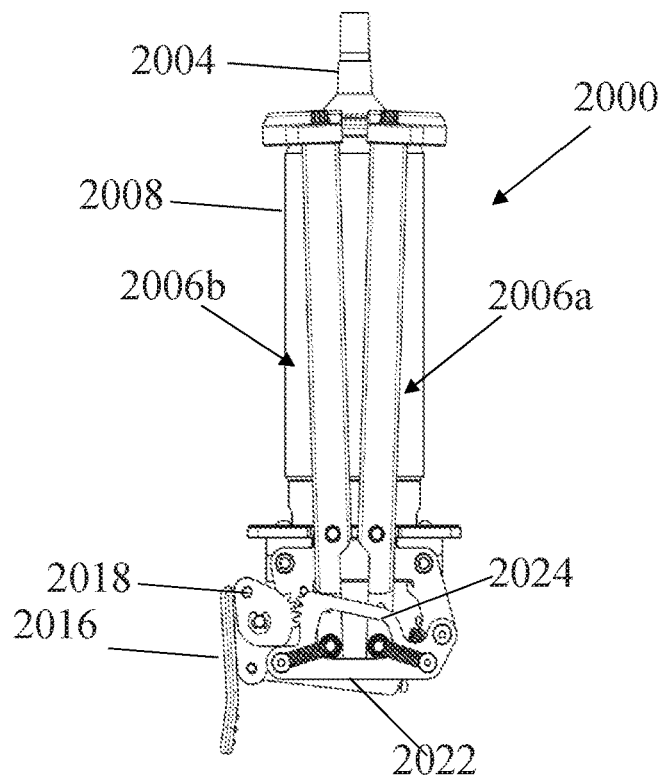
Figure 21C:
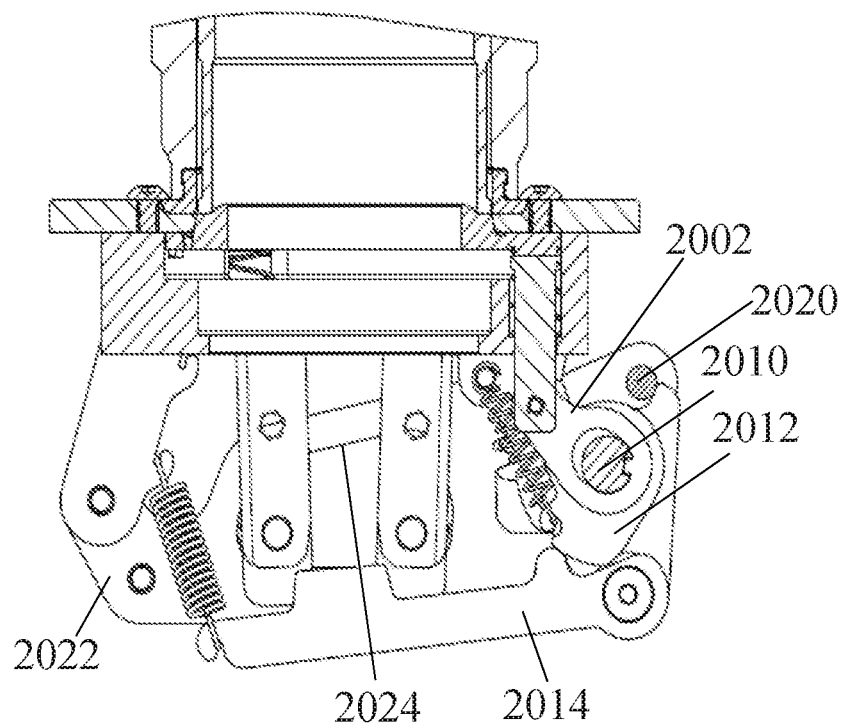
Figure 22A:
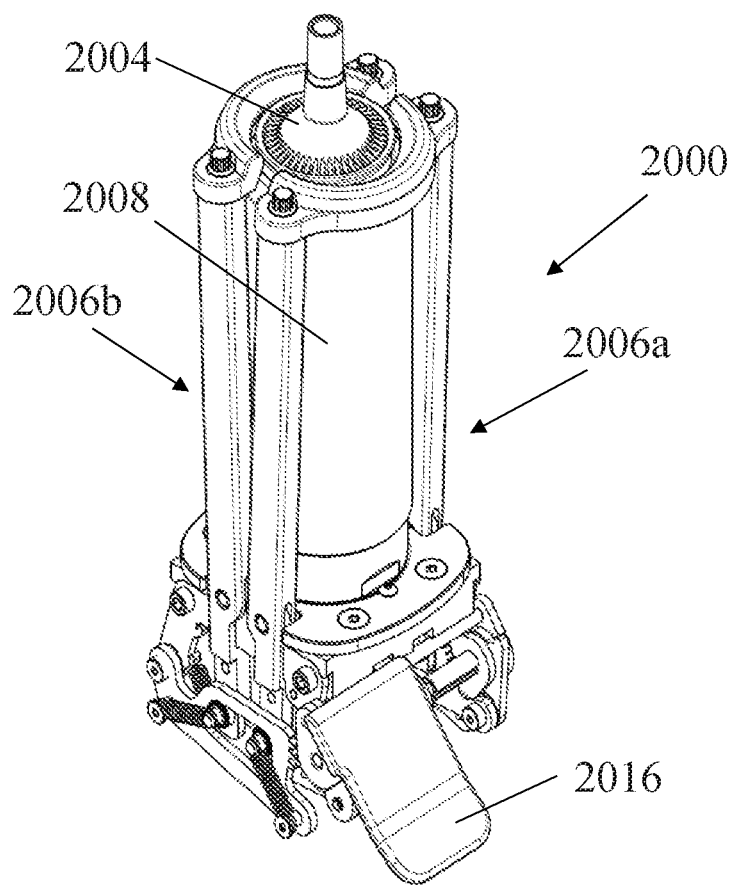
FIGS. 22A to 22C illustrate the front-loading pressure jacket retention mechanism of FIGS. 20A-20C in a first open position showing the syringe removed from the pressure jacket.
Figure 22B:
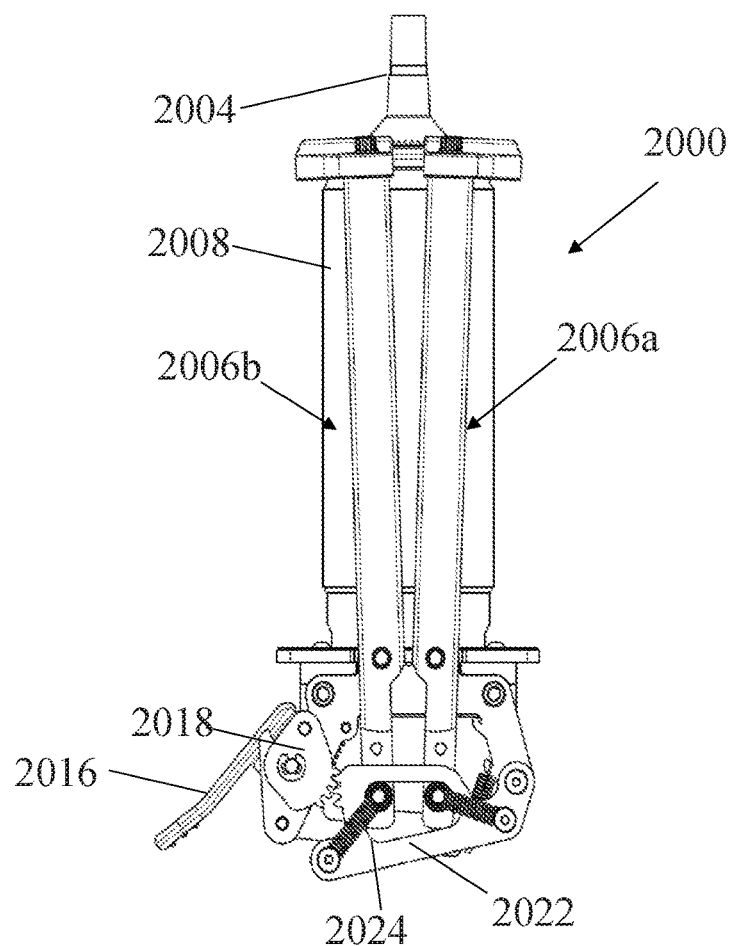
Figure 22C:
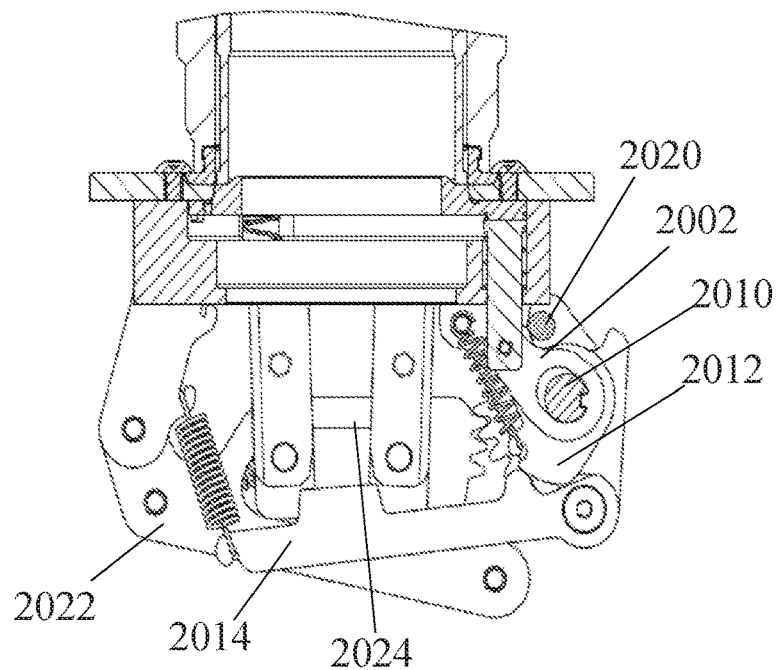

FIGS. 20C, 21C, and 22C illustrate other features of the pressure jacket and syringe retaining assembly 2000 including a springe plate 2002 that is biased in the distal direction when the syringe 2004 is not fully inserted and a keyed shaft, which are connected by a spring plate tab and a keyed shaft keyway. As the syringe 2004 is moved proximally, the syringe 2004 depresses the spring-loaded spring plate 2002 at the base of the retaining arms 2006a, 2006b in a proximal direction, thereby seating the syringe 2004 in the pressure jacket 2008. The spring plate 2002 resides in the assembly 2000 with a keyed shaft 2010 running through an elongated hole in the spring plate 2002 which allows the plate 2002 to translate in a direction perpendicular to the axis of the keyed shaft 2010 as the syringe 2004 presses downward on the spring plate 2002. The spring plate 2002 may also have a tab that may align with the keyway for the purpose of preventing rotation of the shaft 2010. The keyed shaft 2010 may be spring loaded in torsion.

Referring now to FIGS. 20C, 21C, and 22C, when the syringe 2004 is fully inserted, the spring plate 2002 releases the keyed shaft 2010 that was previously energized from removing the last syringe, as described below. The keyed shaft 2010 then rotates two similar cam plates 2012 (one on each side of the retention assembly 2000, only one shown in FIGS. 20B, 21B, and 22B). The cam plates 2012 in turn release two lock plates 2014 (one on each side of the retention assembly 2000, only one shown in FIGS. 20B, 21B, and 22B), that are rotated by spring force and wedge between the retaining arms 2006a, 2006b to prevent them from opening in the closed position.

As shown in FIGS. 21A-21C, once the syringe 2004 is fully inserted and the spring plate 2002 has released the keyed shaft 2010 that was previously energized from removing the last syringe and the lock plates 2014 are located between the retaining arms 2006a, 2006b, the syringe 2004 is fully installed and locked as shown in FIGS. 20A-20C. The injection procedure may then proceed for the fluid injector.

Removal of the syringe 2004 is illustrated in FIGS. 22A-22C. Referring to FIGS. 22A-22C, to remove the syringe 2004, a handle 2016 is pulled to approximately 45 degrees from its resting locked position. While the handle 2016 is moved, two actions occur substantially simultaneously. The handle 2016 is rigidly attached to two geared plates 2018 (one on each side, only one shown in FIGS. 22A-22C) that also have a pin 2020 pressed into them at a distance from the rotation axis. The pin 2020 contacts and drives the cam plates 2012 (see FIG. 22C) sharing the same axis of rotation as the gear plate 2018. The cam plate 2012 has a cam profile that drives the lock plate 2014 away from the retaining arms 2006a, 2006b, releasing them to allow syringe removal.

Referring now to FIGS. 20A-22C, the teeth of the gear plate 2018 are meshed with teeth of a lever plate 2022, which has a fixed rotation axis on the far side of the previously described plates. As the gear plate 2018 rotates (see FIGS. 20B, 21B, and 22B) it drives the lever plate 2022 with a mechanical advantage due to the reduction in gear ratio. As the lever plate 2022 is rotated, two cam profiles 2024 (one on each side of assembly) push the proximal portion of the retaining arms 2006a, 2006b together, which pivot the retaining arms 2006a, 2006b around their rotation axis causing them to open and release the syringe 2004.

Referring to FIGS. 22A-22C, once the handle 2016 is moved back to the set position, the keyed shaft 2010 aligns with the tab on the spring-loaded spring plate 2002 and the spring plate 2002 is biased in the distal direction, ejecting the syringe 2004 past the distal loading surfaces for removal by the operator. The assembly 2000 is then ready for installation of a new syringe for the next procedure.

While various examples of the present disclosure were provided in the foregoing description, those skilled in the art may make modifications and alterations to these examples without departing from the scope and spirit of the disclosure. Accordingly, the foregoing description is intended to be illustrative rather than restrictive. The disclosure described hereinabove is defined by the appended claims, and all changes to the disclosure that fall within the meaning and the range of equivalency of the claims are to be embraced within their scope.

We claim:

1. An assembly for retaining a pressure jacket and a syringe on a fluid injector, the assembly comprising:
    a base plate comprising a body;
    at least a first retaining arm and a second retaining arm operatively mounted on the body of the base plate, the first retaining arm having two first support arms pivotably connected at first pivot points to the base plate and the second retaining arm having two second support arms pivotably connected at second pivot points to the base plate, the first retaining arm having a first retaining surface at a distal end of the two first support arms and the second retaining arm having a second retaining surface at a distal end of the two second support arms, wherein the first retaining surface and the second retaining surface are configured for abutting a distal surface of at least one of the pressure jacket and the syringe; and
    a linkage assembly operatively connected to at least one of a proximal end of the first retaining arm and a proximal end of the second retaining arm,
    wherein the linkage assembly is configured to move at least one of the first retaining arm and the second retaining arm between at least a first open position and a closed position.

2. The assembly of claim 1, wherein the linkage assembly operatively connects the first retaining arm to the second retaining arm such that the first retaining arm and the second retaining arm are configured to move in unison between at least the first open position and the closed position.

3. The assembly of claim 2, wherein the linkage assembly comprises at least one biasing member configured for biasing the first retaining arm and the second retaining arm to move in unison between at least the first open position and the closed position.

4. The assembly of claim 3, wherein the at least one biasing member is configured to bias the first retaining arm and the second retaining arm in at least one of the first open position, a second open position, and the closed position.

5. The assembly of claim 1, wherein the first retaining arm and the second retaining arm pivot between at least the first open position and the closed position about the first pivot points and the second pivot points, respectively.

6. The assembly of claim 1, wherein the first retaining arm and the second retaining arm are further configured to move to a second open position between the first open position and the closed position.

7. The assembly of claim 6, wherein, in the first open position, the first retaining surface of the first retaining arm and the second retaining surface of the second retaining arm are separated from one another at a first distance configured to permit insertion and engagement of at least one of the pressure jacket and the syringe with the fluid injector or removal of at least one of the pressure jacket and the syringe from the fluid injector, wherein the first distance is greater than an outer diameter of the pressure jacket,
    wherein, in the closed position, the first retaining surface of the first retaining arm and the second retaining surface of the second retaining arm are separated from one another at a second distance to retain the pressure jacket and the syringe between the first retaining arm and the second retaining arm, wherein the second distance is less than an outer diameter of the syringe,
    wherein, in the second open position, the first retaining surface of the first retaining arm and the second retaining surface of the second retaining arm are separated from one another at a third distance to retain the pressure jacket in the fluid injector and allow removal of the syringe from the fluid injector,
    wherein the first distance is greater than the second distance, and
    wherein the third distance is less than the first distance and greater than the second distance.

8. The assembly of claim 1, wherein, in the first open position, the first retaining surface of the first retaining arm and the second retaining surface of the second retaining arm are separated from one another at a first distance configured to permit insertion and engagement of at least one of the pressure jacket and the syringe with the fluid injector or removal of at least one of the pressure jacket and the syringe from the fluid injector, wherein the first distance is greater than an outer diameter of the pressure jacket, wherein, in the closed position, the first retaining surface of the first retaining arm and the second retaining surface of the second retaining arm are separated from one another at a second distance to retain the pressure jacket and the syringe between the first retaining arm and the second retaining arm, wherein the second distance is less than an outer diameter of the syringe, and wherein the first distance is greater than the second distance.

9. The assembly of claim 1, wherein the first retaining surface of the first retaining arm comprises a first syringe retaining surface and a first pressure jacket retaining surface, and wherein the second retaining surface of the second retaining arm comprises a second syringe retaining surface and a second pressure jacket retaining surface.

10. An assembly for retaining a pressure jacket and a syringe on a fluid injector, the assembly comprising:
a base plate comprising a body; and
at least a first retaining arm and a second retaining arm operatively mounted on the body of the base plate, the first retaining arm having a first retaining surface at a distal end of two first support arms and the second retaining arm having a second retaining surface at a distal end of two second support arms, wherein the first retaining surface and the second retaining surface are configured for abutting and engaging a distal surface of at least one of the pressure jacket and the syringe,
wherein the two first support arms are pivotably connected at first pivot points to the base plate and the two second support arms are pivotably connected at second pivot points to the base plate.

11. The assembly of claim 10, wherein the first retaining surface of the first retaining arm and the second retaining surface of the second retaining arm each include at least one inner protrusion to engage a distal end of at least one of the pressure jacket and the syringe.

12. The assembly of claim 11, wherein at least one of the at least one inner protrusions is a syringe retaining protrusion extending at an angle relative to a longitudinal axis of the syringe and configured to interact with a corresponding angled distal surface of a circumferential wall on a distal end of the syringe to urge the distal ends of the first retaining arm and the second retaining arm with an inward retaining force.

13. The assembly of claim 10, wherein at least one of the first retaining arm and the second retaining arm includes at least one finger tab configured to assist in moving the first retaining arm and the second retaining arm between a closed position and an open position.

14. The assembly of claim 10, wherein, in an open position, the first retaining surface of the first retaining arm and the second retaining surface of the second retaining arm are separated from one another at a first distance configured to permit insertion and engagement of at least one of the pressure jacket and the syringe with the fluid injector or removal of at least one of the pressure jacket and the syringe from the fluid injector, wherein the first distance is greater than an outer diameter of the pressure jacket, wherein, in a closed position, the first retaining surface of the first retaining arm and the second retaining surface of the second retaining arm are separated from one another at a second distance configured to retain the pressure jacket and the syringe between the first retaining arm and the second retaining arm, wherein the second distance is less than an outer diameter of the syringe, and wherein the first distance is greater than the second distance.

15. An assembly for retaining a pressure jacket and a syringe on a fluid injector, the assembly comprising:
a base plate comprising a body;
at least a first retaining arm and a second retaining arm operatively mounted on the body of the base plate, the first retaining arm having a first retaining surface at a distal end thereof and the second retaining arm having a second retaining surface at a distal end thereof, wherein the first retaining surface and the second retaining surface are configured for abutting a distal surface of at least one of the pressure jacket and the syringe; and
a linkage assembly operatively connected to a proximal end of the first retaining arm and a proximal end of the second retaining arm,
wherein the linkage assembly is configured to move at least one of the first retaining arm and the second retaining arm between at least a first open position and a closed position, and
wherein each of the first retaining arm and the second retaining arm comprises two first support arms and two second support arms, respectively, operatively connected to the body of the base plate and the first retaining surface and the second retaining surface configured to engage at least one of the pressure jacket and the syringe when in the closed position, wherein the first retaining surface of the first retaining arm is provided on a retaining portion of the first retaining arm and the second retaining surface of the second retaining arm is provided on a retaining portion of the second retaining arm.

16. The assembly of claim 15, wherein the linkage assembly operatively connects the first retaining arm to the second retaining arm such that the first retaining arm and the second retaining arm are configured to move in unison between at least the first open position and the closed position.

17. The assembly of claim 15, wherein the first retaining arm and the second retaining arm are connected to the body of the base plate at first pivot points and second pivot points, respectively, so that the first retaining arm and the second retaining arm pivot between at least the first open position and the closed position about the first pivot points and the second pivot points.

18. The assembly of claim 15, wherein the first retaining arm and the second retaining arm are further configured to move to a second open position between the first open position and the closed position.

19. The assembly of claim 15, wherein, in the first open position, the first retaining surface of the first retaining arm and the second retaining surface of the second retaining arm are separated from one another at a first distance configured to permit insertion and engagement of at least one of the pressure jacket and the syringe with the fluid injector or removal of at least one of the pressure jacket and the syringe from the fluid injector, wherein the first distance is greater than an outer diameter of the pressure jacket, wherein, in the closed position, the first retaining surface of the first retaining arm and the second retaining surface of the second retaining arm are separated from one another at a second distance configured to retain the pressure jacket and the syringe between the first retaining arm and the second retaining arm, wherein the second distance is less than an outer diameter of the syringe, and wherein the first distance is greater than the second distance.

20. The assembly of claim 15, wherein the first retaining surface of the first retaining arm and the second retaining surface of the second retaining arm each include at least one inner protrusion to engage a distal end of at least one of the pressure jacket and the syringe.

21. The assembly of claim 20, wherein the at least one inner protrusion is a syringe retaining protrusion extending at an angle relative to a longitudinal axis of the syringe and configured to interact with a corresponding angled distal surface of a circumferential wall on a distal end of the syringe to urge the distal ends of the first retaining arm and the second retaining arm with an inward retaining force.

22. The assembly of claim 15, wherein at least one of the first retaining arm and the second retaining arm includes at least one finger tab configured to assist in moving the first retaining arm and the second retaining arm between the closed position and the first open position.

* * * * *

UNITED STATES PATENT AND TRADEMARK OFFICE
CERTIFICATE OF CORRECTION

Page 1 of 1

PATENT NO. : 11,918,775 B2
APPLICATION NO. : 17/640956
DATED : March 5, 2024
INVENTOR(S) : Spohn et al.

It is certified that error appears in the above-identified patent and that said Letters Patent is hereby corrected as shown below:

On the Title Page

In Item (72), under "Inventors:", in Column 1, Line 3, delete "Arthur Uber, III, Pittsburgh, PA (US)", therefor.

In Item (72), under "Inventors:", in Column 1, Line 5, delete "Andrew Osan, Pittsburgh, PA (US)", therefor.

In Item (72), under "Inventors:", in Column 1, Line 7, delete "James Dedig, Pittsburgh, PA (US)", therefor.

In Item (72), under "Inventors:", in Column 1, Line 8, delete "Andrew Naples, Mars, PA (US)", therefor.

In Item (72), under "Inventors:", in Column 1, Lines 10 and 11, delete "Michael Swantner, Saxonburg, PA (US)", therefor.

In Item (72), under "Inventors:", in Column 1, Lines 11 and 12, delete "Nathaniel Payor, Tarentum, PA (US)", therefor.

Signed and Sealed this
Second Day of September, 2025

Coke Morgan Stewart
*Acting Director of the United States Patent and Trademark Office*